United States Patent
Sosnowski et al.

(10) Patent No.: US 6,518,022 B1
(45) Date of Patent: *Feb. 11, 2003

(54) METHOD FOR ENHANCING THE HYBRIDIZATION EFFICIENCY OF TARGET NUCLEIC ACIDS USING A SELF-ADDRESSABLE, SELF-ASSEMBLING MICROELECTRONIC DEVICE

(75) Inventors: Ronald G. Sosnowski, Coronado; William F. Butler, Carlsbad; Eugene Tu; Michael I. Nerenberg, both of San Diego; Michael J. Heller, Encinitas; Carl F. Edman, San Diego, all of CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/444,539

(22) Filed: Nov. 22, 1999

Related U.S. Application Data

(63) Continuation of application No. 08/986,065, filed on Dec. 5, 1997, now Pat. No. 6,051,380, and a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662, and a continuation-in-part of application No. 08/708,262, filed on Sep. 6, 1996, now abandoned.

(51) Int. Cl.[7] ............................................. C12Q 1/68

(52) U.S. Cl. ...................... 435/6; 422/50; 422/68.1

(58) Field of Search ................ 435/6; 422/50, 422/68.1

(56) References Cited

U.S. PATENT DOCUMENTS

| 3,950,738 A | 4/1976 | Hayashi et al. ............... 365/185 |
| 3,995,190 A | 11/1976 | Salgo .......................... 313/391 |

(List continued on next page.)

FOREIGN PATENT DOCUMENTS

| EP | 0228075 | 7/1987 |
| GB | 2156074 | 10/1985 |

(List continued on next page.)

OTHER PUBLICATIONS

Abrams et al. "Comprehensive Detection of Single Base Changes In Human Genomic DNA Using Denaturing Gradient Gel Electrophoresis & a GC Clamp". *Genomics*, 7, 1990, 463–475.

(List continued on next page.)

*Primary Examiner*—Ardin H. Marschel
(74) *Attorney, Agent, or Firm*—Lyon & Lyon LLP

(57) ABSTRACT

A self-addressable, self-assembling microelectronic device is designed and fabricated to actively carry out and control multi-step and multiplex molecular biological reactions in microscopic formats. These reactions include nucleic acid hybridizations, antibody/antigen reactions, diagnostics, and biopolymer synthesis. The device can be fabricated using both microlithographic and micro-machining techniques. The device can electronically control the transport and attachment of specific binding entities to specific microlocations. The specific binding entities include molecular biological molecules such as nucleic acids and polypeptides. The device can subsequently control the transport and reaction of analytes or reactants at the addressed specific microlocations. The device is able to concentrate analytes and reactants, remove non-specifically bound molecules, provide stringency control for DNA hybridization reactions, and improve the detection of analytes. The device can be electronically replicated.

9 Claims, 26 Drawing Sheets

U.S. PATENT DOCUMENTS

| | | | |
|---|---|---|---|
| 4,283,773 A | 8/1981 | Daughton et al. | 364/132 |
| 4,563,419 A | 1/1986 | Ranki et al. | 435/6 |
| 4,580,895 A | 4/1986 | Patel | 356/39 |
| 4,584,075 A | 4/1986 | Goldstein | 204/522 |
| 4,594,136 A | 6/1986 | Goldstein | 204/551 |
| 4,751,177 A | 6/1988 | Stabinsky | 435/6 |
| 4,787,963 A | 11/1988 | MacConnell | 204/450 |
| 4,807,161 A | 2/1989 | Comfort et al. | 364/550 |
| 4,816,418 A | 3/1989 | Mack et al. | 436/518 |
| 4,822,566 A | 4/1989 | Newman | 422/82 |
| 4,828,729 A | 5/1989 | Klevan et al. | 435/6 |
| 4,908,112 A | 3/1990 | Pace | 210/198 |
| 4,936,963 A | 6/1990 | Mandecki et al. | 204/182 |
| 5,063,081 A | 11/1991 | Cozzette et al. | 435/4 |
| 5,074,977 A | 12/1991 | Cheung et al. | 205/775 |
| 5,075,077 A | 12/1991 | Durley, III et al. | 422/56 |
| 5,096,669 A | 3/1992 | Lauks et al. | 422/61 |
| 5,096,807 A | 3/1992 | Leaback | 435/6 |
| 5,110,434 A | 5/1992 | Zhu et al. | 204/183 |
| 5,125,748 A | 6/1992 | Bjornson et al. | 356/414 |
| 5,126,022 A | 6/1992 | Soane et al. | 204/458 |
| 5,143,854 A | 9/1992 | Pirrung et al. | 436/518 |
| 5,151,189 A | 9/1992 | Hu et al. | 210/635 |
| 5,164,319 A | 11/1992 | Hafeman et al. | 435/287 |
| 5,166,063 A | 11/1992 | Johnson | 435/173 |
| 5,192,405 A | 3/1993 | Petersen et al. | 204/180 |
| 5,200,051 A | 4/1993 | Cozzette et al. | 204/403 |
| 5,202,231 A | 4/1993 | Drmanac et al. | 435/6 |
| 5,219,726 A | 6/1993 | Evans | 435/6 |
| 5,227,265 A | 7/1993 | DeBoer et al. | 430/41 |
| 5,234,566 A | 8/1993 | Osman et al. | 204/403 |
| 5,242,797 A | 9/1993 | Hirshfeld | 435/6 |
| 5,304,487 A | 4/1994 | Wilding et al. | 435/29 |
| 5,312,527 A | 5/1994 | Mikkelsen et al. | 205/777 |
| 5,433,819 A | 7/1995 | McMeen | 216/20 |
| 5,434,049 A | 7/1995 | Okano et al. | 435/6 |
| 5,436,129 A | 7/1995 | Stapleton | 435/6 |
| 5,445,525 A | 8/1995 | Broadbent et al. | 439/64 |
| 5,464,517 A | 11/1995 | Hjerten et al. | 204/183 |
| 5,516,698 A | 5/1996 | Begg et al. | 436/89 |
| 5,527,670 A | 6/1996 | Stanley | 435/6 |
| 5,593,838 A | 1/1997 | Zansucci et al. | 435/6 |
| 5,605,662 A | 2/1997 | Heller et al. | 422/68 |
| 5,632,957 A | 5/1997 | Heller et al. | 422/68 |
| 5,653,939 A | 8/1997 | Hollis et al. | 422/50 |
| 5,660,701 A | 8/1997 | Grushka et al. | 204/451 |
| 5,681,751 A | 10/1997 | Begg et al. | 436/89 |
| 5,849,486 A | 12/1998 | Heller et al. | 435/6 |
| 6,013,166 A | 1/2000 | Heller | 204/469 |
| 6,017,696 A | 1/2000 | Heller et al. | 435/6 |
| 6,051,380 A * | 4/2000 | Sosnowski et al. | 435/6 |

FOREIGN PATENT DOCUMENTS

| | | |
|---|---|---|
| GB | 2247889 | 3/1992 |
| WO | WO 86/03782 | 7/1986 |
| WO | WO 88/08528 | 11/1988 |
| WO | WO89/01159 | 2/1989 |
| WO | WO 89/10977 | 11/1989 |
| WO | WO90/01564 | 2/1990 |
| WO | WO 92/04470 | 3/1992 |
| WO | WO93/22678 | 11/1993 |
| WO | WO95/07363 | 3/1995 |
| WO | WO 96/01836 | 1/1996 |
| WO | WO 98/01758 | 1/1998 |
| WO | WO 98/51819 | 11/1998 |
| YU | 57087 | 8/1990 |

OTHER PUBLICATIONS

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp 101–123.

Anderson and Young, "Quantitative Filter Hybridization," *Nucleic Acid Hybridization—A Practical Approach*, Eds. B.D. Hames and S.J. Higgins (Washington, D.C.:IRL Press 1985) pp 73–111.

Bains, "Setting a Sequence to Sequence a Sequence," *Bio/Technology*, 10:757–758 (1992).

Barinaga, "Will 'DNA Chip' Speed Genome Initiative?", *Science*, 253:1489 (1991).

Beattie et al., "Genosensor Technology," *The 1992 San Diego Conference: Genetic Recognition*, pp 1–5 (Nov., 1992).

Beltz et al., "Isolation of Multigene Families and Determination of Homologies by Filter Hybridization Methods," *Methods in Enzymology*, 100:266–285 (1983).

Brown et al. "Electrochemically Induced Adsorption of Radio–Labelled DNA on Gold and HOPG Substrates for STM Investigations". *Ultramicroscopy*, 38, 1991, 253–264.

Conner et al., "Detection of Sickle Cell $\beta^3$–Globin Allele by Hybridization With Synthetic Oligonucleotides," *Proc. Natl. Acad. Sci. USA*, 80:278–282 (1983).

Drmanac et al., "Sequencing of Megabase Plus DNA by Hybridization: Theory of the Method," *Genomics*, 4:114–128 (1989).

Drmanac et al., "DNA Sequence Determination by Hybridixation: A Strategy for Efficient Large–Scale Sequencing," *Science*, 260: 1649–1652 (1993).

Eggers et al. "Biochip Technology Development", BioChip Technology Development, Lincoln Laboratory Technical Report 901, Nov. 9, 1990.

Fiaccabrino et al., "Array of Individually Addressable Microelectrodes", Sensors and Actuators B, 18–19 (1994) 675–677.

Fodor et al., "Multiplexed Biochemical Assays With Biological Chips," *Nature*, 364:555–556 (1993).

Fodor et al., "Light–Directed, Spatially Addressable Parallel Chemical Synthesis," *Science*, 251:767–773 (1992).

Horejsi, "Some Theoretical Aspects of Affinity Electrophoresis," *Journal of Chromatography*, 178:1–13 (1979).

Horejsi et al., Determination of Dissociation Constants of Lectin Sugar Complexes by Means of Affinity Electrophoresis, *Biochimica at Biophysica Acta*, 499:200–300 (1977).

Kakerow et al., "A Monolithic Sensor Array of Individually Addressable Microelectrodes", Sensors and Actuators A, 43 (1994) 296–301.

Mathews, Kricka. "Analytical Strategies For The Use Of DNA Probes". *Analytical Biochemistry*, 169, 1988, 1–25.

Palecek. "New Trends in Electrochemical Analysis of Nucleic Acids", *Bioelectrochemistry and Bioenergetics*, 20, 1988, 179–194.

Ranki et al., "Sandwich Hybridization as a Convenient Method for the Detection of Nucleic Acids in Crude Samples," *Gene*, 21:77–85 (1983).

Saiki, "Amplification of Genomic DNA," *PCR Protocols: A Guide to Methods and Applications*, (Academic Press, Inc. 1990), pp 13–20.

Southern et al., "Analyzing and Comparing Nucleic Acid Sequences by Hybridization to Arrays of Oligonucleotides Evaluation Using Experimental Models," *Genomics*, 13:1008–1017 (1992).

Strezoska et al., "DNA Sequencing by Hybridization: 100 Bases Read by a Non–Gel–Based Method", *Proc. Natl. Acad. Sci. USA*, 88:10089–93 (1991).

Wallace et al., "Hybridization of Synthetic Oligodexribonucleotides to φx174 DNA: The Effect of Single Base Pair Mismatch," *Nucleic Acid Res.*, 6:3543–3557 (1979).

Washizu, "Electrostatic Manipulation of Biological Objects," *Journal of Electrostatics*, 25:109–123 (1990).

Washizu and Kurosawa, "Electrostatic Manipulation of DNA in Microfabricated Strucutures," *IEEE Transactions on Industry Applications*, 26:1165–1172 (1990).

Coombs, *Dictionary of Biotechnology*, Second Edition (1992).

* cited by examiner

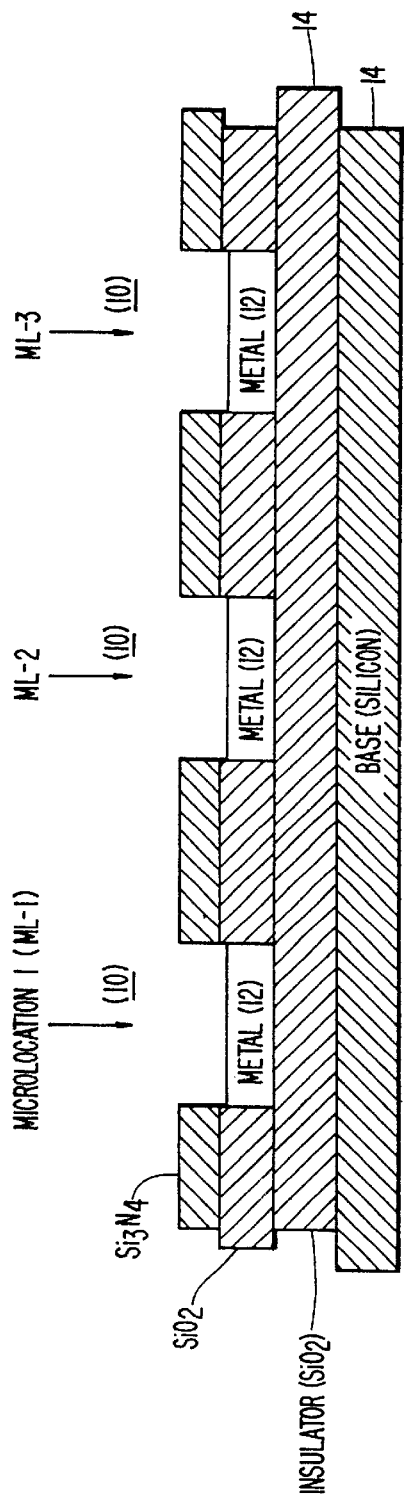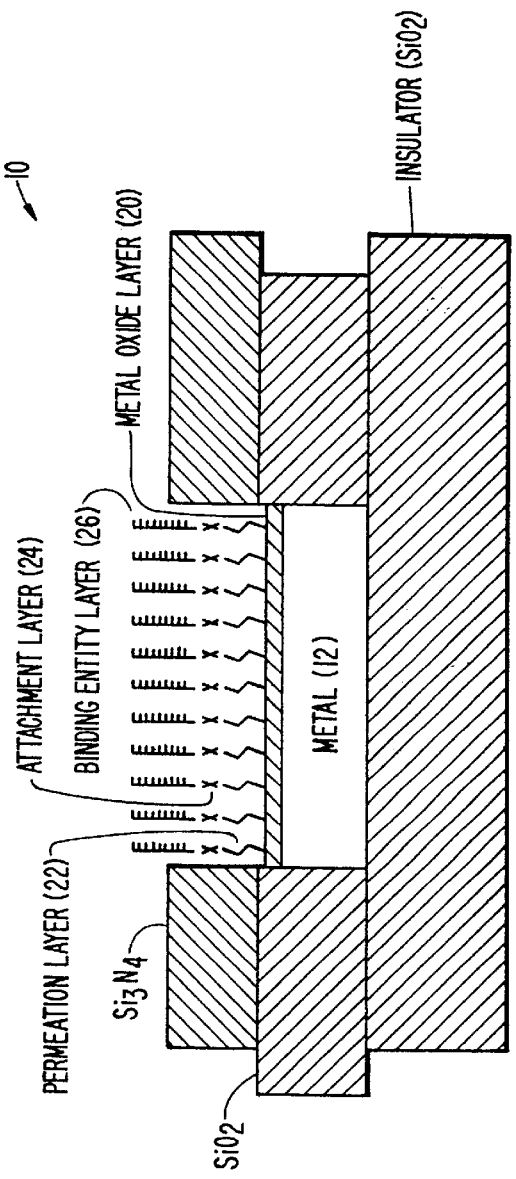

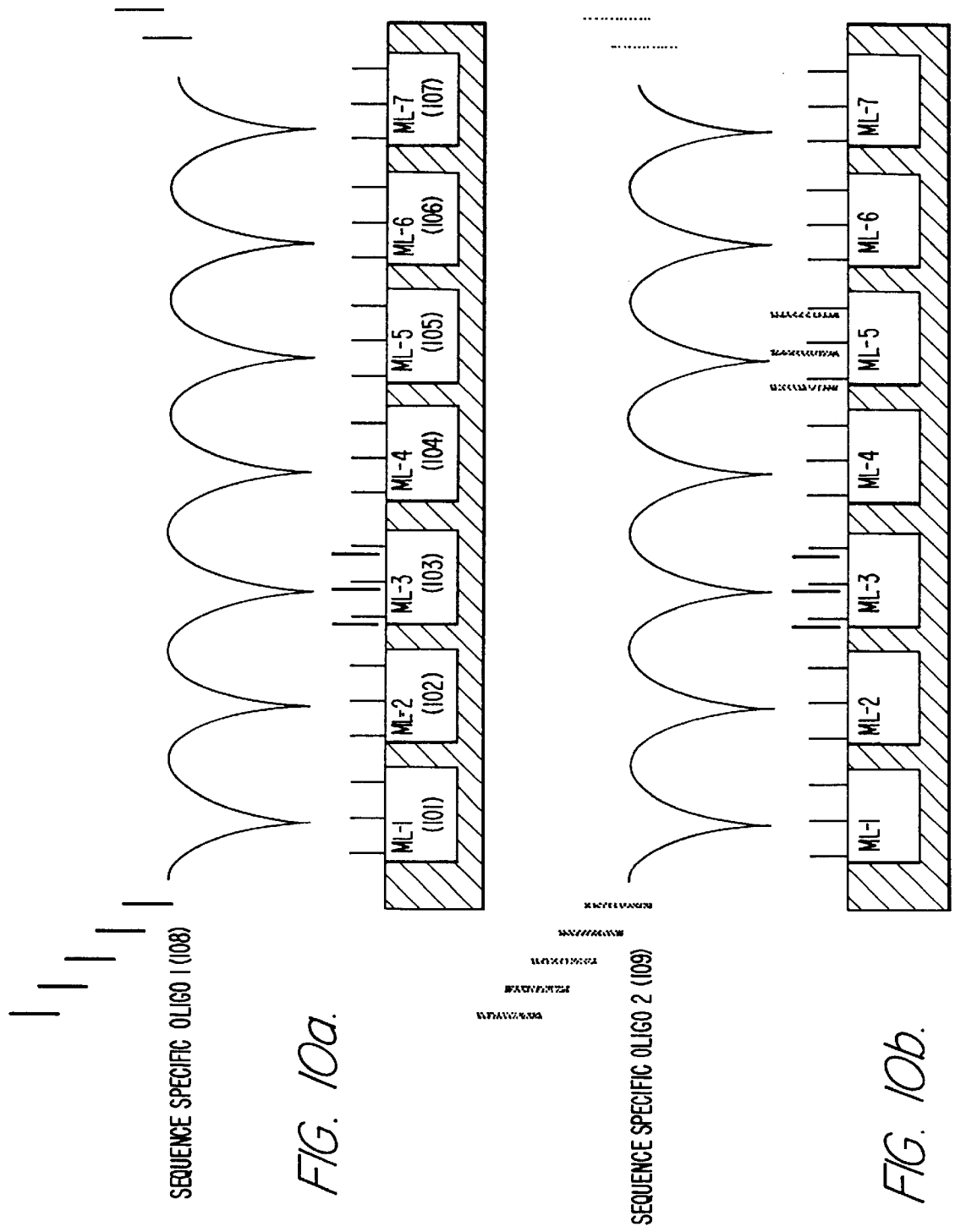

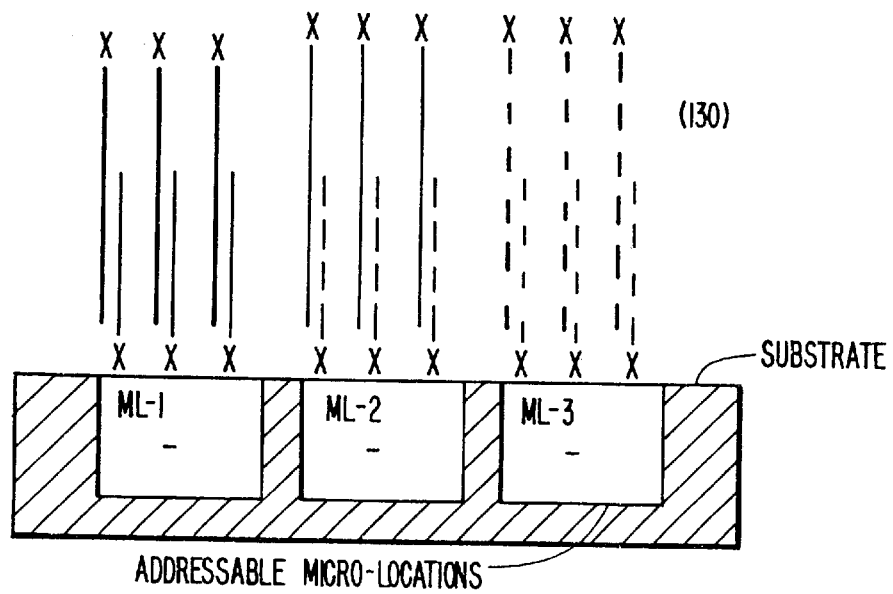
FIG. 13a.
ADDRESSABLE MICRO-LOCATIONS
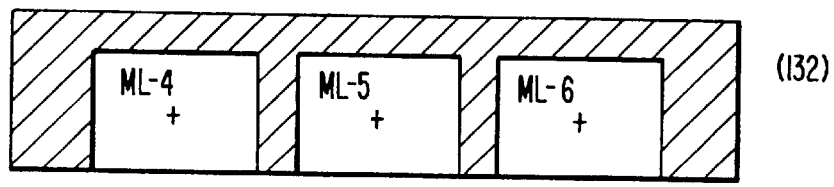
FIG. 13b.
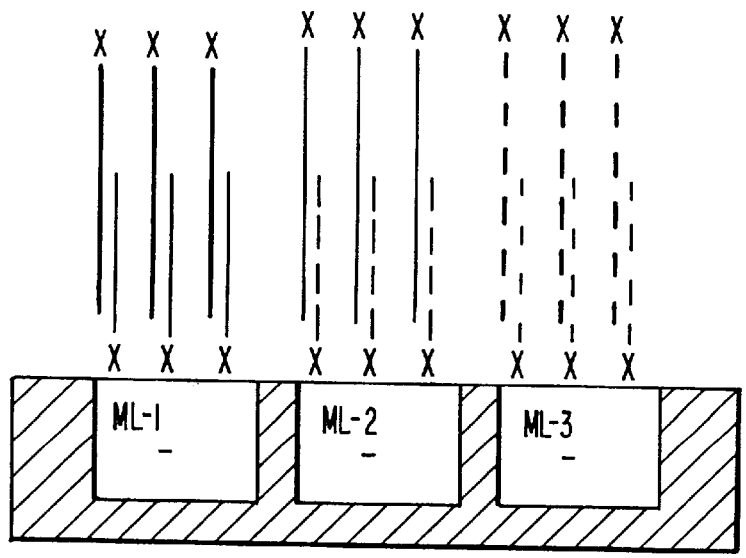

METHOD FOR ENHANCING THE HYBRIDIZATION EFFICIENCY OF TARGET NUCLEIC ACIDS USING A SELF-ADDRESSABLE, SELF-ASSEMBLING MICROELECTRONIC DEVICE

RELATED APPLICATION INFORMATION

This application is a continuation of U.S. patent application, Ser. No. 08/986,065, filed on Dec. 5, 1997, now U.S. Pat. No. 6,051,380; which is a continuation-in-part of application Ser. No. 08/534,454, filed Sep. 27, 1995, entitled "APPARATUS AND METHODS FOR ACTIVE PROGRAMMABLE MATRIX DEVICES" now U.S. Pat. No. 5,849,486, which is a continuation-in-part of application Ser. No. 08/304,657, filed Sep. 9, 1994, entitled "AUTOMATED MOLECULAR BIOLOGICAL DIAGNOSTIC SYSTEM," now issued as U.S. Pat. No. 5,632,957, (which has been continued into application Ser. No. 08/859,644, filed May 20, 1997, entitled "CONTROL SYSTEM FOR ACTIVE, PROGRAMMABLE ELECTRONIC MICROBIOLOGY SYSTEM"), which is a continuation-in-part of application Ser. No. 08/271,882, filed Jul. 7, 1994, entitled "METHODS FOR ELECTRONIC STRINGENCY CONTROL FOR MOLECULAR BIOLOGICAL ANALYSIS AND DIAGNOSTICS," now U.S. Pat. No. 6,017,696, which is a continuation-in-part of Ser. No. 08/146,504, filed Nov. 1, 1993, entitled "ACTIVE PROGRAMMABLE ELECTRONIC DEVICES FOR MOLECULAR BIOLOGICAL ANALYSIS AND DIAGNOSTICS", now issued as U.S. Pat. No. 5,605,662, (which has been continued into application Ser. No. 08/725,976, filed Oct. 4, 1996, entitled "METHODS FOR ELECTRONIC SYNTHESIS OF POLYMERS" now U.S. Pat. No. 5,929,208), and also a continuation-in-part of application Ser. No. 08/708,262, filed Sep. 6, 1996, entitled "METHODS AND MATERIALS FOR OPTIMIZATION OF ELECTRONIC HYBRIDIZATION REACTIONS", abandoned.

FIELD OF THE INVENTION

This invention pertains to the design, fabrication, and uses of a self-addressable, self-assembling microelectronic system which can actively carry out and control multi-step and multiplex reactions in microscopic formats. In particular, these reactions include molecular biological reactions, such as nucleic acid hybridizations, nucleic acid amplification, sample preparation, antibody/antigen reactions, clinical diagnostics, and biopolymer synthesis.

BACKGROUND OF THE INVENTION

Molecular biology comprises a wide variety of techniques for the analysis of nucleic acids and proteins, many of which form the basis of clinical diagnostic assays. These techniques include nucleic acid hybridization analysis, restriction enzyme analysis, genetic sequence analysis, and separation and purification of nucleic acids and proteins (See, e.g., J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989).

Many molecular biology techniques involve carrying out numerous operations on a large number of samples. They are often complex and time consuming, and generally require a high degree of accuracy. Many a technique is limited in its application by a lack of sensitivity, specificity, or reproducibility. For example, problems with sensitivity and specificity have so far limited the practical applications of nucleic acid hybridization.

Nucleic acid hybridization analysis generally involves the detection of a very small numbers of specific target nucleic acids (DNA or RNA) with probes among a large amount of non-target nucleic acids. In order to keep high specificity, hybridization is normally carried out under the most stringent conditions, achieved through various combinations of temperature, salts, detergents, solvents, chaotropic agents, and denaturants.

Multiple sample nucleic acid hybridization analysis has been conducted on a variety of filter and solid support formats (see G. A. Beltz et al., in *Methods in Enzymology*, Vol. 100, Part B, R. Wu, L. Grossmam, K. Moldave, Eds., Academic Press, New York, Chapter 19, pp. 266–308, 1985). One format, the so-called "dot blot" hybridization, involves the non-covalent attachment of target DNAs to a filter, which are subsequently hybridized with a radioisotope labeled probe(s). "Dot blot" hybridization gained widespread use, and many versions were developed (see M. L. M. Anderson and B. D. Young, in *Nucleic Acid Hybridization—A Practical Approach*, B. D. Hames and S. J. Higgins, Eds., IRL Press, Washington D.C., Chapter 4, pp. 73–111, 1985). The "dot blot" hybridization has been further developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

Another format, the so-called "sandwich" hybridization, involves attaching oligonucleotide probes covalently to a solid support and using them to capture and detect multiple nucleic acid targets. (M. Ranki et al., Gene, 21, pp. 77–85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. 6 Nucleic Acid Res. 11, p. 3543, 1979; and B. J. Connor et al., 80 Proc. Natl. Acad. Sci. USA pp. 278–282, 1983). Multiplex versions of these formats are called "reverse dot blots".

Using the current nucleic acid hybridization formats and stringency control methods, it remains difficult to detect low copy number (i.e., 1–100,000) nucleic acid targets even with the most sensitive reporter groups (enzyme, fluorophores, radioisotopes, etc.) and associated detection systems (fluorometers, luminometers, photon counters, scintillation counters, etc.).

This difficulty is caused by several underlying problems associated with direct probe hybridization. One problem relates to the stringency control of hybridization reactions. Hybridization reactions are usually carried out under the stringent conditions in order to achieve hybridization specificity. Methods of stringency control involve primarily the optimization of temperature, ionic strength, and denaturants in hybridization and subsequent washing procedures. Unfortunately, the application of these stringency conditions causes a significant decrease in the number of hybridized probe/target complexes for detection.

Another problem relates to the high complexity of DNA in most samples, particularly in human genomic DNA samples. When a sample is composed of an enormous number of sequences which are closely related to the specific target sequence, even the most unique probe sequence has a large number of partial hybridizations with non-target sequences.

A third problem relates to the unfavorable hybridization dynamics between a probe and its specific target. Even under the best conditions, most hybridization reactions are conducted with relatively low concentrations of probes and target molecules. In addition, a probe often has to compete with the complementary strand for the target nucleic acid.

A fourth problem for most present hybridization formats is the high level of non-specific background signal. This is caused by the affinity of DNA probes to almost any material.

These problems, either individually or in combination, lead to a loss of sensitivity and/or specificity for nucleic acid hybridization in the above described formats. This is unfortunate because the detection of low copy number nucleic acid targets is necessary for most nucleic acid-based clinical diagnostic assays.

Because of the difficulty in detecting low copy number nucleic acid targets, the research community relies heavily on the polymerase chain reaction (PCR) for the amplification of target nucleic acid sequences (see M. A. Innis et al., *PCR Protocols: A Guide to Methods and Applications*, Academic Press, 1990). The enormous number of target nucleic acid sequences produced by the PCR reaction improves the subsequent direct nucleic acid probe techniques, albeit at the cost of a lengthy and cumbersome procedure.

A distinctive exception to the general difficulty in detecting low copy number target nucleic acid with a direct probe is the in-situ hybridization technique. This technique allows low copy number unique nucleic acid sequences to be detected in individual cells. In the in-situ format, target nucleic acid is naturally confined to the area of a cell ($\sim 20$–$50\ \mu m^2$) or a nucleus ($\sim 10\ \mu m^2$) at a relatively high local concentration. Furthermore, the probe/target hybridization signal is confined to a microscopic and morphologically distinct area; this makes it easier to distinguish a positive signal from artificial or non-specific signals than hybridization on a solid support.

Mimicking the in-situ hybridization in some aspects, new techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "reverse dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1991; and R. Drmanac and R. B. Crkvenjakov, U.S. Pat. No. 5,202,231, Apr. 13, 1993).

There are two formats for carrying out SBH. One format involves creating an array of all possible n-mers on a support, which is then hybridized with the target sequence. This is a version of the reverse dot blot. Another format involves attaching the target sequence to a support, which is sequentially probed with all possible n-mers. Both formats have the fundamental problems of direct probe hybridizations and additional difficulties related to multiplex hybridizations. This inability to achieve "sequencing by hybridization" by a direct hybridization method lead to a so-called "format 3", which incorporates a ligase reaction step. While, providing some degree of improvement, it actually represents a different mechanism involving an enzyme reaction step to identify base differences.

Southern, United Kingdom Patent Application GB 8810400, 1988; E. M. Southern et al., 13 Genomics 1008, 1992, proposed using the "reverse dot blot" format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Fodor et al., 364 Nature, pp. 555–556, 1993, used an array of 1,024 8-mer oligonucleotides on a solid support to sequence DNA. In this case, the target DNA was a fluorescently labeled single-stranded 12-mer oligonucleotide containing only nucleotides the A and C bases. A concentration of 1 pmol ($\sim 6 \times 10^{11}$ molecules) of the 12-mer target sequence was necessary for the hybridization with the 8-mer oligomers on the array. The results showed many mismatches. Like Southern, Fodor et al., did not address the underlying problems of direct probe hybridization, such as stringency control for multiplex hybridizations. These problems, together with the requirement of a large quantity of the simple 12-mer target, indicate severe limitations to this SBH format.

Concurrently, Drmanac et al., 260 Science 1649–1652, 1993, used the above discussed second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency conditions were used to achieve specific hybridization for each n-mer probe; washing times varied from 5 minutes to overnight, and temperatures from 0° C. to 161° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

Fodor et al., 251 Science 767–773, 1991, used photolithographic techniques to synthesize oligonucleotides on a matrix. Pirrung et al., in U.S. Pat. No. 5,143,854, Sep. 1, 1992, teach large scale photolithographic solid phase synthesis of polypeptides in an array fashion on silicon substrates.

In another approach of matrix hybridization, Beattie et al., in *The 1992 San Diego Conference: Genetic Recognition*, November, 1992, used a microrobotic system to deposit micro-droplets containing specific DNA sequences into individual microfabricated sample wells on a glass substrate. The hybridization in each sample well is detected by interrogating miniature electrode test fixtures, which surround each individual microwell with an alternating current (AC) electric field.

Regardless of the format, all current micro-scale DNA hybridizations and SBH approaches do not overcome the underlying problems associated with nucleic acid hybridization reactions. They require very high levels of relatively short single-stranded target sequences or PCR amplified DNA, and produce a high level of false positive hybridization signals even under the most stringent conditions. In the case of multiplex formats using arrays of short oligonucleotide sequences, it is not possible to optimize the stringency condition for each individual sequence with any conventional approach because the arrays or devices used for these formats can not change or adjust the temperature, ionic strength, or denaturants at an individual location, relative to other locations. Therefore, a common stringency condition must be used for all the sequences on the device. This results in a large number of non-specific and partial hybridizations and severely limits the application of the device. The problem becomes more compounded as the number of different sequences on the array increases, and as the length of the sequences decreases below 10-mers or increase above 20-mers. This is particularly troublesome for SBH, which requires a large number of short oligonucleotide probes.

Nucleic acids of different size, charge, or conformation are routinely separated by electrophoresis techniques which can distinguish hybridization species by their differential mobility in an electric field. Pulse field electrophoresis uses an arrangement of multiple electrodes around a medium (e.g., a gel) to separate very large DNA fragments which cannot be resolved by conventional gel electrophoresis systems (see R. Anand and E. M. Southern in *Gel Electrophoresis of Nucleic Acids—A Practical Approach*, 2 ed., D. Rickwood and B. D. Hames Eds., IRL Press, New York, pp. 101–122, 1990).

Pace, U.S. Pat. No. 4,908,112, Mar. 13, 1990, describes using micro-fabrication techniques to produce a capillary gel electrophoresis system on a silicon substrate. Multiple electrodes are incorporated into the system to move molecules through the separation medium within the device.

Soane and Soane, U.S. Pat. No. 5,126,022, Jun. 30, 1992, describe that a number of electrodes can be used to control the linear movement of charged molecules in a mixture through a gel separation medium contained in a tube. Electrodes have to be installed within the tube to control the movement and position of molecules in the separation medium.

Washizu, M. and Kurosawa, O., 26 IEEE Transactions on Industry Applications 6, pp. 1165–1172, 1990, used high-frequency alternating current (AC) fields to orient DNA molecules in electric field lines produced between micro-fabricated electrodes. However, the use of direct current (DC) fields is prohibitive for their work. Washizu 25 Journal of Electrostatics 109–123, 1990, describes the manipulation of cells and biological molecules using dielectrophoresis. Cells can be fused and biological molecules can be oriented along the electric fields lines produced by AC voltages between the micro-electrode structures. However, the dielectrophoresis process requires a very high frequency AC (1 MHz) voltage and a low conductivity medium. While these techniques can orient DNA molecules of different sizes along the AC field lines, they cannot distinguish between hybridization complexes of the same size.

MacConnell, U.S. Pat. No. 4,787,936, Nov. 29, 1988, describes methods and means for annealing complementary nucleic acid molecules at an accelerated rate. The nucleic acid probes are electrophoretically concentrated with a surface to which various sequences are bound. Unannealed probe molecules are electronically removed from the surface region by reversal of the electrical orientation, so as to electrophoretically move away from the surface of those materials which had been previously concentrated at the surface. In yet another aspect, the patent describes moving concentrated, unannealed probe molecules successively in various directions along the surface to which the sequences are bound.

Stanley, C. J., U.S. Pat. No. 5,527,670, issued Jun. 18, 1996, claiming priority to GB 9019946, filed Sep. 12, 1990 and GB 9112911 filed Jun. 14, 1991. Stanley discloses a process for denaturing native double-stranded nucleic acid material into its individual strands in an electrochemical cell. An electrical treatment of the nucleic acid with a voltage applied to the nucleic acid material by an electrode is utilized. Promotor compounds, such as methylviologen, are suggested to speed denaturation. The process is suggested for use in the detection of nucleic acid by hybridizing with a labeled probe or in the amplification of DNA by a polymerase chain reaction or ligase chain reaction.

More recently, attempts have been made at microchip based nucleic acid arrays to permit the rapid analysis of genetic information by hybridization. Many of these devices take advantage of the sophisticated silicon manufacturing processes developed by the semiconductor industry over the last fourty years. In these devices, many parallel hybridizations may occur simultaneously on immobilized capture probes. Stringency and rate of hybridization is generally controlled by temperature and salt concentration of the solutions and washes. Even though of very high probe densities, such a "passive" micro-hybridization approaches have several limitations, particularly for arrays directed at reverse dot blot formats, for base mismatch analysis, and for re-sequencing and sequencing by hybridization applications.

First, as all nucleic acid probes are exposed to the same conditions simultaneously, capture probes must have similar melting temperatures to achieve similar levels of hybrid stringency. This places limitations on the length, GC content and secondary structure of the capture probes. Also, single-stranded target fragments must be selected out for the actual hybridization, and extremely long hybridization and stringency times are required(see, e.g., Guo,Z, et.al., Nucleic Acid Research, V.22, #24, pp 5456–5465, 1994).

Second, for single base mismatch analysis and re-sequencing applications a relatively large number of capture probes (>16) must be present on the array to interrogate each position in a given target sequence. For example, a 400 base pair target sequence would require an array with over 12,000 different probe sequences (see, e.g., Kozal, M. J., et.al., Nature Medicine, V.2, #7, pp.753–759, 1996).

Third, for many applications large target fragments, including PCR or other amplicons, can not be directly hybridized to the array. Frequently, complicated secondary processing of the amplicons is required, including: (1) further amplification; (2) conversion to single-stranded RNA fragments; (3) size reduction to short oligomers, and (4) intricate molecular biological/enzymatic reactions steps, such as ligation reactions.

Fourth, for passive hybridization the rate is proportional to the initial concentration of the target fragments in the solution, therefore, very high concentrations of target is required to achieve rapid hybridization.

Fifth, because of difficulties controlling hybridization conditions, single base discrimination is generally restricted to capture oligomers sequences of 20 bases or less with centrally placed differences (see, e.g., Chee '96; Guo,Z, .et.al., Nucleic Acid Research, V.22, #24, pp 5456–5465, 1994; Kozal, M. J., et.al., Nature Medicine, V.2, #7, pp. 753–759, 1996).

As is apparent from the preceding discussion, numerous attempts have been made to provide effective techniques to conduct multi-step, multiplex hybridizations and other molecular biological reactions. However, for at least the reasons stated above, these techniques have been proved deficient. Despite the long-recognized need for effective technique, no satisfactory solution has been proposed previously.

SUMMARY OF THE INVENTION

In an attempt to circumvent these limitations, a microelectronic based nucleic acid array utilizes electric fields as an independent parameter to control transport, hybridization and stringency of nucleic acid interactions. These are "active" array devices in that they exploit microelectronic as well as microfabrication technology. Now, in addition to salt, pH, temperature and chaotropic agents, the electric field strength (in particular the current level and density) provides a precisely controllabe and continuously variable parameter for adjustment of nucleic acid interactions.

The present invention relates to the design, fabrication, and uses of programmable, self-addressable and self-assembling microelectronic systems and devices which can actively carry out controlled multi-step and multiplex reactions in microscopic formats. These reactions include, but are not limited to, most molecular biological procedures, such as nucleic acid hybridizations, antibody/antigen reaction, cell separation, and related clinical diagnostics.

In addition, the devices are able to carry out multi-step combinational biopolymer and combinatorial synthesis, including, but not limited to, the synthesis of different oligonucleotides or peptides at specific microlocations.

In addition, the microelectronic devices and methods of this invention allow rapid multiplex hybridization and discrimination of single base mismatches in full length DNA fragments and PCR amplicons, under what would be considered substantially non-hybridizing and non-stringent conditions by any passive or conventional hybridization technique.

The devices are fabricated using both microlithographic and micromachining techniques. The devices have a matrix of addressable microscopic locations on their surface; each individual microlocation is able to electronically control and direct the transport and attachment of specific binding entities (e.g., nucleic acids, antibodies) to itself. All microlocations can be addressed with their specific binding entities. Using these devices, the system can be self-assembled with minimal outside intervention.

One key aspect of this invention is played by the ion-permeable "permeation" layer which overlies the electrode. This permeation layer allows attachment of nucleic acids to permit immobilization. More importantly, the permeation layer separates the attached or tethered oligonucleotides and hybdridized target DNA sequences from the highly reactive electrochemical environment generated immediately at the electrode surface. This highly reactive electrode surface and its electrochemical products can rapidly destroy DNA probes and target DNA sequences which contact it or approach it too closely. This permeation layer thereby allows oligonucleotides and DNA fragments to be "electronically targeted" above the actual electrode surface and hybridized to anchored complementary oligonucleotides while being protected from the reactive surface and environment. Most importantly, the design of the microelectrode and permeation layer to form a microlocation structure, allows high current densities to be achieved in an extremely confined area, while minimizing the adverse effects produced by the electrode itself.

The addressed devices are able to control and actively carry out a variety of assays and reactions. Analytes or reactants can be transported by free field electrophoresis to any specific microlocation where the analytes or reactants are effectively concentrated and reacted with the specific binding entity at said microlocation. The sensitivity for detecting a specific analyte or reactant is improved because of the concentrating effect. Any un-bound analytes or reactants can be removed by reversing the polarity of a microlocation. More importantly, the ability to produce a precisely controlled high current level or density at a microlocation, allows the selective "de-hybridization" of DNA fragments to be achieved to the level of single base mismatches or even completely complementary sequences. Thus, the devices also improve the specificity of assays and reactions.

The active nature of the devices provide independent electronic control over all aspects of the hybridization reaction (or any other affinity reaction) occurring at each specific microlocation. These devices provide a new mechanism for affecting hybridization reactions which is called electronic stringency control (ESC). For DNA hybridization reactions which require different stringency conditions, ESC overcomes the inherent limitation of conventional array technologies. The active devices of this invention can electronically produce "different stringency conditions" at each microlocation. Thus, all hybridizations can be carried out optimally in the same bulk solution. These active devices are fundamentally different from convention multiplex hybridization arrays and DNA chips. While conventional arrays have different probes or target DNA's located at each site; all the sites on the array have the same common reaction or stringency conditions of temperature, buffer, salt concentration, and pH. Any change in the reaction or stringency condition, affects all sites on the array. While sophisticated photolithographic techniques may be used to make an array, or microelectronic sensing elements are incorporated for detection, conventional devices are passive and do not control or influence the actual hybridization process. The active devices of this invention allow each microlocation to function as a completely independent test or analysis site (i.e. they form the equivalent of a "test tube" at each location). Multiple hybridization reactions can be carried out with minimal outside physical manipulations. Additionally, it is unnecessary to change temperatures, and the need for multiple washing procedures is greatly reduced.

Another important consideration is the composition of the transport and hybridization buffers. To facilitate rapid movement of nucleic acids by free solution electrophoresis, low conductivity buffers have been utilized. To achieve low conductivity and preserve good buffering capacity, zwitterionic buffers have been used that have little or no net charge at their pI. These buffers, typically possess conductivities less than 100 mS/cm. Buffers commonly employed in molecular biology have conductivities a thousand fold greater, e.g. 6× sodium chloride/sodium citrate (SSC). Low conductivity and zwitterionic buffers with no net charge do not optimally shield nucleic acid phosphodiester backbone charges and therefore, under passive conditions, do not aid in hybridization. While we do not wish to be bound by any particular theory, it is believed that this probably helps to prevent self annealing of denatured nucleic acids prior to transport. However, it has been empirically discovered that some of these buffers selectively facilitate electronically accelerated hybridization.

Thus, the disclosed devices can carry out multi-step and multiplex reactions with complete and precise electronic control, preferably under overall micro-processor control (i.e. run by a computer). The rate, specificity, and sensitivity of multi-step and multiplex reactions are greatly improved at specific microlocations on the disclosed device.

The device also facilitates the detection of hybridized complexes at each microlocation by using an associated optical (fluorescent, chemiluminescent, or spectrophotometric) imaging or scanning detector system. Integrated optoelectronic or electronic sensing components which directly detect DNA, can also be incorporated within the device itself. That is, optical wave guides, lasers, and detectors may be microfabricated into the APEX chip device itself, since it is a silicon based structure.

If desired, a master device addressed with specific binding entities can be electronically replicated or copied to another base device. Thus, allowing rapid manufacture of array devices.

This invention may utilize microlocations of any size or shape consistent with the objective of the invention. In one of the preferred embodiments of the invention, microlocations in the sub-millimeter (10–100 micron) range are used. By "specific binding entity" is generally meant any biological or synthetic molecule that has specific affinity to another molecule, macromolecule or cells, through covalent bonding or non-covalent bonding. Preferably, a specific binding entity contains (either by nature or by modification) a functional chemical group (primary amine, sulfhydryl, aldehyde, etc.), a common or unique sequence (nucleic acids), an epitope (antibodies), a hapten, or a ligand, that allows it to covalently react or non-covalently bind to a common functional group on the surface of a microlocation. Specific binding entities include, but are not limited to: deoxyribonucleic acids (DNA), ribonucleic acids (RNA), synthetic oligonucleotides, peptide nucleic acids (PNA), antibodies, proteins, peptides, lectins, modified polysaccharides, cells, synthetic composite macromolecules, functionalized nanostructures, functionalized microstructures, synthetic polymers, modified/blocked nucleotides/nucleosides, modified/blocked amino acids, fluorophores, chromophores, ligands, chelates and haptens.

By "stringency control" is meant the ability to discriminate specific and non-specific binding interactions by changing some physical parameter. In the case of nucleic acid hybridizations, temperature control is often used for stringency. Reactions are carried out at or near the melting temperature (Tm) of the particular double-stranded hybrid pair.

Thus, one aspect of the present invention is a device with an array of electronically programmable and self-addressable microscopic locations. Each microscopic location contains an underlying working direct current (DC) or DC/AC microelectrode supported by a substrate. The surface of each microlocation has a permeation layer for the free transport of small counter-ions, and an attachment layer for the covalent coupling of specific binding entities. These unique design features provide the following critical properties for the device: (1) allow a controllable functioning DC electrode to be maintained beneath the microlocation; (2) allow electrophoretic transport to be maintained; and (3) separate the affinity or binding reactions from the electrochemical and the adverse electrolysis reactions occurring at the electrode (metal) interfaces. It should be emphasized that the primary function of the micro-electrodes used in these devices is to provide electrophoretic propulsion of binding and reactant entities to specific locations.

By "array" or "matrix" is meant an arrangement of addressable locations on the device. The locations can be arranged in two dimensional arrays, three dimensional arrays, or other matrix formats. The number of locations can range from several to at least hundreds of thousands. Most importantly, each location represents a totally independent reaction site.

In a second aspect, this invention features a method for transporting the binding entity to any specific microlocation on the device. When activated, a microlocation can affect the free field electrophoretic transport of any charged functionalized specific binding entity directly to itself. Upon contacting the specific microlocation, the functionalized specific binding entity immediately becomes covalently attached to the attachment layer surface of that specific microlocation. Other microlocations can be simultaneously protected by maintaining them at the opposite potential to the charged molecules. The process can be rapidly repeated until all the microlocations are addressed with their specific binding entities.

By "charged functionalized specific binding entity" is meant a specific binding entity that is chemically reactive (i.e., capable of covalent attachment to a location) and carries a net change (either positive or negative).

In a third aspect, this invention features a method for concentrating and reacting analytes or reactants at any specific microlocation on the device. After the attachment of the specific binding entities, the underlying microelectrode at each microlocation continues to function in a direct current (DC) mode. This unique feature allows relatively dilute charged analytes or reactant molecules free in solution to be rapidly transported, concentrated, and reacted in a serial or parallel manner at any specific microlocations which are maintained at the opposite charge to the analyte or reactant molecules. Specific microlocations can be protected or shielded by maintaining them at the same charge as the analytes or reactants molecules. This ability to concentrate dilute analyte or reactant molecules at selected microlocations greatly accelerates the reaction rates at these microlocations.

When the desired reaction is complete, the microelectrode potential can be reversed to remove non-specific analytes or unreacted molecules from the microlocations.

Specific analytes or reaction products may be released from any microlocation and transported to other locations for further analysis; or stored at other addressable locations; or removed completely from the system.

The subsequent analysis of the analytes at the specific microlocations is also greatly improved by the ability to repulse non-specific entities and de-hybridize sequences from these locations.

In a fourth aspect, this invention features a method for improving efficiency and stringency of nucleic acid hybridization reactions, comprising the steps of:

rapidly concentrating dilute target DNA and/or probe DNA sequences at specific microlocation(s) where hybridization is to occur;

rapidly removing non-specifically bound target DNA sequences from specific microlocation(s) where hybridization has occurred;

rapidly removing competing complementary target DNA sequences from specific microlocation(s) where hybridization has occurred;

adjusting electronic stringency control (ESC) via current level and density to remove partially hybridized DNA sequences (more than one base mis-match);

adjusting ESC via current level and density to improve the resolution of single mis-match hybridizations using probes in the 8-mer to 21-mer range(e.g., to identify point mutations);

using ESC via current level and density, to utilize oligonucleotide point mutation probes outside of the ranges used in conventional procedures (e.g., probes longer than 21-mers and shorter than 8-mers); for example, 22-mer to 30-mer and longer.

applying ESC, via current level and density, to discriminate single nucleotide polymorphisms (SNPs).

using ESC to improve the overall hybridization of amplified target DNA and RNA sequences on arrays of capture probe oligonucleotides.

using ESC to improve the hybridization of any target DNA or RNA sequences on arrays of capture probe oligonucleotides in reverse dot blot formats.

using ESC to improve the hybridization of any target DNA or RNA sequences on arrays of capture probe oligonucleotides in sandwich formats.

using ESC to improve the hybridization of any DNA or RNA sequence on arrays of nucleic acid sequences in the more classical dot blot format (target sequences on the array, reporter probes added)

using ESC to improve the hybridization of target nucleic acid sequences on arrays of nucleic acid probes in homogeneous/heterogeneous hybridization formats.

using ESC to improve the hybridization of target RNA sequences on arrays of nucleic acid probes for gene expression applications.

applying independent ESC to individual hybridization events occurring in the same bulk solution and at the same temperature; and using ESC to improve hybridization of un-amplified target DNA sequences to arrays of capture oligonucleotide probes.

In a fifth aspect, this invention features a method for the combinatorial synthesis of biopolymers at microlocations.

In a sixth aspect, this invention features a method for replicating arrays from a master device.

In a seventh aspect, this invention features a device which electronically carries out sample preparation and transports target DNA to the analytical component of the device In an eighth aspect, this invention features a device which electronically delivers reagents and reactants with minimal use of fluidics.

In a ninth aspect, this invention features a device which carries out molecular biology and DNA amplification reactions (e.g. restriction cleavage reactions, DNA/RNA polymerase and DNA ligase target amplification reactions.

In a tenth aspect, this invention features a device which is can electronically size and identify restriction fragments (e.g. carry out electronic restriction fragment length polymorphism and DNA finger printing analysis).

In an eleventh aspect, this invention features a device which carries out antibody/antigen and immunodiagnostic reactions.

In a twelfth aspect, this invention features a device which is able to carry out combinatorial synthesis of oligonucleotides and peptides.

In a thirteenth aspect, this invention features a device which selectively binds cells, processes cells for hybridization, lyses and removes DNA from cells, or carries out electronic in-situ hybridizations within the cells.

In a fourteenth aspect, this invention features methods for detecting and analyzing reactions that have occurred at the addressed microlocations using self-addressed microelectronic devices with associated optical, optoelectronic or electronic detection systems or self-addressed microelectronic devices with integrated optical, optoelectronic or electronic detection systems.

In a fifteenth aspect, this invention features devices and methods which allow rapid multiplex hybridization and discrimination of single base mismatches in full length double-stranded or single-stranded DNA fragments, RNA fragments, PCR amplicons, and SDA amplicons, under what would be considered substantially non-hybridizing and non-stringent conditions by any passive or conventional hybridization technique.

In a sixteenth aspect, this invention features electronic hybridization methods which incorporate buffer and electrolyte compounds (including but not limited to: histidine, di-histidine, histidine peptides, mixed histidine peptides, and other low conductivity/DNA helix stabilizing compounds) which produce rapid transport and hybridization of nucleic acid fragments (DNA, RNA, etc.)under what would be considered substantially non-hybridizing and non-stringent conditions by any passive or conventional hybridization technique.

In a seventeenth aspect, this invention features devices and methods which allow rapid multiplex hybridization and discrimination of multiple repeat sequences (di-, tri, tetra, etc.), including short tandem repeats (STRs) in nucleic acid fragments, under what would be considered substantially non-hybridizing and non-stringent conditions by any passive or conventional hybridization technique.

In an eighteenth aspect, this invention features devices and methods which allow rapid multiplex hybridization in in-situ formats.

In a nineteenth aspect, this invention features devices and methods which can be combined into an instrument system which allows addressing of an APEX chip device for so-called "make your own chip" products and applications.

In the twentieth aspect, this invention features improved permeation layers that contain compounds or materials which help maintain the stability of the DNA hybrids; these can include but are not limited to histidine, histidine peptides, polyhistidine, lysine, lysine peptides, and other cationic compounds or substances.

Because the devices of this invention are active programmable electronic matrices, the acronym "APEX" is used to describe or designate the unique nature of these devices. The APEX acronym is used for both the microlithographically produced "chips" and micro-machined devices.

The active nature of APEX microelectronic devices and chips allows us to create new mechanisms for carrying out a wide variety of molecular biological reactions. These include novel methods for achieving both linear and exponential multiplication or amplification of target DNA and RNA molecules.

The device provides electronic mechanisms to: (1) selectively denature DNA hybrids in common buffer solutions at room temperatures (e.g. well below their Tm points); (2)to rapidly transport or move DNA back and forth between two or more microlocations; and (3) to selectively concentrate the specific reactants, reagents, and enzymes at the desired microlocations. These all involve new physical parameters for carrying out molecular biological and target amplification type reactions.

A number of examples of electronically controlled molecular biology reactions have been developed, these include: (1) Electronically Directed Restriction Enzyme Cleavage of Specific ds-DNA Sequences; (2) Electronic Restriction Fragment Analysis; (3) Electronic Multiplication of Target DNA by DNA Polymerases; and (4) Electronic Ligation and Multiplication of Target DNA Sequences By DNA and RNA Polymerases; and (5) Electronic Multiplication of Target DNA by RNA Polymerases. These examples are representative of the types of molecular biological reactions and procedures which can be carried out on the APEX devices.

Other features and advantages of the invention will be apparent from the following detailed description of the invention, and from the claims.

BRIEF DESCRIPTION OF THE DRAWINGS

FIG. 1 is the cross-section of three self-addressable microlocations fabricated using microlithographic techniques.

FIG. 2 is the cross-section of a microlithographically fabricated microlocation.

FIGS. 10a and 10b show an electronically directed serial hybridization process, FIG. 10a showing materials adjacent microlocations ML-3 and FIG. 10b showing materials adjacent microlocation ML-3 and ML-5.

FIGS. 13a, 13b and 13c show a scheme of electronically controlled replication of devices, FIG. 13a showing negatively charged addressable microlocations, FIG. 13b showing two opposed substrates, one substrate being that of FIG. 13a and the other being a sister device containing an attachment layer, and FIG. 13c showing two substrates, each of which has sequences bound to the microlocations.

DETAILED DESCRIPTION OF THE INVENTION

Introduction

Figure 3:
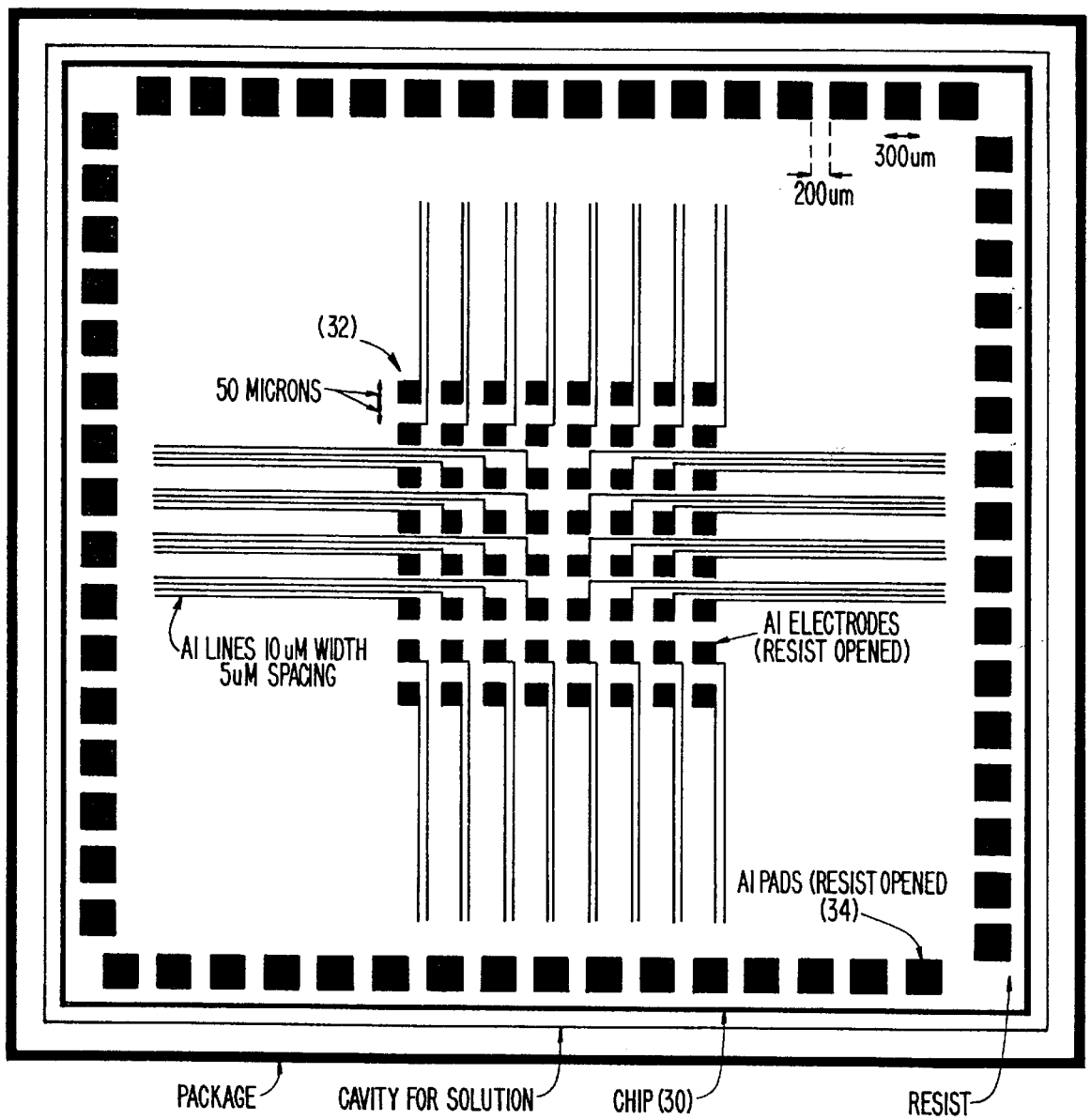
FIG. 3 is a schematic representation of a self-addressable 64 microlocation chip.

The devices and the related methodologies of this invention allow molecular biology and diagnostic reactions to be carried out under "complete electronic control". The meaning of "electronic control" as referred to in this invention goes beyond the conventional connotation of the term. Most conventional microelectronic devices, instruments, and detector systems are always at some level under electronic control. The microelectronic devices of this invention are not only under conventional electronic control, but more importantly they also provide further direct electronic control over the physical aspects of carrying out molecular biological and diagnostic reactions. This invention provides a microelectronic device with programmable and addressable microscopic locations.

In the preferred embodiment, each microlocation has a derivatized upper surface for the covalent attachment of specific binding entities (i.e., an attachment layer), an intermediate permeation layer, and an underlying direct current (DC) microelectrode (with option to run DC/AC). After the initial fabrication of the basic microelectronic structure, the device is able to self-direct the addressing of each specific microlocation with specific binding entities. Thus, the devices and methods of this invention can be combined into an instrument system which allows addressing of an APEX chip device with any DNA or RNA probe, or any other ligand. Such a system would allow "make your own chip" products and applications. Such products and applications would be useful to many researchers and end users for clinical diagnostic, molecular biology, functional genomic and drug discovery applications. The self-addressed device is subsequently able to actively carry out individual multi-step and combinatorial reactions at any of its microlocations. The device is able to carry out multiplex reactions, but with the important advantage that each reaction occurs at the equivalent of a truly independent test site. The device is able to electronically direct and control the rapid movement and concentration of analytes and reactants to or from any of its microlocations. The ability of the device to electronically control the dynamic aspects of various reactions provides a number of new mechanisms and important advantages and improvements.

The concepts and embodiments of this invention are described in five sections. The first section, "General Description," describes various discoveries and concepts with respect to physical parameters and mechanisms for use in the devices including a discussion of buffers. The second section, "Design and Fabrication of the Basic Devices," describes the design of the basic underlying microelectronic device and the fabrication of devices using both microlithographic and micromachining techniques. The third section, "Self-Directed Addressing of the Devices," describes the self-addressing and self-assembly of the device, specifically the rapid transport and attachment of specific binding entities to each microlocation. The fourth section, "Applications of the Devices," describes how the device provides electronic control of various multi-step, combinatorial, and multiplex reactions. This section also describes the various uses and applications of the device. The fifth section describes various examples of the various inventive aspects disclosed here.

Electrophoretic Action

The devices (referred to as APEX device, microchips, DNA chips, micromachined devices, sample prep devices, electronic dot blots, etc.) and methods of this invention involve the application of DC, and also DC/AC electric fields to effect the transport, to accelerate the reactivity, and to improve the specificity of charged reagent and analyte molecules and entities (DNA, RNA, proteins, cells, etc.). Thus, a basic understanding and definition of the physical parameters concerning the effects of electric fields on charged molecules, of electrophoretic transport, and the properties of different buffering agents and electrolytes (anions and cations) are important to this invention. Of particular importance to the invention are the physical effects and phenomena which occur around the microlocation or permeation layer test sites near to where the electric fields emanate and/or the current densities are highest.

There are a number of physical parameters which relate to the electrophoretic transport of DNA and other charged analytes in various types of electrolyte and buffer solutions. The devices of this invention are basically DC (direct current) electrical devices which generate electric fields on the surface of the device, and produce a net current flow through the solution. Additionally, a number of low frequency (~0.1 to 500 Hz) DC and DC/AC low frequency pulsing scenarios (which still produce a net current flow) improve overall device performance, reagent and analyte concentration rates, DNA/RNA hybridization rates and efficiency, and the hybridization specificity. Also, using the systems and devices of this invention with special combinations of high frequency AC electric fields for cell selection and positioning, and DC electric fields for electrophoretic transport are disclosed for operations on integrated devices (sample preparation, etc.). High frequency (kHZ to MHz) AC fields, which produce no net current flow, do not produce electrophoretic transport of charged molecules in solution. However, these high frequency AC fields, which produce a field gradient, can cause cells and other entities with different dielectric properties to align along the field gradient lines. This process is called dielectrophoresis.

Definitions—With respect to DC fields (at voltages greater than ~1.0 to 1.2 volts) and pulsed DC and DC/AC fields, these electric fields do cause the electrophoretic transport of charged molecules to occur between oppositely (+/−) biased microlocations or test locations on the device surface. Under these conditions the devices produce significant net direct current flow when a voltages greater than about 1.0 to 1.2 volts are applied. This production of current is considered "the signature of the electrophoretic process". In this process, the migration of ions or charged particles is produced by electrical forces along the direction of the electric field gradient, and the relationship of current and voltage are important to this process. The electrophoretic migration shows itself macroscopically as the conduction of electric current in a solution under the influence of an applied voltage and follows Ohm's law:

$$V = R \times I$$

where:

V is the electric potential (voltage)

R is the electric resistance of the electrolyte $[V \times A^{-1} = \Omega]$

I is the electric current [Ampere]

The resistance (R) of the solution is the reciprocal of the conductance (L) which can be measured by a conductometer. The conductance depends on the geometry of the measuring device, and on the ionic species of the buffer/electrolytes and their concentration. While broadly these same current/voltage relationships which form the basis for the electrophoresis techniques used in molecular biology research apply, the electric fields produced by the devices of this invention are in many cases in truly microscopic environments, and the molecules being affected by these electric fields are sometime close to the origin (~1 to 2 microns) of the electric field. Additionally, the electrolyte anions and cations ($Na^+$, $K^+$, $Cl^-$, etc.), the buffering agents (phosphate, citrate, tris, histidine, cysteine, etc.), and the analyte molecules (DNA, RNA, proteins, cells, etc.) at the microlocation test sites experience very high current densities during applications of the electric field.

In one aspect of this invention, this high current density appears to be an important property which can be utilized for the "electronic de-hybridization" of complementary and partially complementary DNA sequences (including single base differences) from the DNA sequences attached or tethered to the microlocation/permeation layer test site. This is the key mechanism for the process called "electronic stringency". The second electronic stringency mechanism is the more basic property of electrophoretically transporting un-bound or non- specifically bound materials away from the microlocation test site. Finally, it should be pointed out that the devices and methods of this invention utilize the property of "electrophoretic transport", as opposed to technique of "electrophoresis", which is more properly defined as the use of an electric field to cause the separation of charged molecules through a sieving media.

In some aspects, the devices of this invention can be considered "microelectronic engines" to move or transport charged analytes and reagents from one microlocation to another microlocation on the device surface. In another aspect, the devices of this invention can produce high local current densities which can be used to control, influenence, affect, and improve the hybridization and de-hybridization processes occurring on the microlocation test sites.

There are unique features of the systems, devices, and methods of this invention which relate to the various ways of sourcing the current and voltage, and how various current and voltage scenarios are used to improve the performance of the systems. For example, an almost unlimited number of DC and DC/AC pulsing procedures (linear and logarithmic gradients)are possible which appear to provide significant improvements in reagent and analyte transport and concentration, DNA hybridization rates, DNA hybridization efficiencies, and DNA hybridization specificity or stringency. In many cases, these electronic pulsing procedures DC and DC/AC can be used to reduce or eliminate the adverse effects of the electrochemical products (including $H^+, OH^-, H_2, O_2$, free radicals, etc.) produced by the electrolysis reactions occurring on the "microelectrode" surfaces.

1.1.1 Electrophoretic Transport Versus Ionic Strength

It is well established in the field of electrophoresis that there is a logarithmic decrease in the mobility of the charged analyte species (proteins, DNA, etc.), which is inversely proportional to the square root of the ionic strength of the electrolyte solution (see page 83 and FIG. 3.16 in "Capillary Electrophoresis: Principles and Practice", R. Kuhn and S. Hoffstetter, Springer-Verlag, 1993). At any given constant electric field strength, as the electrolyte concentration decreases relative to the analyte species (protein, DNA, etc.), the analyte will be transported at a faster rate. Similar results demonstrating this effect for a danyslated amino acid have been shown by J. J. Issaq et. al., Chromatographia Vol. 32, #3/4, August 1991, pages 155 to 161 (see in particular FIG. 3 on page 157). Results demonstrating this effect for DNA in different electrolyte solutions has been shown in P. D. Ross and R. L. Scruggs, Biopolymers Vol. 2, pages 231 to 236, 1964 (see in particular FIG. 1, page 232).

Ionic Strength/Conductance Relationship—For those non-buffering electrolytes (sodium chloride, potassium chloride, etc.) which involve completely dissociated anion and cation species in solution ($Na^+ < - - - > Cl^-$, $K^+ < - - - > Cl^-$, etc.), the ionic strength and conductance are equivalent, i.e., the conductance will usually be proportional to the ionic strength. For those buffering electrolytes (phosphate, acetate, citrate, succinate, etc.) which are in their dissociated states (example: $2 Na^+ < - - - > P_4^{2--}$), the ionic strength and conductance will usually be equivalent, i.e., conductance is proportional to the ionic strength. (A buffer has been defined as a chemical solution which is resistant to change in pH on the addition of acid or alkali. See., e.g., Dictionary of Biotechnology, Second Edition, James Coombs, Stockton Press. As stated there, "traditionally, buffers based on inorganic salts (phosphate, carbonate) and organic acid salts (acetate, citrate, succinate, glycine, maleate, barbiturates, etc.) were used in biological experiments.) For those buffering electrolytes [Good Buffers (MOPS, HEPES, TAPS, Tricine, Bicine), Amino Acid Buffers, Ampholytes, etc.] which can have a zwitterionic species (no net charge at their pI), the conductance will decrease by approximately a factor of 10 for every pH unit difference between the isoelectric point (pI) and the (pKa). For example, an amino acid in its zwitterionic state ($^-OOC$—$CH(R)$—$NH_3^+$) will have a conductance value which will be approximately 1000 fold lower than when the "amino acid moiety" has a full net positive charge ($HOOC$—$CH(R)$—$NH_2^+ < - - - > X^-$), or a full negative charge ($Y^+ < - - - > {}^-OOC$—$CH(R)$—$NH_2$). Thus, a formal negative or positive charge develops on the amino acid moiety as it moves away from its pI, and the conductivity and ionic strength will begin to correlate. However, when at or near the pI the conductance will be much lower than is expected for that given ionic strength or concentration. When used at or near their pI's, electrophoresis texts refer to the Good Buffers and amino acid buffers as having "low conductance's at high ionic strength or concentration" (see page 88 of Capillary Electrophoresis: Principles and Practice", R. Kuhn and S. Hoffstetter, Springer-Verlag, 1993). A commonly used electrophoresis buffer "Tris-Borate" actually has a significantly lower conductivity than would be expected from its ionic strength or concentration. This may be due to the "tris cation" and "borate anion" forming a relatively stable zwitterionic complex in solution. The conductivity of a 100 mM Tris-Borate solution was determined to be 694 $\mu S/cm$, which is approximately 20 times lower than would be expected from its ionic strength, and is roughly equivalent to a 5 mM sodium phosphate or sodium chloride solution. Table 1 shows conductivity measurements of a number of transport buffers.

TABLE 1

| Solution/ Buffer | Measure- ment 1 | Measure- ment 2 | Measure- ment 3 | Average/Std. Deviation |
|---|---|---|---|---|
| 10 mm $MgCl_2$ | 1.95 mS/cm | 2.02 mS/cm | 2.13 mS/cm | 2.03 +/− 0.09 mS/cm |
| 1 mM $MgCl_2$ | 174 $\mu S/cm$ | 208 $\mu S/cm$ | 177 $\mu S/cm$ | 186 +/− 18.8 $\mu S/cm$ |
| 0.1 mM $MgCl_2$ | 16.9 $\mu S/cm$ | 16.7 $\mu S/cm$ | 18.3 $\mu S/cm$ | 17.3 +/− 0.87 $\mu S/cm$ |
| 10 mM NaCl | 1.07 mS/cm | 1.10 mS/cm | 1.18 mS/cm | 1.12 +/− 0.057 mS/cm |
| 1 mM NaCl | 112 $\mu S/cm$ | 115 $\mu S/cm$ | 111 $\mu S/cm$ | 112.7 +/− 2.08 $\mu S/cm$ |
| 0.1 mM NaCl | 8.80 $\mu S/cm$ | 8.98 $\mu S/cm$ | 10.5 $\mu S/cm$ | 9.43 +/− 0.93 $\mu S/cm$ |
| 20 mM $NaPO_4$ | 2.90 mS/cm | 2.79 mS/cm | 3.00 mS/cm | 2.90 +/− 0.11 mS/cm |
| 10 mM $NaPO_4$ | 1.40 mS/cm | 1.44 mS/cm | 1.48 mS/cm | 1.44 +/− 0.04 mS/cm |
| 1 mM $NaPO_4$ | 122 $\mu S/cm$ | 128 $\mu S/cm$ | 136 $\mu S/cm$ | 128.7 +/− 7.0 $\mu S/cm$ |
| 50 mM TRIS | 3.50 mS/cm | 3.14 mS/cm | 3.40 mS/cm | 3.35 +/− 0.19 mS/cm |
| 10 mM TRIS | 572 $\mu S/cm$ | 562 $\mu S/cm$ | 583 $\mu S/cm$ | 572 +/− 10.5 $\mu S/cm$ |
| 250 mM HEPES | 141 $\mu S/cm$ | 144 $\mu S/cm$ | 158 $\mu S/cm$ | 147.6 +/− 9.07 $\mu S/cm$ |
| 25 mM HEPES | 9.16 $\mu S/cm$ | 9.44 $\mu S/cm$ | 10.5 $\mu S/cm$ | 9.7 +/− 0.71 $\mu S/cm$ |
| 3.3 mM NaCitrate | 964 $\mu S/cm$ | 964 $\mu S/cm$ | 1.03 mS/cm | 986 +/− 38.1 $\mu S/cm$ |
| 5 mM NaSuc- cinate | 1.05 mS/cm | 960 $\mu S/cm$ | 1.01 mS/cm | 1.01 +/− 0.045 mS/cm |
| 5 mM NaOxalate | 1.02 mS/cm | 1.03 mS/cm | 1.12 mS/cm | 1.06 +/− 0.055 mS/cm |
| 10 mM NaAcetate | 901 $\mu S/cm$ | 917 $\mu S/cm$ | 983 $\mu S/cm$ | 934 +/− 43.5 $\mu S/cm$ |

TABLE 1-continued

| Solution/ Buffer | Measurement 1 | Measurement 2 | Measurement 3 | Average/Std. Deviation |
|---|---|---|---|---|
| 250 mM Cysteine | 27.4 µS/cm | 17.3 µS/cm | 23.5 µS/cm | 22.7 +/− 5.09 µS/cm |
| Milli-Q water | <0.5 µS/cm | | | Detection limit of 0.1 cell too low |

Zwitterionic Buffers/Conductance/Transport Rate—Certain advantages exist regarding the rate or speed of electrophoretic transport of DNA when using Zwitterionic buffers (Good buffers, amino acid buffers), or the Tris-Borate buffer at or near their pI's, these are: 1) these buffers can be used at relatively high concentrations to increase buffering capacity; 2) their conductance's are significantly lower than other types of buffers at the same concentration, and 3) one gains the advantage of higher electrophoretic transport rates for the analyte of interest (DNA).

Zwitterionic Buffer Capacity at the Isoelectric Point (pI)—Amino acid buffers do have buffer capacity at their pI's. While a given amino acid may or may not have its "highest buffering capacity" at its pI, it will have some degree of buffering capacity. Buffer capacity decreases by a factor of 10 for every pH unit difference between the pI and the pKa; those amino acids with three ionizable groups (histidine, cysteine, lysine, glutamic acid, aspartic acid, etc.) generally have higher buffering capacities at their pI's than those amino acids with only two dissociation's (glycine, alanine, leucine, etc.). For example, histidine pI=7.47, lysine pI=9.74, and glutamic acid pI=3.22, all have relatively good buffering capacity at their pI's, relative to alanine or glycine which have relatively low buffering capacities at their pI's (see A. L. Lehninger, Biochemistry, 2ed, Worth Publishers, New York, 1975; in particular FIGS. 4–8 on page 79, and FIGS. 4–9 on page 80). Histidine has been proposed as a buffer for use in gel electrophoresis, see, e.g., U.S. Pat. No. 4,936,963, but hybridization is not performed in such systems. Cysteine is in a more intermediate position, with regard to buffering capacity. The pI of cysteine is 5.02, the pKa for the α carboxyl group is 1.71, the pKa for the sulfhydryl is 8.33, and the pKa for α amino group is 10.78. An acid/base titration curve of 250 mM cysteine, shows that cysteine has a better "buffering capacity" at ~pH 5 than a 20 mM sodium phosphate. In the pH 4 to 6 range, the buffering capacity of cysteine is significantly better than 20 mM sodium phosphate, particularly at the higher pH. However, in these pH ranges the conductance of the 250 mM cysteine solution is very low ~23 µS/cm, compared to 20 mM sodium phosphate which has a value of ~2.9 mS/cm, a factor of 100 times greater.

Several electrophoretic techniques developed over 20 years ago are based on the ability to separate proteins in zwitterionic buffers "at their pI's" these techniques are called Isoelectrophoresis, Isotachophoresis, and Electrofocusing (see chapters 3 and 4 in "Gel Electrophoresis of Proteins: A Practical Approach" Edited by B. D. Hames & D. Rickwood, IRL Press 1981). Various amino acid buffers and Good buffers were used for these applications, all at their pI's (see Table 2, page 168 of the above reference).

I. DESIGN AND FABRICATION OF THE BASIC DEVICES

In order for a device to carry out multi-step and multiplex reactions, its electronic components must be able to maintain active operation in aqueous solutions. To satisfy this requirement, each microlocation must have an underlying controllable and functioning DC mode micro-electrode. However, it is important for device performance, particularly sensitivity (signal to noise ratio), that binding and affinity reactions are not prevented by the electrolysis reactions occurring on the active DC electrode surfaces. In addition to the damaging effects incurred by any of the sensitive reagents and analytes (DNA, RNA, proteins, etc.) directly contacting the electrode surface, the electrodes produce electrolysis products which include acid ($H^+$), base ($OH^-$), hydrogen, oxygen, and various free radical species which can also damage the sensitive components. Other considerations for the design and fabrication of a device include, but are not limited to, materials compatibilities, nature of the specific binding entities and the subsequent reactants and analytes, and the number of microlocations.

By "a controllable and functioning DC mode micro-electrode" is meant a micro-electrode biased either positively or negatively, operating in a direct current mode (either continuous or pulse or DC/AC), which can in a controllable manner affect or cause the free field electrophoretic transport of charged specific binding entities, reactants, or analytes to or from any location on the device, or from the sample solution.

Within the scope of this invention, the free field electrophoretic "transport" of molecules is not actually dependent on the electric field produced being bounded or confined by an insulating material. Conventional electrophoretic separation technologies require confinement or enclosure of electric field lines by insulating (non-conducting) materials. In the case of free field electrophoretic transport, charged molecules are moved from one microlocation to any other microlocation, or from the bulk solution to specific microlocations. Therefore, special arrangements or confinement by insulating materials is not required for this aspect of the invention. However, the confined region of the microlocation test site allows high current densities to be produced, which are necessary to achieve the appropriate electronic stringency for de-hybridization; and also provides a focal point for concentration of target DNA sequences from the bulk solution. A device can be designed to have as few as two addressable microlocations or as many as hundreds of thousands of microlocations. In general, a complex device with a large number of microlocations is fabricated using microlithography techniques or combination of microfabrication and micromachining. Fabrication is carried out on silicon or other suitable substrate materials, such as glass, silicon dioxide, plastic, insulated metallic or ceramic materials.

These microelectronic "chip" designs would be considered large scale array or multiplex analysis devices. A device with a small number of microlocations or macrolocations might be fabricated using micromachining techniques.

Addressable microlocations can be of any shape, preferably round, square, or rectangular. The size of an addressable microlocation can be of any size, preferably range from sub-micron (~0.5 µm) to several centimeters (cm), with 5 µm to 100 µm being the most preferred size range for devices fabricated using microlithographic techniques, and 100 µm to 10 millimeters being the most preferred size range for devices fabricated using the micromachining techniques. To make microlocations smaller than the resolution of microlithographic methods would require techniques such as electron beam lithography, ion beam lithography, or molecular beam epitaxy. While microscopic locations are desirable for analytical and diagnostic type applications, larger addressable locations or macrolocations (e.g., larger than 5 mm) are desirable for applications such as, but not limited to, preparative scale biopolymer synthesis, sample preparation, electronically dispensing of reagents.

After microlocations have been created by using microlithographic and/or micromachining techniques, chemical modification, polymerization, spin coating or even further microlithographic fabrication techniques are used to create the specialized attachment and permeation layers. These important layers separate the binding entities from the metal surface of the electrode. These important structures allow the DC mode micro-electrodes under the surface of each microlocation to: (1) affect or cause the free field electrophoretic transport of specific (charged) binding entities from the surface of one microlocation to the surface of another microlocation, or from the bulk solution to specific microlocations; (2) concentrate and covalently attach the specific binding entities to the specially modified surface of the specific microlocation; (3) continue to actively function in the DC mode after the attachment of specific binding entities so that other reactants and analytes can be transported in a controlled manner to or from the microlocations; (4) not adversely affect the binding or affinity reactions with electrochemical reactions and products.

I(a). DESIGN PARAMETERS (MICROLITHOGRAPHY)

FIG. 1 shows a basic design of self-addressable microlocations fabricated using microlithographic techniques. The three microlocations (10) (ML-1, ML-2, ML-3) are formed on the surface of metal sites (10) which have been deposited on an insulator layer/base material. The metal sites (10) serve as the underlying micro-electrode structures (10). Electrode materials can include but are not limited to: aluminum, copper, carbon, iron, silver, gold, palladium, palatinum, and indium tin oxide. An insulator material separates the metal sites (10) from each other. Insulator materials include, but are not limited to, silicon dioxide, silicon nitride, glass, resist, polyimide, rubber, plastic, or ceramic materials.

FIG. 2 shows the basic features of an individual microlocation (10) formed on a microlithographically produced metal site (10). The addressable microlocation is formed on the metal site (10), and incorporates an oxidation layer (utilized in the case of aluminum or other metals which readily produce oxides)(20), a permeation layer (22), an attachment layer (24), and a binding entity layer (26).

In the case of metals like aluminum, the metal oxide layer provides a base for the covalent coupling of the permeation layer. Metal oxide and hydroxyl groups (either alone or in combination), and other materials known to those skilled in the art of surface coating chemistries may provide covalent sites from which to construct or hold the permeations layer. It is not absolutely essential that the permeation layer actually be covalently attached to the metal electrode surface. The physical overlaying of permeable materials represents an alternative method which is within the scope of this invention. In the case of metals like platinum and gold, a permeation layer can be physically overlayed.

The permeation layer provides spacing between the metal surface and the attachment/binding entity layers and allows solvent molecules, small counter-ions, and electrolysis reaction gases to freely pass to and from the metal surface. It is possible to include within the permeation layer substances which can reduce the adverse physical and chemical effects of electrolysis reactions, including, but not limited to, redox reaction trapping substances, such as palladium for $H_2$, and iron complexes for $O_2$ and peroxides. Additionally, the permeation layer can contain compounds or materials which help maintain the stability of the DNA hybrids; these can include but are not limited to histidine, histidine peptides, polyhistidine, lysine, lysine peptides, and other cationic compounds or substances. The thickness of the permeation layer for microlithographically produced devices can range from approximately 1 nanometers (nm) to 100 microns ($\mu$m), with 2 nm to 10 $\mu$m being the most preferred. Permeation layer materials can include but are not limited to: metal oxides, membranes, agarose, polyacrylamides, hydrogels, sol-gels, aero-gels, porous glass, porous silicon, cross linked polymers, etc.

The attachment layer provides a base for the covalent binding of the binding entities. The thickness of the attachment layer for microlithographically produced devices can range from 0.5 nm to 5 $\mu$m, with 1 nm to 500 nm being the most preferred. In some cases, the permeation and attachment layers can be formed from the same material. Certain permeation layer materials which can be further activated for the coupling of binding entities are included within the scope of this invention.

The specific binding entities are covalently or affinity coupled to the attachment layer, and form the specific binding entity layer. For example, streptavidin can be incorporated into the permeation layer, providing an affinity binding site for DNA probes which have been derivatized with biotin. Ideally, the specific binding entity layer is usually a mono-layer of the specific binding molecules. However, in some cases the binding entity layer can have several or even many layers of binding molecules.

Certain design and functional aspects of the permeation and attachment layer are dictated by the physical (e.g., size and shape) and chemical properties of the specific binding entity molecules. They are also dictated to some extent by the physical and chemical properties of the reactant and analyte molecules, which will be subsequently transported and bound to the microlocations. For example, oligonucleotide binding entities can be attached to one type of microlocation surface without causing a loss of the DC mode function, i.e., the underlying micro-electrode can still cause the rapid free field electrophoretic transport of other analyte molecules to or from the surface to which the oligonucleotide binding entities are attached. However, if large globular protein binding entities (e.g., antibodies) are attached to the same type of surface, they might insulate the surface and cause a decrease or a complete loss of the DC mode function. Appropriate modification of the attachment layer would have to be carried out so as to either reduce the number of large binding entities (e.g., large globular proteins) or provide spacing between the binding entities on the surface.

The spacing between microlocations is determined by the ease of fabrication, the requirement for detector resolution between microlocations, and the number of microlocations desired on a device. However, particular spacings between microlocations, or spacial arrangement or geometry of the microlocations is not necessary for device function, in that any combination of microlocations (i.e., underlying microelectrodes) can operate over the complete device area. Nor is it actually necessary to enclose the device or completely confine the microlocations with dielectric or insulating barriers. This is because complex electronic field patterns or dielectric boundaries are not required to selectively move, separate, hold, or orient specific molecules in the space or medium between any of the electrodes. The device accomplishes this by attaching the specific binding molecules and subsequent analytes and reactants to the surface of an addressable microlocation. Free field electrophoretic propulsion provides for the rapid and direct transport of any charged molecule between any and all locations on the device; or from the bulk solution to microlocations. However, it should be pointed out that the devices might be enclosed for fluid containment and for bio-hazard purposes.

As the number of microlocations increases beyond several hundred, the complexity of the underlying circuitry of the microlocations increases. In this case the microlocation grouping patterns have to be changed and spacing distances increased proportionally, or multi-layer circuitry can be fabricated into the basic device, i.e., transistors and semiconductor control elements incorporated directly into the silicon.

In addition to microlocations which have been addressed with specific binding entities, a device will contain non-analytical microlocations and macrolocations which serve other functions. These microlocations or macrolocations can be used to store reagents, to temporarily hold reactants, analytes, or cells; and as disposal units for excess reactants, analytes, or other interfering components in samples (i.e., reagent dispensing and sample preparation systems). Other un-addressed microlocations can be used in combination with the addressed microlocations to affect or influence the reactions that are occurring at these specific microlocations. These microlocations add to both inter-device and intra-device activity and control. For example, a perimeter of microlocations (with underlying microelectrodes) surrounding an array of test site microlocations could be used as counter electrodes to encompass a large volume of test solution. Also, it is also possible for the microlocations to interact and transport molecules between two separate devices. This provides a mechanism for loading a working device with binding entities or reactants from a storage device, for sample preparations and for copying or replicating a device.

FIG. 3 shows a matrix type device containing 64 addressable microlocations (30). A 64 microlocation device is a convenient design, which fits with standard microelectronic chip packaging components. Such a device is fabricated on a silicon chip substrate approximately 1.5 cm×1.5 cm, with a central area approximately 750 $\mu$m×750 $\mu$m containing the 64 microlocations. Each microlocation (32) is approximately 50 $\mu$m square with 50 $\mu$m spacing between neighboring microlocations. Connective circuitry for each individual underlying micro-electrode runs to an outside perimeter (10 mm×10 mm) of metal contact pads (300 $\mu$m square) (34). A raised inner perimeter can be formed between the area with the microlocations and the contact pads, producing a cavity which can hold approximately 2 to 10 microliters ($\mu$l) of a sample solution. The "chip" can be mounted in a standard quad package, and the chip contact pads (34) wired to the quad package pins. Systems containing more than one chip and additional packaging and peripheral components may be designed to address problems related to clinical diagnostics, i.e., addition of sample materials, fluid transfer, and containment of bio-hazardous materials. The packaged chip can then be plugged into a microprocessor controlled DC power supply and multimeter apparatus which can control and operate the device. It is contemplated by this invention that device manufacture (prior to addressing) will ultimately involve the incorporation of three basic components which would be essentially sandwiched together. The basic chip device to which the binding entities are attached, would be in the middle position; a sample or fluid containment component, would be annealed over the top and on board controller component would be annealed to the bottom of the basic chip device. This strategy solves a number of problems related to fabrication techniques and materials compatibilities.

I(b). MICROLITHOGRAPHY FABRICATION PROCEDURES

I(b)(1) Fabrication Steps General microlithographic or photolithographic techniques can be used for the fabrication of the complex "chip" type device which has a large number of small microlocations. While the fabrication of devices does not require complex photolithography, the selection of materials and the requirement that an electronic device function actively in aqueous solutions does require special considerations.

The 64 microlocation device (30) shown in FIG. 3 can be fabricated using relatively simple mask design and standard microlithographic techniques. Generally, the base substrate material would be a 1 to 2 centimeter square silicon wafer or a chip approximately 0.5 millimeter in thickness. The silicon chip is first overcoated with a 1 to 2 $\mu$m thick silicon dioxide ($SiO_2$) insulation coat, which is applied by plasma enhanced chemical vapor deposition (PECVD).

In the next step, a 0.2 to 0.5 $\mu$m metal layer (e.g., aluminum) is deposited by vacuum evaporation. It is also possible to deposit metals by sputtering techniques.

In addition to aluminum, suitable metals and materials for circuitry include gold, silver, tin, titanium, copper, platinum, palladium, polysilicon, carbon, and various metal combinations. Special techniques for ensuring proper adhesion to the insulating substrate materials ($SiO_2$) are used with different metals. Different metals and other materials may be used for different conductive components of the device, for example, using aluminum for the perimeter contact pads, polysilicon for the interconnect circuitry, and a noble metal (gold or platinum) for the micro-electrodes.

The chip is next overcoated with a positive photoresist (Shipley, Microposit AZ 1350 J), masked (light field) with the circuitry pattern, exposed and developed. The photo-solubilized resist is removed, and the exposed aluminum is etched away. The resist island is now removed, leaving the aluminum circuitry pattern on the chip. This includes an outside perimeter of metal contact pads, the connective circuitry (wires), and the center array of micro-electrodes which serve as the underlying base for the addressable microlocations.

Using PECVD, the chip is overcoated first with a 0.2 to 0.4 micron layer of $SiO_2$, and then with a 0.1 to 0.2 micron layer of silicon nitride ($Si_3N_4$). The chip is then covered with positive photoresist, masked for the contact pads and micro-electrode locations, exposed, and developed. Photosolubilized resist is removed, and the $SiO_2$ and $Si_3N_4$ layers are etched away to expose the aluminum contact pads and micro-electrodes. The surrounding island resist is then removed, the connective wiring between the contact pads and the micro-electrodes remains insulated by the $SiO_2$ and $Si_3N_4$ layers.

The $SiO_2$ and $Si_3N_4$ layers provide important properties for the functioning of the device. The second $SiO_2$ layer provides better contact and improved sealing with the aluminum circuitry. It is also possible to use resist materials to insulate and seal. This prevents undermining of the circuitry due to electrolysis effects when the micro-electrodes are operating. The final surface layer coating of $Si_3N_4$ is used because it has much less reactivity with the subsequent reagents used to modify the micro-electrode surfaces for the attachment of specific binding entities.

I(b)(2) Permeation and Attachment Layer Formation Steps

At this point the micro-electrode locations on the device are ready to be modified with a specialized permeation and attachment layer. This is an important aspect of the invention. The objective is to create on the micro-electrode an intermediate permeation layer with selective diffusion properties and an attachment surface layer with optimal binding properties.

Optimally, the attachment layer has from $10^5$ to $10^7$ functionalized locations per square micron ($\mu m^2$) for the attachment of specific binding entities. The attachment of specific binding entities should not overcoat or insulate the surface so as to prevent the underlying micro-electrode from functioning. A functional device requires some fraction (~5% to 25%) of the actual metal micro-electrode surface to remain accessible to solvent ($H_2O$) molecules, and to allow the diffusion of counter-ions (e.g., $Na^+$ and $Cl^-$) and electrolysis gases (e.g., $O_2$ and $H_2$) to occur.

The intermediate permeation layer is also designed to allow diffusion to occur. Additionally, the permeation layer should have a pore limit property which inhibits or impedes the larger binding entities, reactants, and analytes from physical contact with the micro-electrode surface. The permeation layer keeps the active micro-electrode surface physically distinct from the binding entity layer of the microlocation.

This design allows the electrolysis reactions required for electrophoretic transport to occur on micro-electrode surface, but avoids adverse electrochemical effects to the binding entities, reactants, and analytes.

The permeation layer can also be designed to include substances which scavenge adverse materials produced in the electrolysis reactions (H2, O2, free radicals, etc.). A sub-layer of the permeation layer may be designed for this purpose.

A variety of designs and techniques can be used to produce the permeation layer. The general designs include: (1) "Lawns", (2) "Meshes", and (3) "Porous" structures.

Lawn type permeation layers involve the arrangement of linear molecules or polymers in a vertical direction from the metal surface, in a way resembling a thick lawn of grass. These structures can be formed by attaching linear or polymeric hydrophilic molecules directly to the metal surface, with minimum cross linkages between the vertical structures. Ideally these hydrophilic linear molecules are bifinctional, with one terminal end suited for covalent attachment to the metal pad, and the other terminal end suited for covalent attachment of binding entities.

Mesh type permeation layers involve random arrangements of polymeric molecules which form mesh like structures having an average pore size determined by the extent of cross-linking. These structures can be formed by hydrogel type materials such as, but not limited to polyacrylamide, agarose, and a variety of other biological and non-biological materials which can be polymerized and cross-linked. These materials can be spin coated over the array surface.

Pore type permeation layers involve the use of materials which can form a channel or hole directly from the top surface of the layer to the metal pad, including, but not limited to, polycarbonates, polysulfone, or glass materials. In all cases the permeation layer must be secured either physically or chemically to the metal surface, and must contain functional groups or be capable of being functionalized for the attachment of binding entities to its surface.

One preferred procedure which produces a lawn type structure involves the derivatization of the metal micro-electrode surface uses aminopropyltriethoxy silane (APS). APS reacts readily with the oxide and/or hydroxyl groups on metal and silicon surfaces. APS provides a combined permeation layer and attachment layer, with primary amine groups for the subsequent covalent coupling of binding entities. In terms of surface binding sites, APS produces a relatively high level of functionalization (i.e., a large number of primary amine groups) on slightly oxidized aluminum surfaces, an intermediate level of functionalization on $SiO_2$ surfaces, and very limited functionalization of $Si_3N_4$ surfaces.

The APS reaction is carried out by treating the whole device (e.g., a chip) surface for 30 minutes with a 10% solution of APS in toluene at 50° C. The chip is then washed in toluene, ethanol, and then dried for one hour at 50° C. The micro-electrode metal surface is functionalized with a large number of primary amine groups ($10^5$ to $10^6$ per square micron). Binding entities can now be covalently bound to the derivatized micro-electrode surface. The depth of this "Lawn Type" permeation layer may be increased by using polyoxyethylene bis(amine), bis(polyoxyethylene bis (amine)), and other polyethylene glycols or similar compounds.

Figure 4:
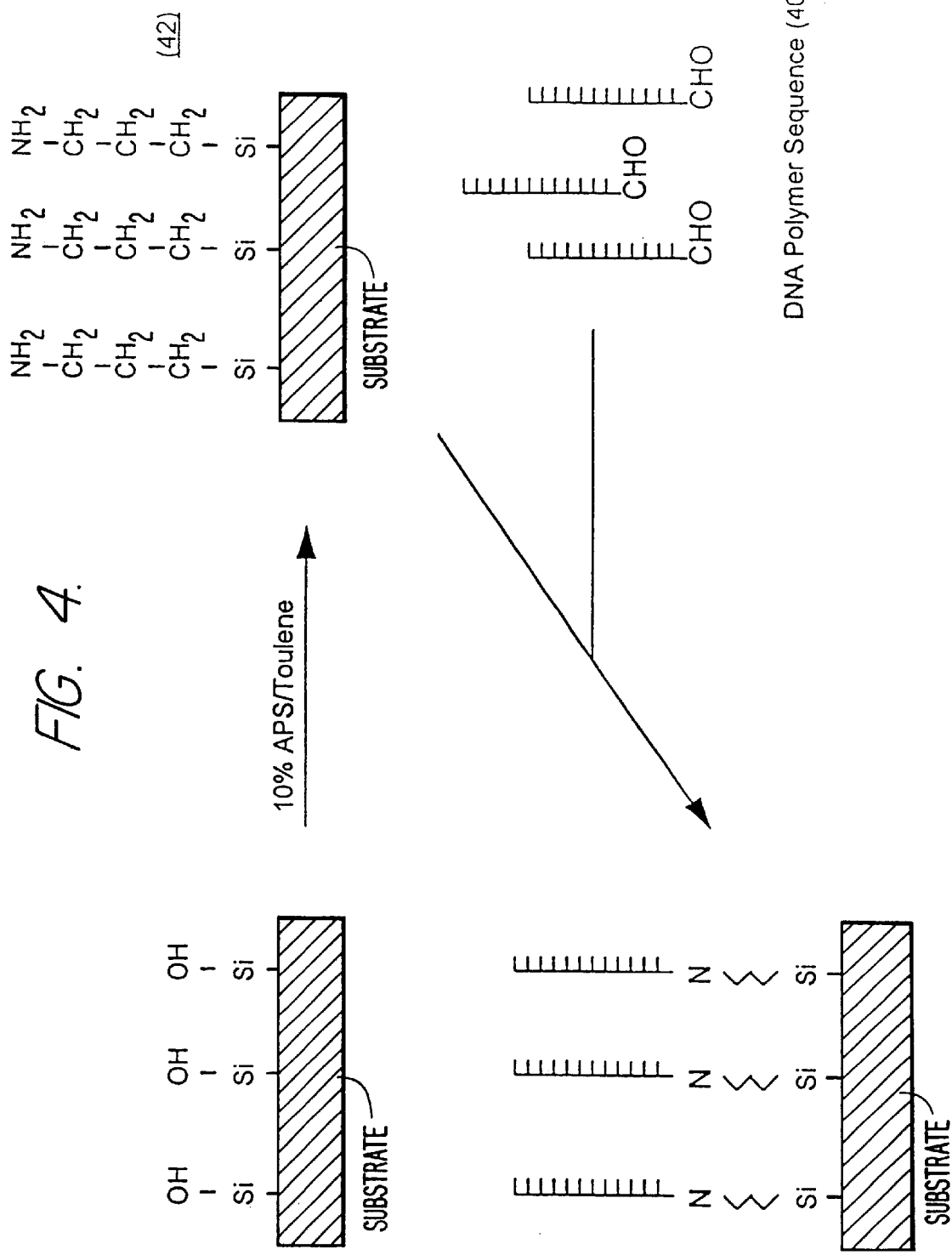
FIG. 4 shows particular attachment chemistry procedure which allows rapid covalent coupling of specific oligonucleotides to the attachment surface of a microlocation.

The APS procedure works well for the attachment of oligonucleotide binding entities. FIG. 4 shows the mechanism for the attachment of 3'-terminal aldehyde derivatized oligonucleotides (40) to an APS functionalized surface (42). While this represents one of the approaches, a variety of other approaches for forming permeation and attachment layers are possible. These include the use of self-direct addressing by the base electrode itself to: (1) form secondary metal layers by electroplating to the base micro-electrode; (2) to form permeation layers by electropolymerization to the micro-electrode location, or (3) to transport by the free field electrophoresis process activated polymers and reagents to the micro-electrode surface to form subsequent permeation and attachment layers, or (4) Permeation layers can be produced by spin coating the materials (hydrogels, agarose, acrylamides, etc.) on to the surface of the array.

MICRO-MACHINED DEVICE DESIGN AND FABRICATION

This section describes how to use micro-machining techniques (e.g., drilling, milling, etc.) or non-lithographic techniques to fabricate devices. In general, these devices have relatively larger microlocations (>100 microns) than those produced by microlithography. These devices can be used for analytical applications, as well as for preparative type applications, such as biopolymer synthesis, sample preparation, reagent dispenser, storage locations, and waste disposal. Large addressable locations can be fabricated in three dimensional formats (e.g., tubes or cylinders) in order to carry a large amount of binding entities. Such devices can be fabricated using a variety of materials, including, but not limited to, plastic, rubber, silicon, glass (e.g., microchannelled, microcapillary, etc.), or ceramics. Low fluorescent materials are more ideal for analytical applications. In the case of micro-machined devices, connective circuitry and larger electrode structures can be printed onto materials using standard circuit board printing techniques known to those skilled in the art.

Figure 5:
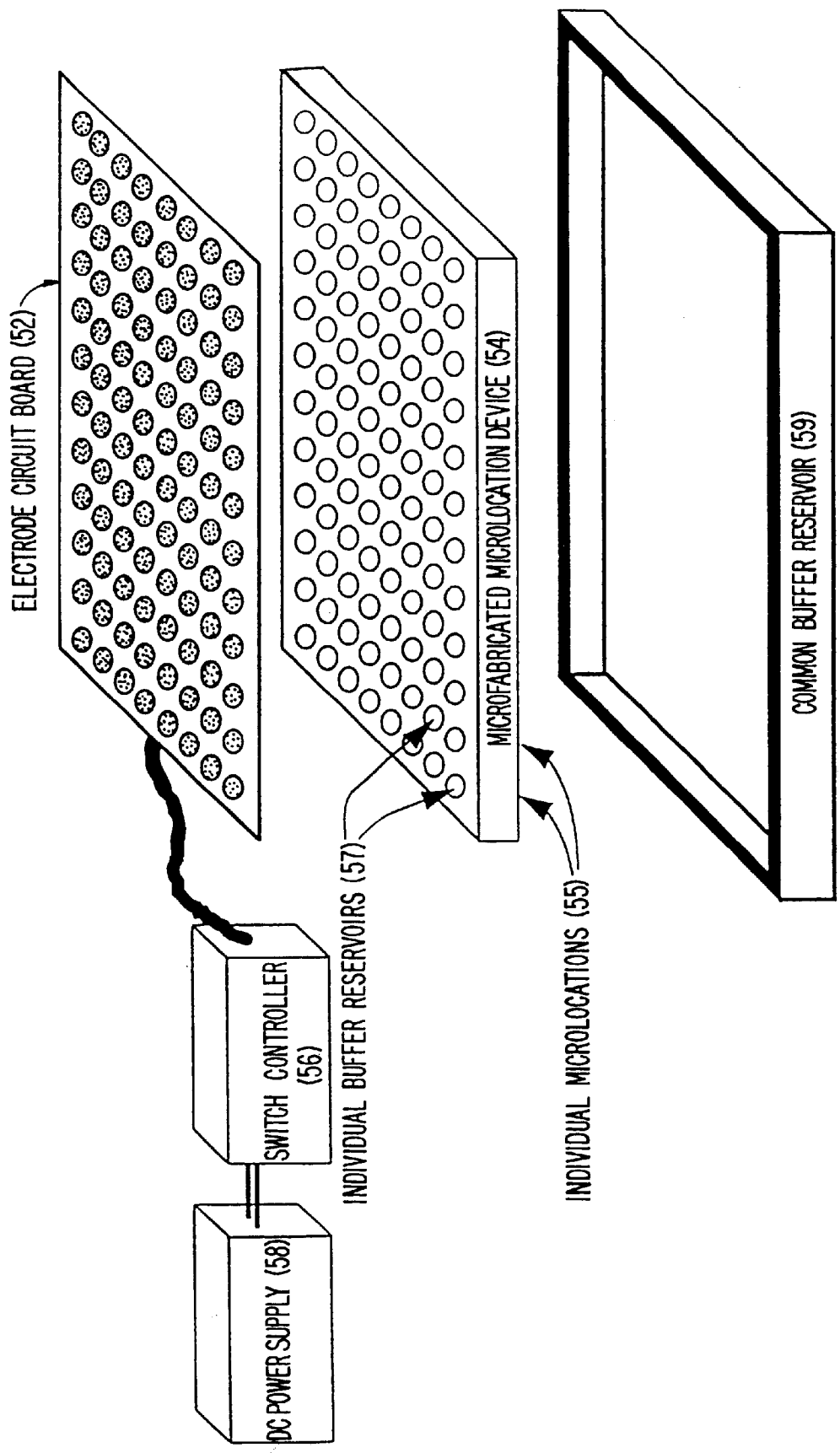
FIG. 5 is a blown-up schematic diagram of a micromachined 96 microlocations device.
Figure 6:
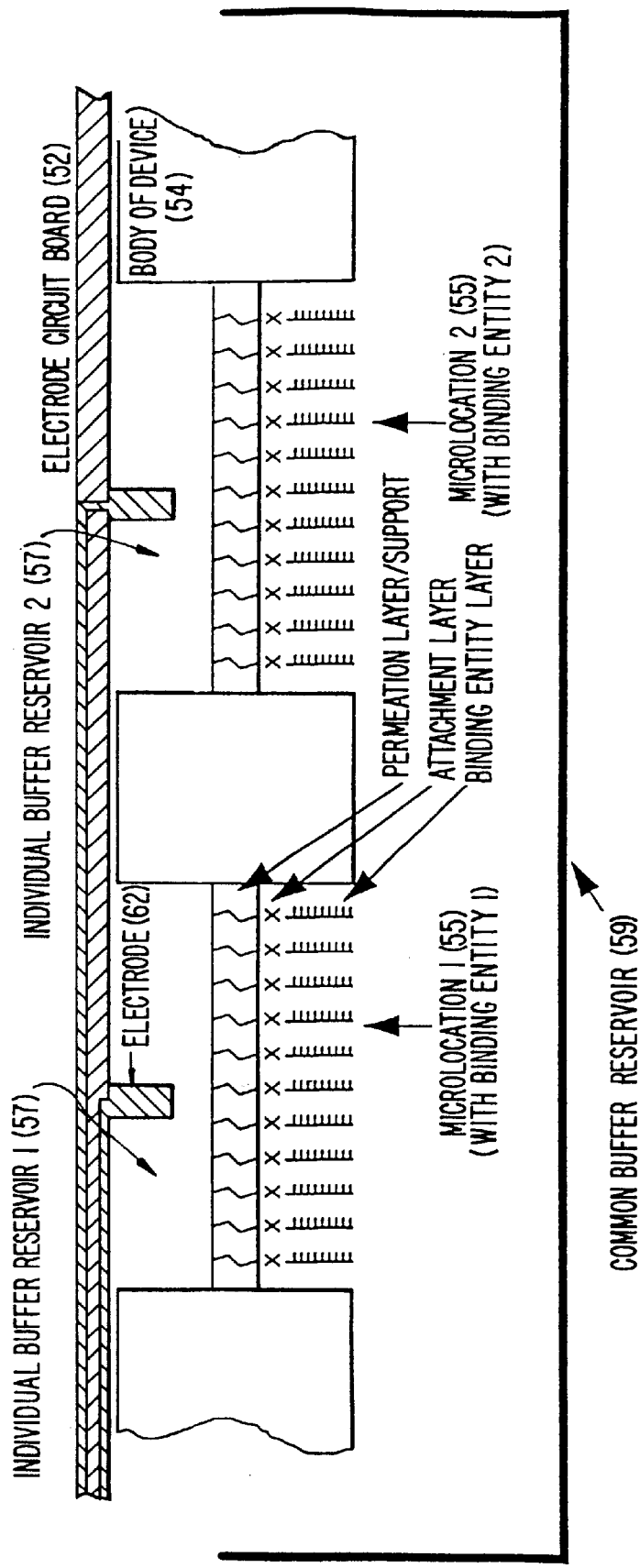
FIG. 6 is the cross-section of a micro-machined device.

Addressable microlocation devices can be fabricated relatively easily using micro-machining techniques. FIG. 5 is a schematic of a representative 96 microlocation device. This microlocation device is fabricated from a suitable material stock (2 cm×4 cm×1 cm), by drilling 96 proportionately spaced holes (1 mm in diameter) through the material. An electrode circuit board (52) is formed on a thin sheet of plastic material stock, which fits precisely over the top of the microlocation component (54). The underside of the circuit board contains the individual wires (printed circuit) to each microlocation (55). Short platinum electrode structures (~3–4 mm) (62) are designed to extend down into the individual microlocation chamber s (57). The printed circuit wiring is coated with a suitable water-proof insulating material. The printed circuit wiring converges to a socket, which allows connection to a multiplex switch controller (56) and DC power supply (58). The device is partially immersed and operates in a common buffer reservoir (59).

While the primary function of the microlocations in devices fabricated by micro-machining and microlithography techniques is the same, their designs may be different. In devices fabricated by microlithography, the permeation and attachment layers are formed directly on the underlying metal micro-electrode. In devices fabricated by micro-machining techniques, the permeation and attachment layers can be physically separated from their individual metal electrode structure (62) by a buffer solution in the individual chamber or reservoir (57) (see FIG. 6). In micro-machined devices the permeation and attachment layers can be formed using functionalized hydrophilic gels, membranes, or other suitable porous materials.

In general, the thickness of the combined permeation and attachment layers ranges from 10 μm to 30 mm. For example, a modified hydrophilic gel of 20% to 35% polyacrylamide (with 0.1% polylysine), can be used to partially fill (~0.5 mm) each of the individual microlocation chambers in the device. These concentrations of gel form an ideal permeation layer with a pore limit of from 2 nm to 10 nm. The polylysine incorporated into the gel provides primary amine functional groups for the subsequent attachment of specific binding entities. This type of gel permeation layer allows the electrodes to function actively in the DC mode. When the electrode is activated, the gel permeation layer allows small counterions to pass through it, but the larger specific binding entity molecules are concentrated on the outer surface. Here they become covalently bonded to the outer layer of primary amines, which effectively becomes the attachment layer.

An alternative technique for the formation of the permeation and attachment layers is to incorporate into the base of each microlocation chamber a porous membrane material. The outer surface of the membrane is then derivatized with chemical functional groups to form the attachment layer. Appropriate techniques and materials for carrying out this approach are known to those skilled in the art.

The above descriptions for the design and fabrication of both the microlithographic and micromachined devices should not be considered as a limit to other variations or forms of the basic device. Many variations of the device with larger or smaller numbers of addressable microlocations or combinations of devices can be for different analytical and preparative applications. Variations of the device with larger addressable locations can be designed for preparative biopolymer synthesis applications, sample preparation, cell sorting systems, in-situ hybridization, reagent dispensers, strong storage systems and waste disposal systems.

II. SELF-DIRECTED ADDRESSING OF THE DEVICES

The devices of this invention are able to electronically self-address each microlocation with a specific binding entity. The device itself directly affects or causes the transport of a charged specific binding entity to a specific microlocation. The binding entities are generally functionalized so that they readily react and covalently bond to the attachment layer. The device self-assembles itself in the sense that no outside process, mechanism, or equipment is needed to physically direct, position, or place a specific binding entity at a specific microlocation. This self-addressing process is both rapid and specific, and can be carried out in either a serial or parallel manner.

Figure 7A:
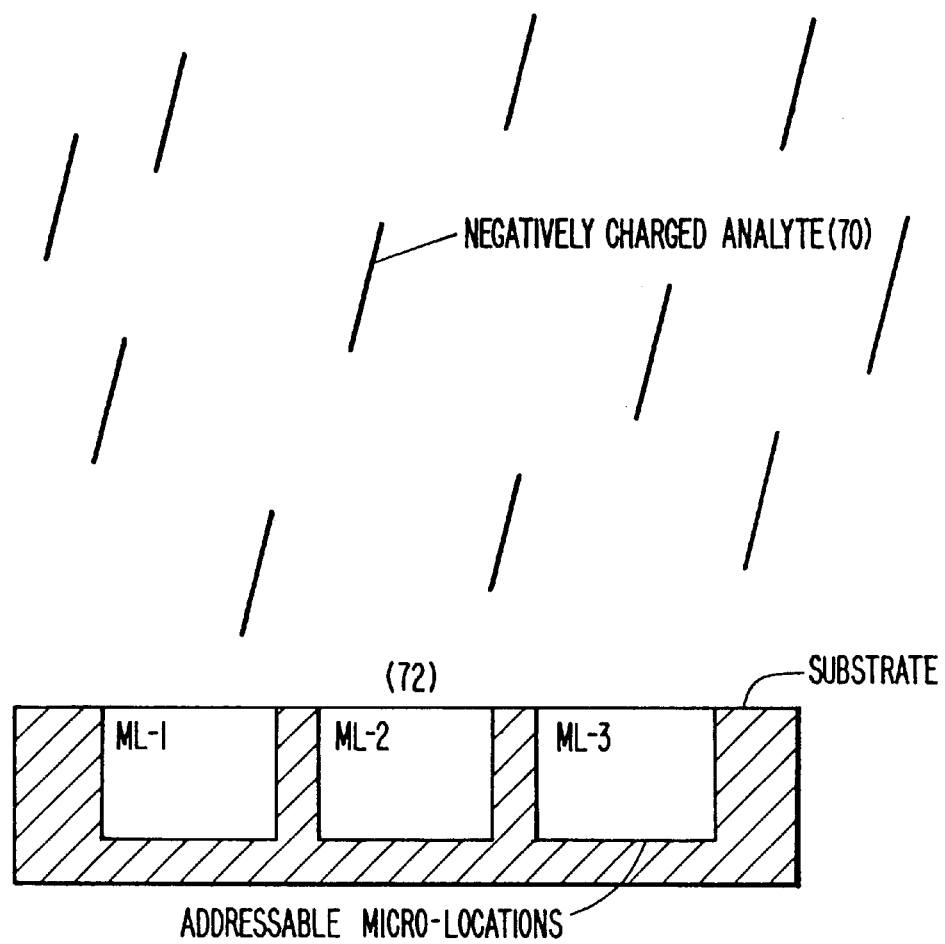
FIG. 7a and FIG. 7b show the mechanism the device uses to electronically concentrate analyte or reactant molecules at a specific microlocation, FIG. 7a showing the addressable microlocations in a neutral condition and FIG. 7b showing the addressable microlocations in a charged state.
Figure 7B:
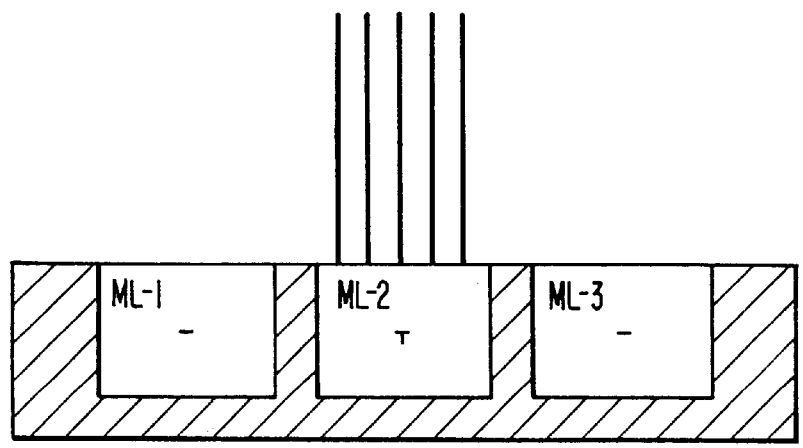
Figure 8A:
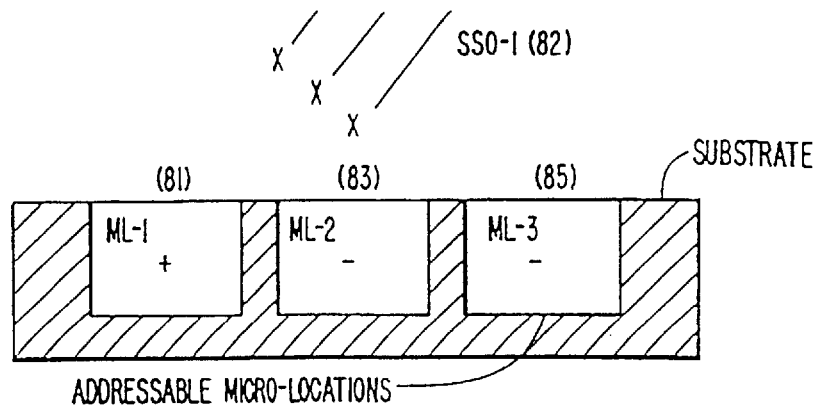
FIGS. 8a, 8b, 8c and 8d show the self-directed assembly of a device with three specific oligonucleotide binding entities (SSO-A, SSO-B, and SSO-C), FIG. 8a showing a first microlocation (ML-1) being addressed, FIG. 8b showing a second microlocation (ML-2) being addressed, FIG. 8c showing a third microlocation (ML-3) being addressed and FIG. 8d showing the three microlocations after being addressed and assembled.
Figure 8B:
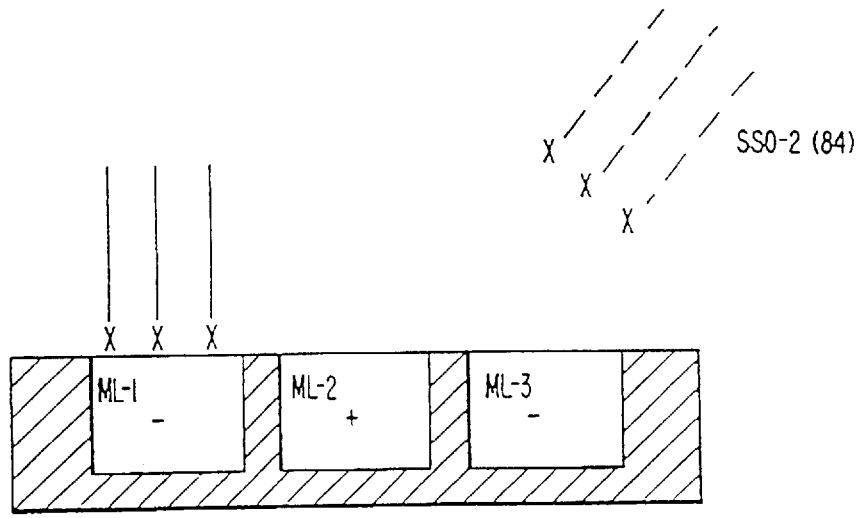
Figure 8C:
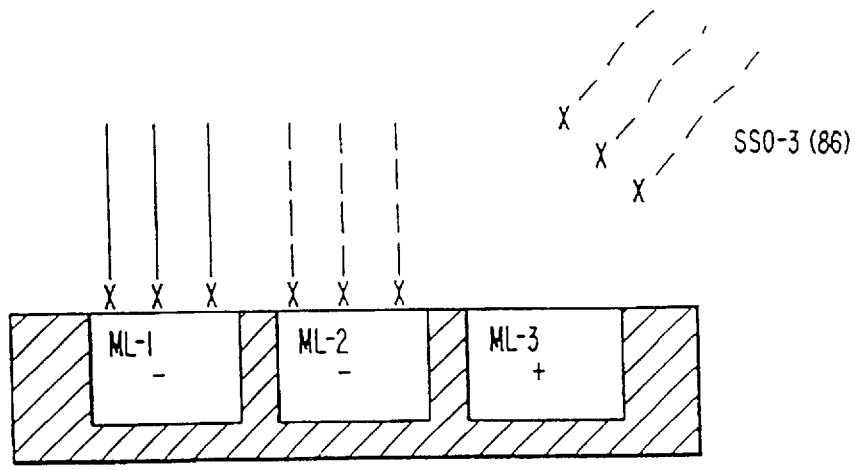
Figure 8D:
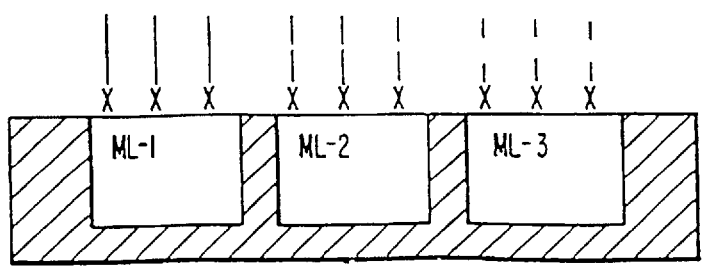

A device can be serially addressed with specific binding entities by maintaining the selected microlocation in a DC mode and at the opposite charge (potential) to that of a specific binding entity. If a binding entity has a net negative charge, then the microlocation to which the binding entity is to be transported would be biased positive. Conversely, a negatively charged microlocation would be used to transport a positively charged binding entity. Options for biasing the remaining microlocations in the serial addressing process include: biasing all other microlocations at the opposite charge (counter to the microlocations being addressed);

biasing a limited group of microlocations at the opposite charge; or biasing just one microlocation (or other electrode) at the opposite charge. In some cases, it will be desireable to strongly bias one or more microlocations at the opposite charge, while other groups of microlocations are biased only weakly. This process allows previously addressed microlocations to be protected during the addressing of the remaining microlocations. In cases where the binding entity is not in excess of the attachment sites on the microlocation, it may be necessary to activate only one other micro-electrode to affect the free field electrophoretic transport to the specific microlocation. Specific binding entities can be rapidly transported through the bulk solution, and concentrated directly at the specific microlocation(s) where they immediately becomes covalently bonded to the special surface of the attachment layer. Transportation rates are dependent on the size and charge of the binding entities, and the voltage and current levels used between the microlocations. In general, transportation rates can range from several seconds to several minutes. The ability to electronically concentrate binding entities, reactants or analytes (70) on a specific microlocation (72) is shown in FIGS. 7a and 7b. All other microlocations can be protected and remain unaffected during the specific binding entity addressing process. Any unreacted binding entity is removed by reversing the polarity of that specific microlocation, and electrophoresing it to a disposal location. The cycle is repeated until all desired microlocations are addressed with their specific binding entities. FIGS. 8a through 8d show the serial process for addressing specific microlocations (81, 83, 85) with specific oligonucleotide binding entities (82, 84, 86). A distinct advantage of this ability to self-address the devices, leads to the development of instrument system which allow addressing of an APEX chip device with any DNA or RNA probe, or any other ligand. Such a "make your own chip" instrument would contain a platform to hold or mount the chip or packaged chip component; provide electrical contact and control for controlling current an voltage to each location on the chip; provide a fluidic or electronic delivery system to provide probe sequences to the chip; and a microprocessor unit to control the whole system. Such a system would allow "make your own chip" products and applications. Such products and applications would be useful to many researchers and end users for clinical diagnostic, molecular biology, functional genomic and drug discovery applications.

The parallel process for addressing microlocations involves simultaneously activating more than one microlocation (a particular group) so that the same specific binding entity is transported, concentrated, and reacted with more than one specific microlocation. The subsequent parallel processing is similar to the serial process.

III. APPLICATIONS OF THE DEVICES

Once a device has been self-addressed with specific binding entities, a variety of molecular biology type multi-step and multiplex reactions and analyses can be carried out on the device. The devices of this invention are able to electronically provide active and dynamic control over a number of important reaction parameters. This electronic control leads to new physical mechanisms for controlling reactions, and significant improvements in reaction rates, specificities, and sensitivities. The improvements in these parameters come from the ability of the device to electronically control and directly affect: (1) the rapid transport of reactants or analytes to a specific microlocation containing attached specific binding entities; (2) an increase in reaction rate due to the concentration of reactants or analytes with the specific binding entities on the surface of the specific microlocation; (3) the rapid and selective removal of un-reacted and non-specifically bound components from the microlocation; and (4) the stringency for optimal binding conditions.

The self-addressed devices of this invention are able to rapidly carry out a variety of micro-formatted multi-step and/or multiplex reactions and procedures; which include, but are not limited to:

DNA and RNA hybridizations procedures and analysis in conventional formats; e.g., attached target DNA/probe DNA, attached probe DNA/target DNA, attached capture DNA/target DNA/probe DNA;

multiple or multiplexed hybridization reactions in both serial and parallel fashion;

restriction fragment and general DNA/RNA fragment size analysis; STR analysis; SNP analysis;

molecular biology reactions, e.g., restriction enzyme reactions and analysis, ligase reactions kinasing reactions, and DNA/RNA amplification;

antibody/antigen reactions involving large or small antigens and haptens;

diagnostic assays, e.g., hybridization analysis (including in-situ hybridization), gene analysis, DNA fingerprinting, forensic applications and immunodiagnostics;

sample preparation, cell sorting, selection, and analysis; gene expression analysis;

biomolecular conjugation procedures (i.e. the covalent and non-covalent labeling of nucleic acids, enzymes, proteins, or antibodies with reporter groups, including fluorescent, chemiluminescent, colorimetric, and radio-isotopic labels);

biopolymer synthesis, e.g., combinatorial synthesis of oligonucleotides or peptides;

water soluble synthetic polymer synthesis, e.g., carbohydrates or linear polyacrylates; and macromolecular and nanostructure (nanometer size particles and structures) synthesis and fabrication.

III(a) NUCLEIC ACID HYBRIDIZATION

Nucleic acid hybridizations are used as main examples of this invention because of their importance in diagnostics, and because they characterize one of the more difficult types of binding (affinity) reactions. This is particularity true when they are carried out in multiplex formats, where each individual hybridization reaction requires a different stringency condition.

The device and methods allow nucleic acid hybridization to be carried out in a variety of conventional and new formats. The ability of the device to electronically control reaction parameters greatly improves nucleic acid hybridization analysis, particularly the ability of the device to provide electronic stringency control (ESC) to each individual microlocation on an array. In essence, this allows each individual hybridization reaction on a common array to be carried out as a single test tube assay.

The term "nucleic acid hybridization" is meant to include hybridization reactions between all natural and synthetic forms and derivatives of nucleic acids, including: deoxyribonucleic acid (DNA), ribonucleic acid (RNA), polypucleotides and oligonucleotides, peptide nucleic acid; etc.

Conventional hybridization formats, such as "dot blot" hybridization and "sandwich" hybridization, can be carried out with the disclosed device as well as large scale array or matrix formats.

As an example, an APEX device for DNA hybridization analysis is designed, fabricated, and used in the following manner. Arrays of microlocations are first fabricated using microlithographic (or micromechining) techniques. The number of addressable microlocations on an array depends on the final use. The device is rapidly self-addressed in a serial manner with a group of specific oligonucleotides. In this case, the specific oligonucleotides are 3'-terminal aldehyde functionalized oligonucleotides in the range of 6-mer to 100-mers, larger polynucleotides can be attached if desired. The aldehyde functional group allows for covalent attachment to the specific microlocation attachment surface (see FIG. 4). This group of specific oligonucleotides can be readily synthesized on a conventional DNA synthesizer using conventional techniques. The synthesis of each specific oligonucleotide is initiated from a ribonucleotide controlled pore glass (CPG) support. Thus, the 3'-terminal position contains a ribonucleotide, which is then easily converted after synthesis and purification to a terminal dialdehyde derivative by periodate oxidation. The aldehyde containing oligonucleotides (40) will react readily with the primary amine functional groups on the surface of microlocations by a Schiff's base reaction process.

The electronic addressing of the device with specific oligonucleotides is shown in FIGS. 8a through 8d. The addressing of the first specific microlocation (ML-1) (81) with its specific sequence oligonucleotide (SSO-1) (82) is accomplished by maintaining the specific microelectrode (ML-1) at a positive DC potential, while all other microelectrodes are maintained at a negative potential (FIG. 8(A)). The aldehyde functionalized specific sequence (SSO-1) in aqueous buffered solution is free field electrophoresed to the ML-1 address, where it concentrates (>$10^6$ fold) and immediately becomes covalently bound to the surface of ML-1 (81). All other micro-electrodes are maintained negative, and remain protected or shielded from reacting with SSO-1 sequence (82). The ML-1 potential is then reversed to negative (−) to electrophorese any unreacted SSO-1 to a disposal system. The cycle is repeated, SSO-2 (84) - - - >ML-2 (83), SSO-3 (86) - - - >ML-3 (85), SSO-n - - - >ML-n until all the desired microlocations are addressed with their specific DNA sequences (FIG. 8(D)).

Another method for addressing the device is to transport specific binding entities such as specific oligonucleotides from an electronic reagent supply device. This supply device would hold a large quantity of binding entities or reagents and would be used to load analytical devices. Binding entities would be electronically transported between the two devices. This system eliminates the need for physical manipulations, such as micro-pipetting, and for complicated fluidic delivery systems within or between devices.

Yet another method for addressing the device is to carry out the combinatorial synthesis of the specific oligonucleotides at the specific microlocations. Combinatorial synthesis is described in a later section. After the device is addressed with specific DNA sequences, it is important that the micro-electrodes beneath the microlocations on the array device remain as independent working direct current (DC) electrodes. This is made possible because the attachment to the electrode surface is carried out in such a manner that the underlying micro-electrode does not become chemically or physically insulated. Each micro-electrode can still produce the strong direct currents necessary for the free field electrophoretic transport of other charged DNA molecules to and from the microlocation surface. Thus, the DNA array device provides complete electronic control over all aspects of the DNA hybridization and any other subsequent reactions.

Figure 9A:
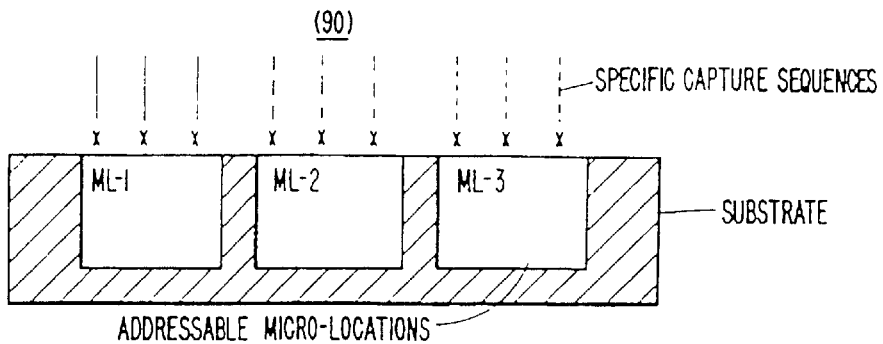
FIGS. 9a, 9b and 9c show an electronically controlled hybridization process with sample/target DNA being concentrated at microlocations containing specific DNA capture sequences, FIG. 9a showing specific capture sequences on addressable microlocations, FIG. 9b showing specific and nonspecific DNA adjacent the structure of FIG. 9a and FIG. 9c showing hybridized material adjacent microlocations ML-1 and ML-3.
Figure 9B:
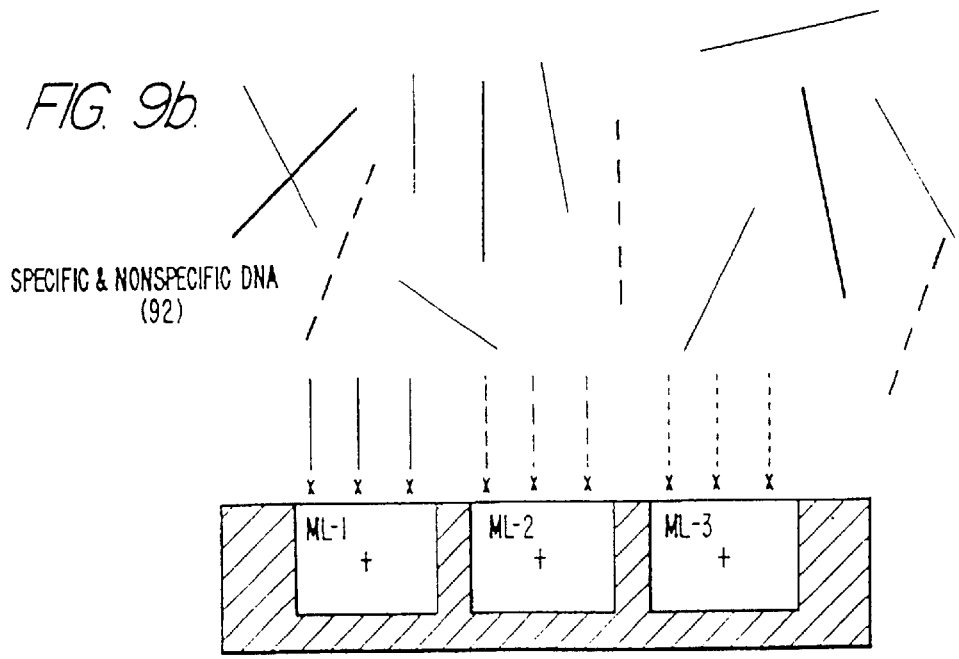
Figure 9C:
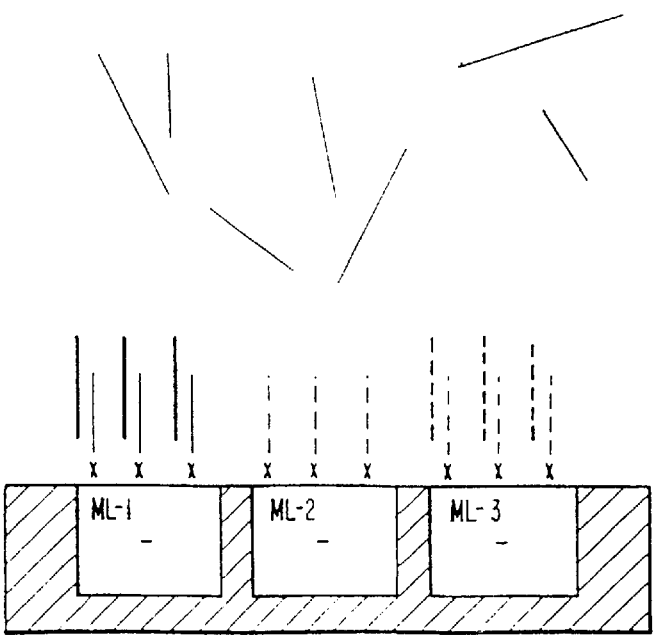

An example of an electronically controlled hybridization process is shown in FIGS. 9a through 9c. In this case, each addressable microlocation has a specific capture sequence (90). A sample solution containing target DNA (92) is applied to the device. All the microlocations are activated and the sample DNA is concentrated at the microlocations (FIG. 9(B)). Target DNA molecules from the dilute solution become highly concentrated at the microlocations, allowing very rapid hybridization to the specific complementary DNA sequences on the surface. Reversal of the micro-electrode potential repels all un-hybridized DNA from the microlocations, while the target DNA remains hybridized (FIG. 9(C)). In similar fashion, reporter probes are hybridized in subsequent steps to detect hybridized complexes.

The electronic control of the hybridization process significantly improves the subsequent detection of the target DNA molecules by enhancing the overall hybridization efficiency and by removing non-specific DNA from the microlocation areas. It is expected that 10,000 to 100,000 copies of target sequences in un-amplified genomic DNA will be detectable. Hybridization reactions of this type can be carried out in a several minutes or less under isothermal conditions well below the Tm of the probes; and with minimal outside manipulations (i.e., conventional washing steps are reduced and in some cases are completely eliminated).

Another common format for DNA hybridization assays involves having target DNAs immobilized on a surface, and then hybridizing specific probes to these target DNAs. This format can involve either the same target DNAs at multiple locations, or different target DNAs at specific locations. FIGS. 1a and 10b show an improved version of this serial hybridization format. In this case microlocations (101–107) are addressed with different capture DNAs. These are hybridized in a serial fashion with different sequence specific oligonucleotides (108,109). The microlocations are sequentially biased positive to transport molecules to itself and then biased negative to transport molecules to the next microlocation. At the proper electrode potential, the specifically hybridized DNA probes will remain at that microlocation, while un-hybridized probes are transported to the next microlocation. The sequence specific oligonucleotides probes can be labeled with a suitable reporter group such as a fluorophore.

Figure 11A:
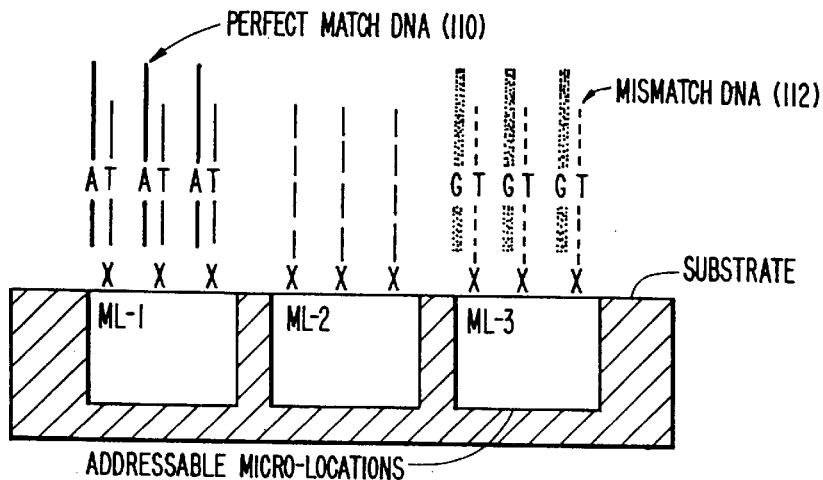
FIGS. 11a, 11b and 11c show the electronic stringency control (ESC) of a hybridization process for determining single point mutations, FIG. 11a showing uncharged addressable microlocations, FIG. 11b showing negatively charged microlocations and FIG. 11c showing negatively charged microlocations with material denatured from microlocation ML-3.
Figure 11B:
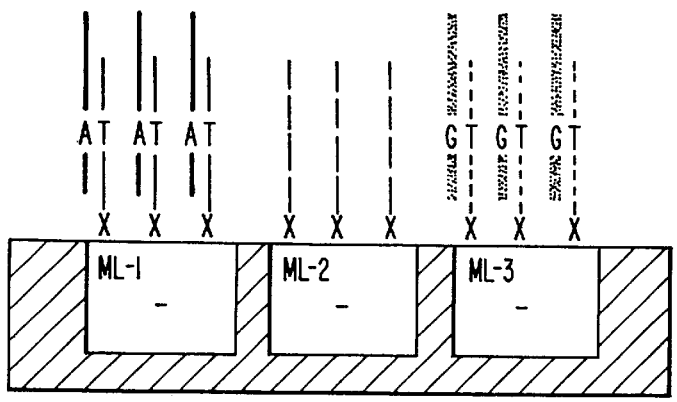
Figure 11C:
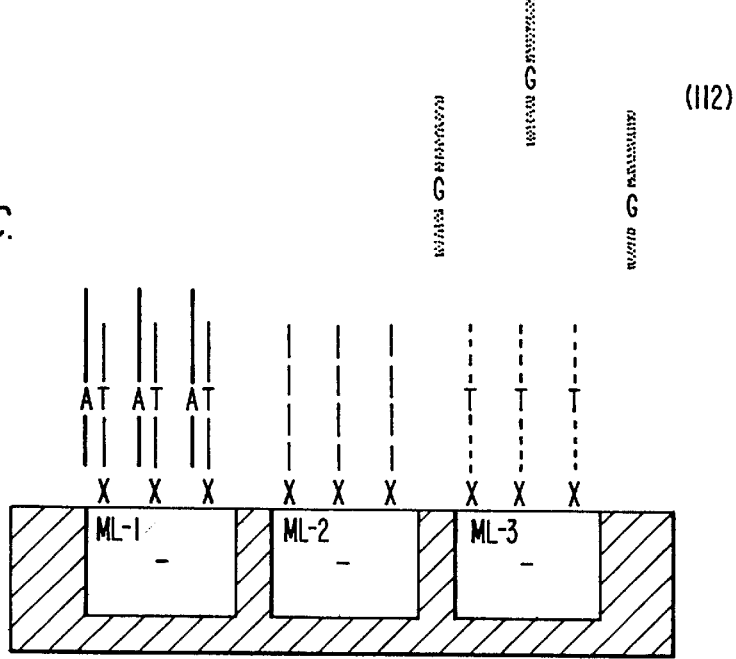

The disclosed device is able to provide electronic stringency control. Stringency control is necessary for hybridization specificity, and is particularly important for resolving one base mis-matches in point mutations. FIGS. 11a through 11c show how electronic stringency control can be used for one base mis-match analysis. Electronic stringency control can also be applied to multiple-base mis-match analysis. In FIG. 11(A) the perfectly matched DNA hybrid (110) is slightly more stable than mis-matched DNA (112) hybrid. By biasing the microlocations negative (FIG. 11(B)) and delivering a defined amount of electrophoretic power in a given time, it is possible to denature or remove the mismatched DNA hybrids while retaining the perfectly matched DNA hybrids (FIG. 11(C)). FIG. (15) compares the results for an electronic hybridization process utilizing electronic stringency control with a conventional hybridization process. The hybridization involves 15-mer G and A point mutation probes for the Ras 12 oncogene mutation. The electronic hybridization result show greatly improved hybridization efficiency and a very large discrimination ratio for the one base mis-match over the conventional procedure.

In a further refinement, the claimed device provides independent stringency control to each specific hybridization reaction occurring on the device. In effect each hybridization is a an independent reaction. With a conventional or passive array format, it is impossible to achieve optimal stringency for all the hybridization events which are occurring in the same hybridization solution. However, the active array devices of this invention are able to provide different electronic stringency to hybridizations at different microlocations, even though they are occurring in the same bulk hybridization solution. This attribute overcomes the inherent limitation to conventional matrix or array hybridization formats, sequencing by hybridization (SBH) formats, and other multiplex analyses.

In addition to improving the specificity (i.e., discrimination ratio) and sensitivity for hybridization (such as single point mutations detection), electronic stringency control allows oligonucleotides outside the normal size range to be used in these applications. Oligonucleotide sequences ranging from 8-mer to 21-mer are considered acceptable for point mutation detection with conventional hybridization procedures. In the current practice using conventional hybridization procedures, oligonucleotides in the 10-mer to 19-mer are used most frequently in these conventional procedures which utilize temperature and salt concentration for stringency control. Oligonucleotides shorter than 10-mers have been found to be not acceptable for multiplex hybridizations; and sequences shorter than 8-mers are not even considered for use because of poor hybridization efficiencies. Sequences longer than 21-mers are not used because they have very poor discrimination ratios between the match and mismatch probes. As the sequence length goes beyond a 21-mer, the ability to distinguish the difference in the hybridization signals between the match and mis-match probes is greatly reduced.

We have found that hybridizations carried out on APEX devices with electronic stringency control allows both shorter (7-mer and shorter) and longer (22-mer and longer) oligonucleotides to be used with very high discrimination ratios. The use of shorter oligonucleotide sequences (7-mer and less) has advantages for sequencing by hybridization (SBH). Shorter length sequences allow arrays with a smaller number of oligonucleotides (8-mers=65,536, 7-mers=16, 384, 6-mers=4,096) to be used for this SBH applications. The use of longer sequences (22-mer and longer) with electronic stringency control allows more sensitive and selective point mutation analysis to be carried out. The use of longer probes provides higher sensitivity in DNA samples with high complexity, and also higher overall hybridization efficiencies.

Electronic hybridization techniques can be used to carry out in-situ hybridizations. In-situ represent a fundamentally different hybridization format in that target DNA (or RNA) is not removed from cells, but detected directly inside them. In-situ hybridization procedures are generally complex and time consuming, and the detection of short target sequences (i.e. single point mutations) is nearly impossible. Electronic controlled in-situ hybridizations can be carried out on an APEX device that attaches and processes cells directly on the active surface of the device (see Example 14 concerning sample preparation techniques). However, rather than extracting DNA from the cells, the APEX device electronically hybridizes reporter probes directly to the DNA within the cells. Electronic stringency control is used to increase both selectivity and sensitivity by eliminating much of the non-specific binding and improving overall hybridization efficiency.

Figure 12A:
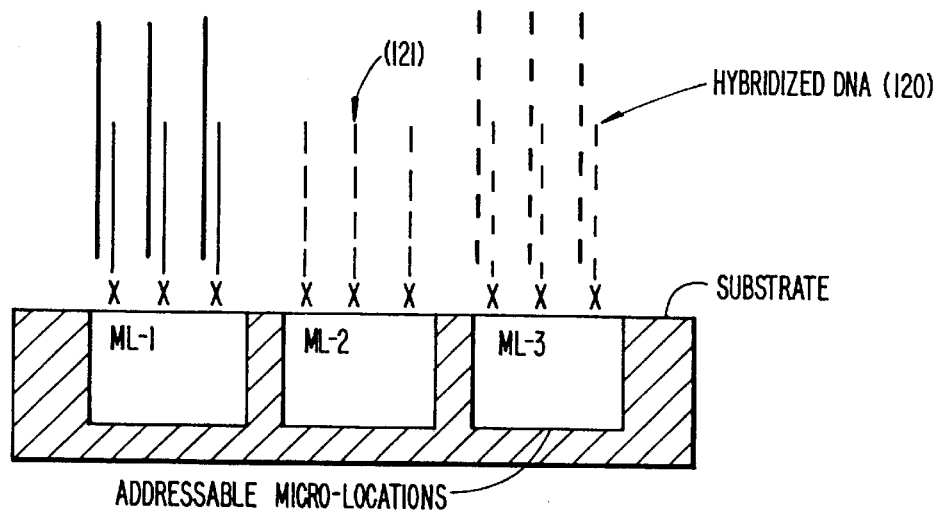
FIGS. 12a, 12b, 12c and 12d show a scheme for the detection of hybridized DNA without using labeled DNA probe, i.e., electronically controlled fluorescent dye detection process, FIG. 12a showing uncharged microlocations, FIG. 12b showing negatively charged microlocations, FIG. 12c showing uncharged microlocations with dye and FIG. 12d showing positively charged microlocations.
Figure 12B:
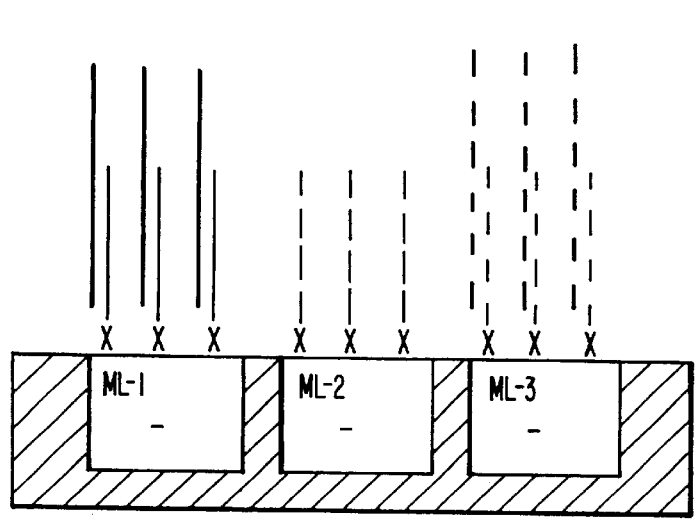
Figure 12C:
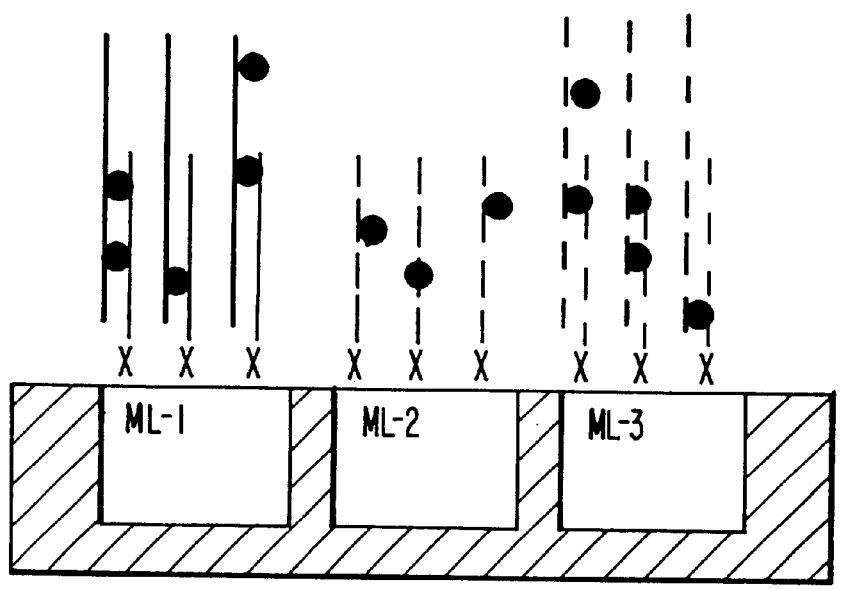
Figure 12D:
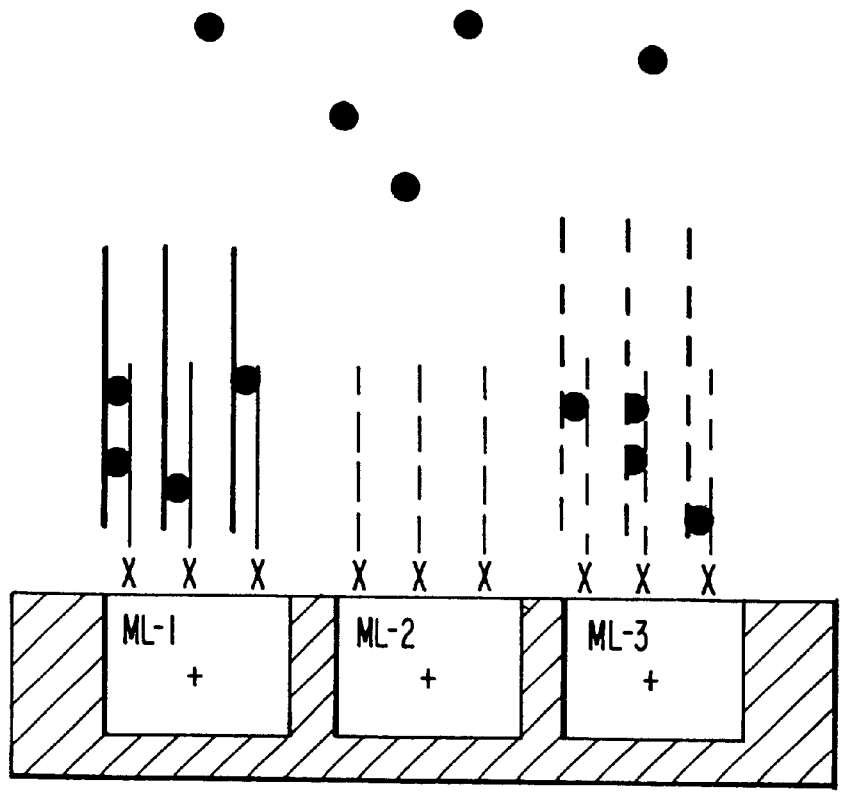

The ability to provide electronic stringency control to hybridizations also provides new mechanisms for detecting DNA hybridization without using a reporter group labeled DNA probe. It provides a way to carry out a more direct detection of the hybridization process itself. A fluorescent dye detection process is shown in FIGS. 12a through 12d and described in Examples 4 and 6. Direct detection of DNA hybrids can be achieved by using DNA binding dyes such as ethidium bromide. The dye binds to both double-stranded and single-stranded DNA but with a greater affinity for the former. In FIG. 12(B) positively charged dye (122) is transported to negatively biased microlocations. The dye binds to both hybridized (120) and unhybridized (121) DNA sequences (FIG. 12C). By biasing the microlocations positive and delivering a defined amount of power in a given amount of time, the dye molecules bound to un-hybridized microlocations is selectively removed. A proper amount of potential can be applied which does not adversely affect the DNA hybrids. The hybridized DNAs with associated dye molecules are then fluorescently detected using associated or integrated optical systems. The following reiterates important advantages the devices of this invention provide for nucleic acid hybridization reactions and analysis:

(1) The rap 1450× rapid bound target DNA and/or probe DNA sequences to specific microlocation(s) where hybridization is to occur. This process can take place in the range of 5 to 120 seconds.

(2) Concentrating dilute target DNA and/or probe DNA sequences at specific microlocation(s) where hybridization is to occur. The concentrating effect can be well over a million fold (>$10^6$).

(3) The rapid removal of non-specifically bound target DNA sequences from specific microlocation(s) where hybridization has occurred. This process can take place in the range of 5 to 120 seconds.

(4) Rapid removal of competing complementary target DNA sequences from specific microlocation(s) where hybridization has occurred. This process can take place in the range of 5 to 120 seconds.

(6) The ability to carry out a large number of independent hybridization reactions in a matter of minutes.

(7) The ability to carry out a hybridization process at isothermal conditions well below the Tm of the probes, and with minimal outside manipulations or washing steps.

(8) The use of electronic stringency control (ESC) to remove partially hybridized DNA sequences.

(9) The ability to carry out hybridization analysis of un-amplified genomic target DNA sequences in the 1000 to 100,000 copy range.

(10) The use of ESC to improve the discrimination ratio (i.e., resolution) and sensitivity of single base mismatch hybridizations (point mutations).

(11) The ability to use single point mutation probes that are either shorter (7-mer or less) or longer (22-mer or greater) than those used in conventional hybridization procedures.

(10) The use of ESC to provide individual stringency control in matrix hybridizations.

(13) Improving the detection of hybridization event by removing non-specific background components.

(14) The ability to carry out electronic in-situ hybridization on fixed cells.

(15) The development of a detection method which eliminates the need for using covalently labeled reporter probes or target DNA to detect hybridization.

III(b) REPRODUCTION OF DEVICES

Figure 13C:
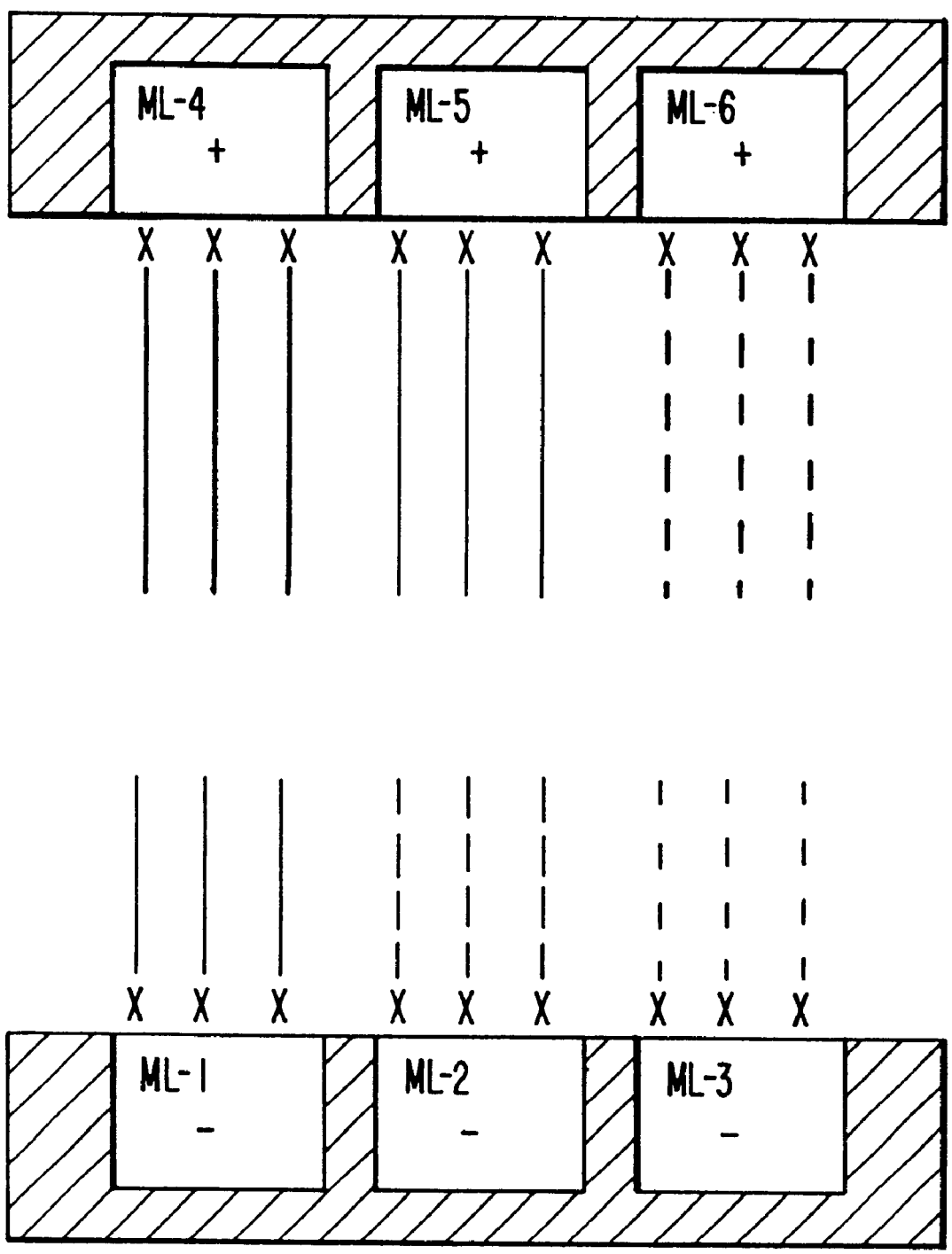

In addition to separately addressing individual devices with specific binding entities, it is also possible to produce a master device, which can copy specific binding entities to other devices. This represents another method for the production or manufacture of devices. The process for the replication of devices is shown in FIGS. 13a through 13c. A master device containing microlocations which have been addressed with specific binding sequences is hybridized with respective complementary DNA sequences (130). These complementary sequences are activated and thus capable of covalent binding to the microlocation attachment layer.

An unaddressed sister device (132) containing an attachment layer,is aligned with the hybridized master device (FIG. 13(B)). The master device microlocations are biased negative and the sister device microlocations are biased positive. The DNA hybrids are electronically denatured and are transported to the sister device, where the activated DNA sequence binds covalently to the microlocation (FIG. 13(C)). The process can be performed in parallel or in series, depending on the device geometry so that crosstalk between the microlocations is minimized. The hybrids can be denatured by applying a sufficient negative potential or by using a positively charged chaotropic agent or denaturant.

Alternatively, the DNA probes contained in a solution, in a gel matrix, or adsorbed to an affinity material (ion exchange resin etc.), within independent channels or chambers of the master device, may be electronically transported in a serial or parallel fashion to selected microlocations on a sister device. The above can be considered suitable processes for manufacturing addressed DNA chip devices for diagnostic and other applications.

III(c) COMPONENT DEVICES AND INTEGRATED APEX SYSTEMS

A number of separate APEX devices or chips can be combined to form an integrated APEX System. Because APEX type devices can carry out many different functions, and reactants can be moved between devices by free field electrophoresis, integrated systems can be developed. For example, separate APEX devices or chips which: (1) selectively bind and lyse cells, (2) electronically dispense reagents, (3) carry out pre-hybridizations, (4) act as waste disposal units, (5) provide storage for DNA fragments, and (5) carry out hybridization analysis can be combined to form a sample preparation and hybridization analysis system (see Example 14 and FIG. 19). These integrated APEX microelectronic systems are the equivalent of complete clinical analyzers or programmable molecular biology laboratories (i.e. laboratories on a chip). However, they go beyond automation (robotics) or other microanalytical devices in that they require minimal fluidics or physical manipulation of samples, reagents, and reactants. Additional types of integrated APEX systems would include but are limited to, those which could carry out in-situ hybridizations, cell selector and processor systems, and immunodiagnostic analyzers.

III(d) DETECTION SYSTEM AND REPORTER GROUPS

In the case of binding reactions involving fluorescent labelled reporter groups, it is possible to use an epifluorescent type microscope detection system for the analysis of the binding reactions on APEX devices. The overall sensitivity of the system depends on the associated detector component (cooled charged coupled devices (CCD), intensified charged coupled device (ICCD), microchannel plate detectors, or photon counting photomultiplier (PMT) systems). Alternatively, sensitive CCD chip detectors or avalanche photodiode (APD) detectors can be more directly associated with the APEX device. These systems would somewhat reduce the necessity for complex optics. More advanced systems will involve integrating optoelectronic or electronic detection elements into the APEX chip. Both optical and direct electronic detection of DNA is possible with these systems. It is contemplated by this invention that the most advanced versions will ultimately involve sandwiching together a microelectronic detector and on board controller component to the basic APEX chip component. Electronic and optical (waveguide) connections would be made directly through the bottom of the APEX component. This strategy solves a number of problems related to fabrication techniques, materials compatibilities, and cost effectiveness for making the APEX component disposable.

In addition to a variety of fluorescent dyes and reporter groups which can be used to label DNA probes, target DNAs, or antibodies; other types of labels or reporter groups can be used. These include chemiluminescent labels, non-linear optical (frequency doubler) materials, biotin/avidin complexes and various enzymes.

III(e) COMBINATORIAL BIOPOLYMER SYNTHESIS

The devices of this invention are also capable of carrying out combinatorial synthesis of biopolymers such as oligonucleotides and peptides. Such a process allows self-directed synthesis to occur without the need for any outside direction, influence or mechanical movements. Other processes for combinatorial, synthesis require physical masks and complex photolithographic procedures, microrobotic pipetting systems for reagent delivery, or complicated physical movement of components to carry out the actual synthesis at microscopic locations. The combinatorial synthesis disclosed in this invention allows very large numbers of sequences to be synthesized on a device. The basic concept for combinatorial synthesis involves the use free field electrophoretic transport to deliver, concentrate, and react monomers, coupling reagents or deblocking reagents at specific addressable microlocations on the device. The concept capitalizes on the inherent ability of the device to electronically protect certain locations from the effects of nearby reagents and reactants. Also important to the concept is the identification of selective steps in these chemical synthesis processes where one or more of the reactants has either a net positive or negative charge, or to create such suitable reagents for these processes.

One method for combinatorial oligonucleotide synthesis is shown in FIGS. 14a through 14f. This method begins with a set of selectively addressable microlocations (140) whose surfaces have been derivatized with blocked primary amine (X—NH—) groups (142). The initial step in the process involves selective deblocking of microlocations using a charged deblocking reagent (144). In this case, the reagent would carry a positive (+) charge. The process is carried out by applying a negative potential to those microlocations being de-blocked, and a positive potential to those which are to remain protected (FIG. 14(B)). Application of positive and negative potentials to selective electrodes causes the charged reagents to be moved from a reagent delivery site and concentrated at the desired microlocation being de-blocked, while excluding reagents from the other microlocations.

In the second step, chemical coupling of the first base, in this case cytosine, to the deblocked microlocations is carried out by simply exposing the system to the phosphoramidite reagent (x-C) (146). The (C) nucleotide couples to de-blocked microlocation surfaces, but not to any of the blocked electrode surfaces (FIG. 14(C) and (D)). At this point normal phosphoramide chemistry is carried out until the next de-blocking step.

Figure 14A:
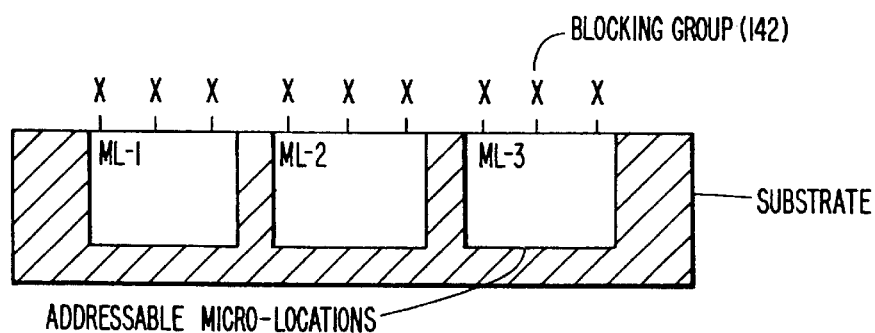
FIGS. 14a, 14b, 14c, 14d, 14e and 14f show a scheme of electronically directed combinatorial synthesis of oligonucleotides, FIG. 14a showing addressable microlocations with blocking groups, FIG. 14b showing addressable microlocations with blocking groups in combination with a deblocking group, FIG. 14c showing blocked and deblocked addressable microlocations in the presence of monomer C, FIG. 14d showing addressable microlocations in combination with a deblocking group, FIG. 14e showing deblocked cites on microlocation ML-2 in the presence of monomer A and FIG. 14f showing microlocations with deblocking groups on the terminal ends of sequences.
Figure 14B:
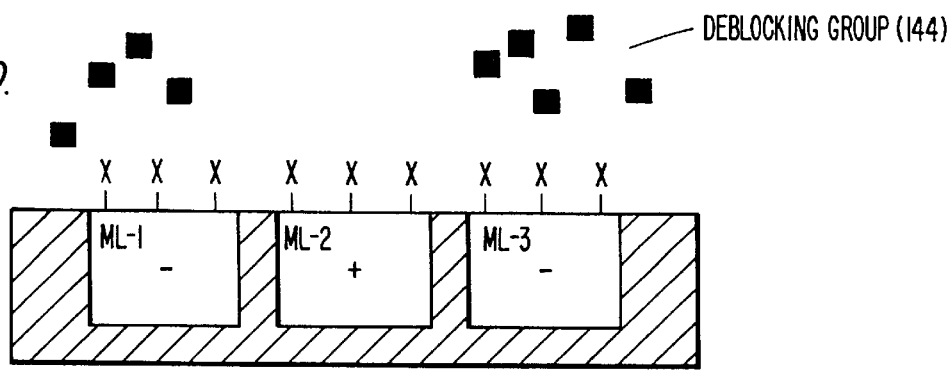
Figure 14C:
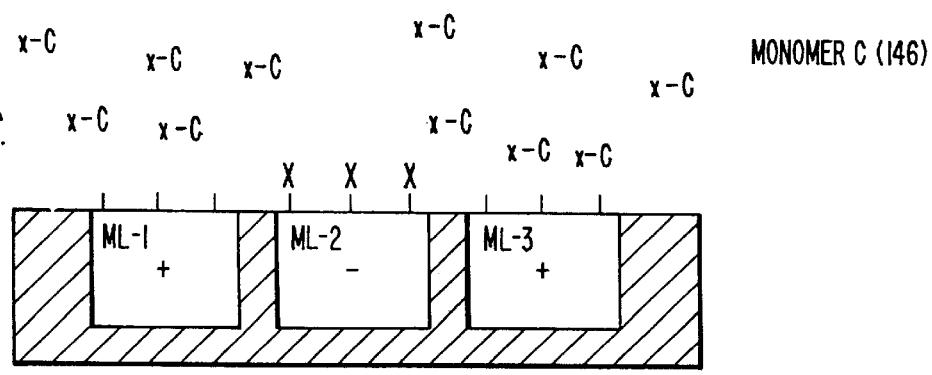
Figure 14D:
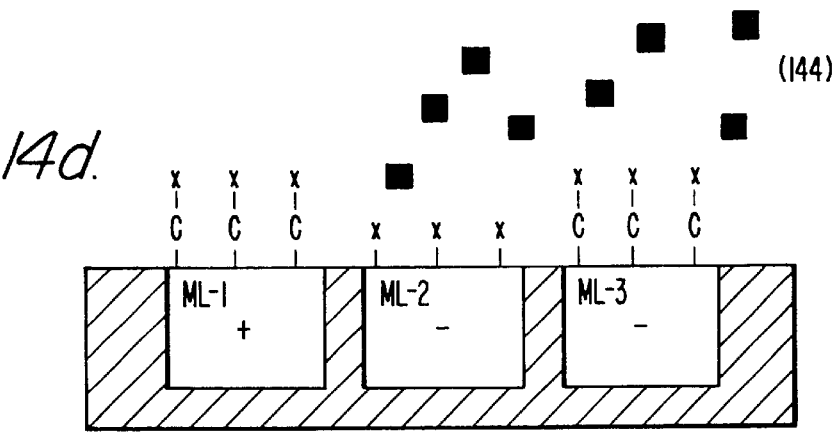
Figure 14E:
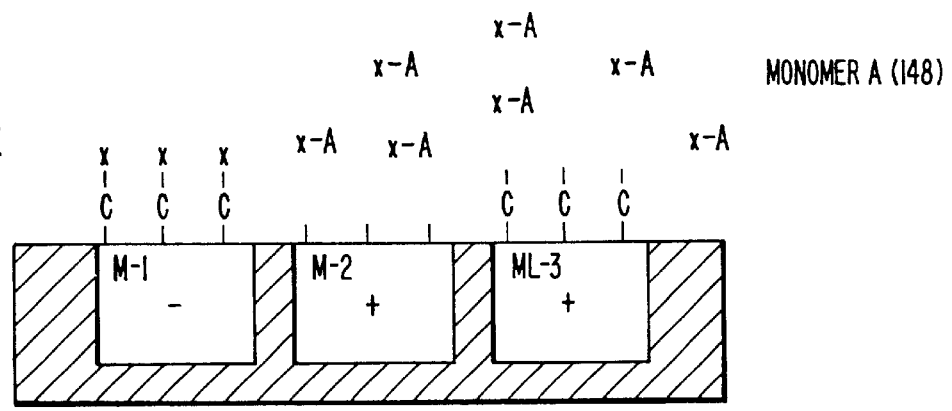
Figure 14F:
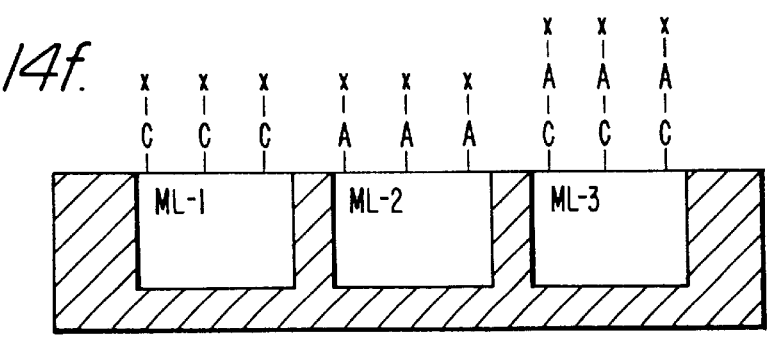
Figure 15:
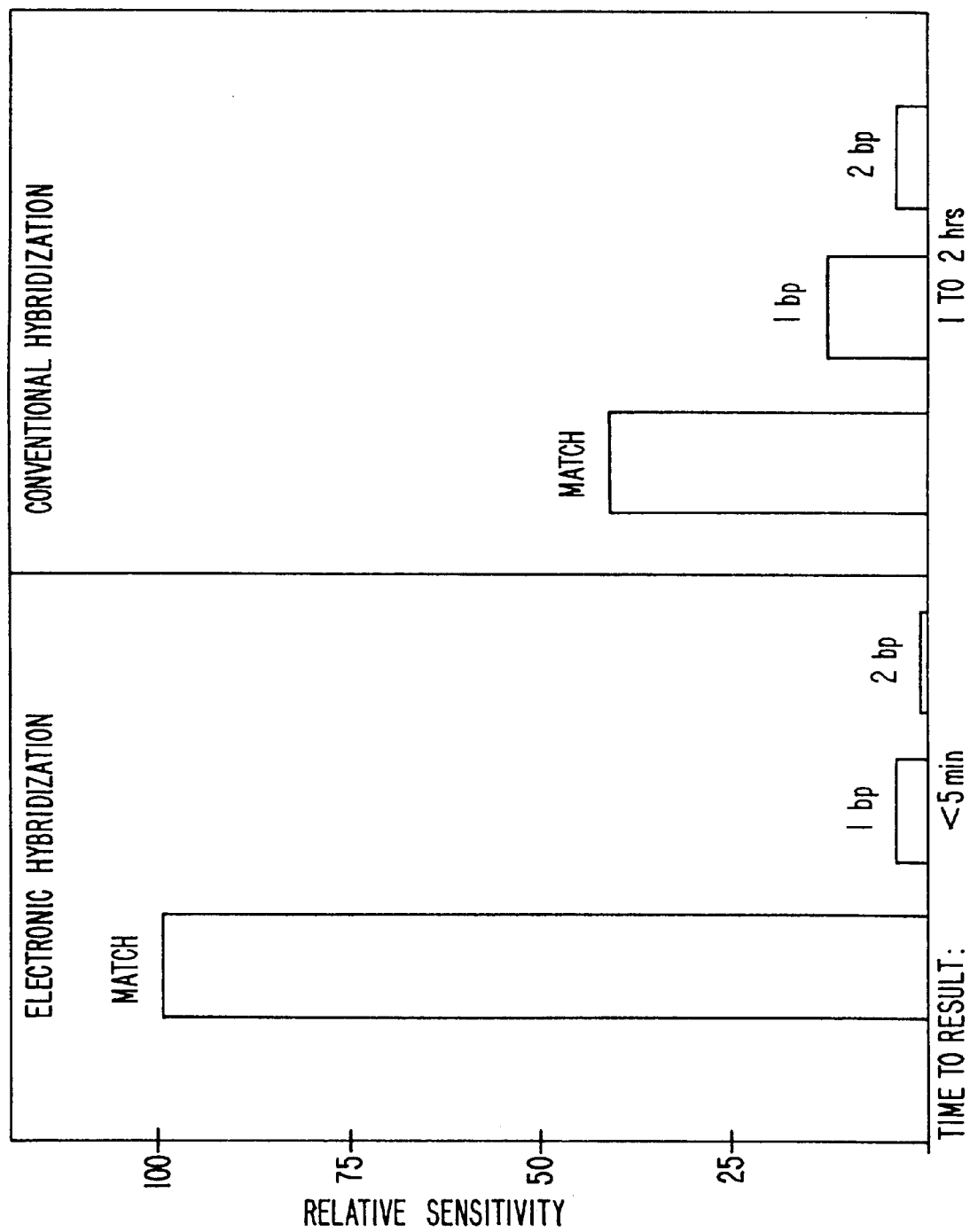
FIG. 15 shows a graph comparing the results for 15-mer Ras 12 point mutation hybridizations carried out using electronic stringency control and conventional techniques.
Figure 16:
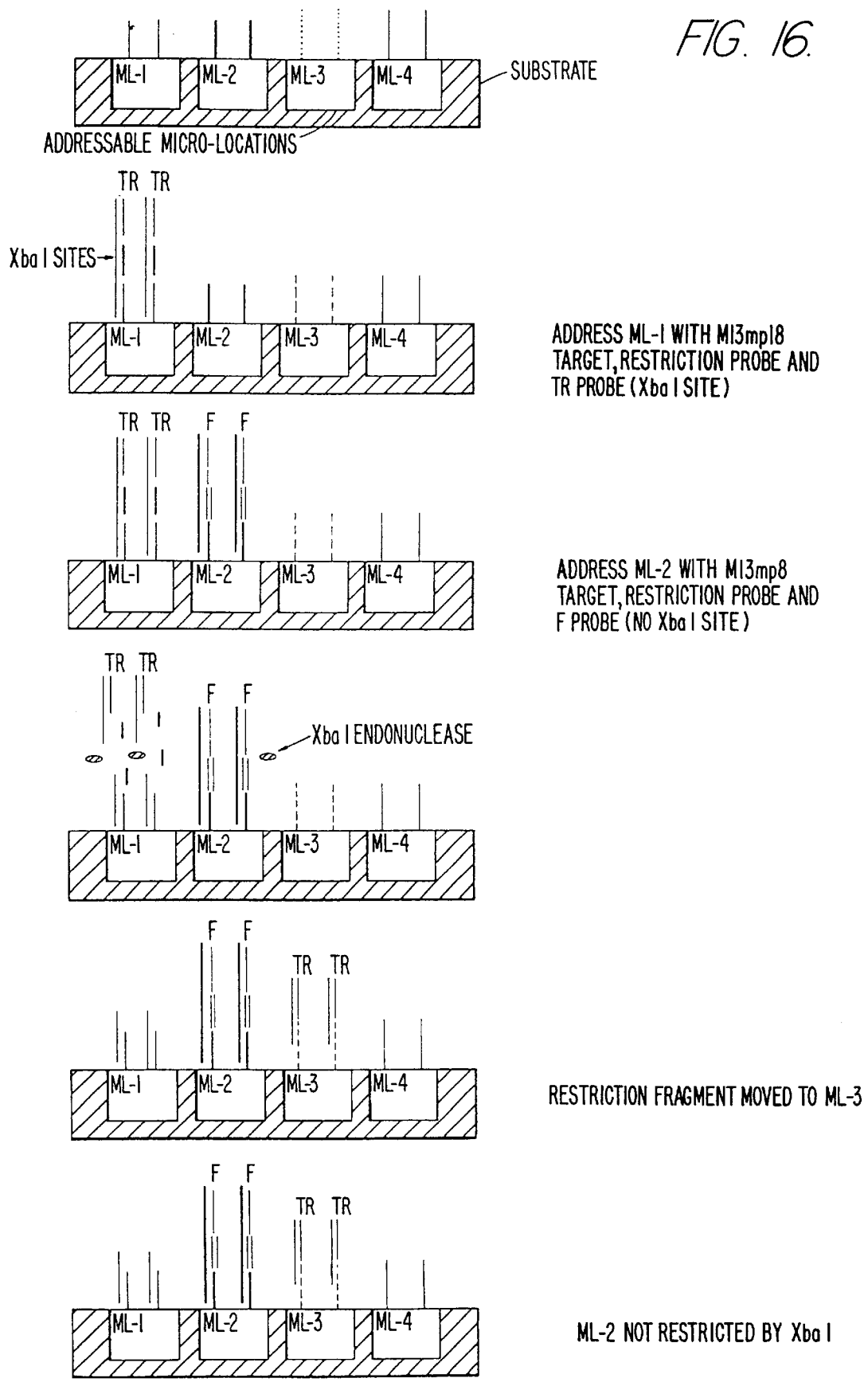
FIG. 16 shows a scheme for electronically controlled restriction fragment cleavage of DNA.

At the second de-blocking step (FIG. 14(D)), those electrode positions which are to be coupled with the next base are made negative, and those which are to remain protected are made positive. The system is now exposed to the next base to be coupled, in this case (x-A) (148), and selective coupling to the de-blocked microlocation is achieved (FIG. 14(E) and (F)). The coupling and de-blocking procedures are repeated, until all the different DNA sequences have been synthesized on each of the addressable microlocation surfaces.

The above example represents one possible approach for the synthesis of nucleic acids. Another approach involves a complete water soluble DNA synthesis. In this case, charged water soluble coupling agents, such as 1-ethyl-3-(3-dimethylaminopropyl) carbodiimide (EDCA), is used to carry out oligonucleotide synthesis with water soluble nucleotide derivatives. This approach would have significant advantages over present organic solvent based methods which require extensive blocking of the base moieties. Water soluble synthesis would be less expensive and eliminate the use of many toxic substances used in the present organic solvent based processes. A third approach, again for water soluble syntheis, involves the use of charged monomers and enzymes.

III(e)(1) Oligonucleotide Synthesis with Terminal Transferase

This approach for combinatorial synthesis of oligonucleotides involves the use of a nucleic acid polymerizing enzymes. This approach utilizes terminal transferase, 3'-monophosphate esters of 5'-deoxyribonucleotide triphosphates, and a phosphatase. Terminal transferase is used to couple the nucleotides. The 3-phosphate ester serves as a blocking group to prevent the addition of more than one nucleotide in each coupling step. A 3'-phosphatase is used to remove the 3'-phosphate ester for the next coupling step.

Because all reagents are water soluble and charged, general APEX techniques can be used for all steps in this combinatorial synthesis procedure. In this approach, an APEX matrix is used which has A, T, G, and C nucleotides linked through their 5'-hydroxyl position to the appropriate number of addressed microlocations on the device. The first nucleotides are linked to be standard APEX addressing techniques.

The first round of coupling reactions is initiated by biasing positive all those microlocations which are to be coupled with an A nucleotide in their second position, and biasing negative the two electronic reagent dispensers containing terminal transferase and the 3'-phosphate ester of deoxyadenosine triphosphate. The reagents are free field electrophoresed to the appropriate microlocations and the A nucleotide is coupled by the terminal transferase to the first nucleotide on the matrix. Because the nucleotide triphosphates are esterified with a phosphate group in their 3' positions, terminal transferase adds only one nucleotide at a time.

After the nucleotide coupling is complete, the microlocations are biased negative and the waste disposal system is biased positive and the enzyme and spent reagents are removed. The process is repeated for the first round coupling of G, C, and T nucleotides until all the microlocations have been coupled.

When first complete round of coupling (A,T, G and C) is complete, all the microlocations are biased positive and a reagent dispenser with a 3'-phosphatase enzyme is biased negative. The 3'-phosphatase is free field electrophoresed to the microlocations where it hydrolyses the 3'-phosphate ester. The removal of the phosphate ester leaves the 3'-hydroxyl group ready for the next round of coupling reactions. The coupling reactions are carried out until the desired oligonucleotide sequences are complete on the APEX device.

In addition to DNA synthesis, a similar process can be developed for RNA synthesis, peptide synthesis, and other complex polymers.

III(f) ELECTRONICALLY CONTROLLED MOLECULAR BIOLOGY AND AMPLIFICATION REACTIONS

A variety of molecular biological reactions including linear and exponential multiplication or amplification of target DNA and RNA molecules can be carried out with APEX microelectronic devices and chips.

Restriction enzyme cleavage restrictions and DNA fragment analysis can be carried out under complete electronic control. Nucleic acid multiplication or amplification reactions with APEX devices are distinct from other "DNA Chip" devices which are basically passive micro-matrix supports for conventional amplification procedures (PCR, LCR, etc.). New mechanisms for amplification come directly from the active nature of the APEX devices. The active device provides unique electronic mechanisms to: (1) selectively denature DNA hybrids under isothermal reaction conditions and well below their Tm point (thermal melting temperature); (2) rapidly transport or move DNA back and forth between two or more microlocations; and (3) selectively concentrate DNA modifying enzymes, such as, but not limited to, restriction endonucleases, DNA or RNA polymerases, and ligases, at any desired microlocation on the device. Examples of electronically controlled molecular biology and amplification reactions which can be carried out on the APEX devices include: (1) Electronically Directed Restriction Enzyme Clevage of ds-DNA Sequences; (2) Electronic Multiplication of Target DNA By DNA Polymerases; (3) Electronic Ligation and Multiplication of Target DNA Sequences By DNA and RNA Ligases; and (4) Electronic Multiplication of Target DNA By RNA Polymerases.

III(g) ELECTRONIC RESTRICTION FRAGMENT ANALYSIS

In addition to carrying out restriction enzyme clevage of ds-DNA, APEX devices and electronic techniques can be used to analyze and determine the relative size of DNA fragments. This is possible when DNA fragments with different lengths can be hybridized to a common capture sequence on individual microlocations. Or when DNA fragments of different lengths can be hybridized to different capture sequences, all of which have the same hybridization or binding energy. In these cases, electronic stringency control can be used to selectively de-hybridize the different DNA fragments according to the length of their un-hybridized or overhanging sequence. The electrophoretic force on the fragments with longer overhanging sequences causes them to de-hybridize before the fragments with shorter overhanging sequences. Thus, if the fragments are labelled for detection, and addresssed to specific microlocations, their sizes can be determined by the electrophoretic potential or power level required to de-hybridize them from the microlocations. It may be possible to carry out the equivalent of an electronic restriction fragment length polymorphism analysis.

III(h) Electronic Transport and Hybridization in Low Ionic Strength and Low Conductance Buffers DNA transport in low ionic strength/low conductance solutions was demonstrated in a series of fluorescent DNA checkerboard addressing experiments using 2.5% agarose coated 5580 APEX chips with 25(80 micron) microlocations and a Bodipy Texas Red-RCA5 (btr-RCA5) fluorescent oligonucleotide test probe. Checkerboard addressing involves biasing alternate microlocations positive and negative, and then reversing the bias every 6 seconds. This produces a checkerboard fluorescent pattern on the array as the fluorescent DNA probe concentrates on the positively biased microlocations and moves away from the negatively biased microlocations. Rapid (6 second) checkerboard addressing and concentration of the btr-RCA5 fluorescent DNA probe was demonstrated for the following low conductance solutions:(1) 250 mM HEPES (low conductance), (2) 10 $\mu$M sodium succinate, (3) 10 $\mu$M sodium citrate, and (4) distilled water. While, some types of low conductance or low ionic strength solutions may have somewhat better characteristics, checkerboard addressing and rapid DNA transport (DNA accumulation within 6 seconds on the 80 $\mu$m pads, with ~200 $\mu$m total distance transversed) was achieved with most low conductance systems. Additionally, DNA addressing to APEX chips in distilled water is possible because the DNA (itself a polyanion)is the electrolyte present in the bulk solution which provides the conductance. Relationship of Electrophoretic Transport Rate and the Cation/Anion Species—In addition to the fact that the mobility of the charged analyte species (DNA, proteins, etc.) is related to the ionic strength of the electrolyte solution, the mobility is also greatly influenced by the nature of the cation and anion species in the electrolyte solution (see pp 89 of "Capillary Electrophoresis: Principles and Practice" reference). This particular point is demonstrated for DNA transport in the above Biopolymers, Vol. 2, pp. 231–236, 1964 reference. FIG. 1 on page 232 of this reference shows the change in DNA mobility when using electrolytes with different univalent anions ($Li^+>Na^+>K^+>TMA^+$) at the same ionic strength. Basically, different cations can have different association constants with the DNA phosphate groups, and/or change the hydration spheres around the DNA molecules, which leads to a change in their transport rate. In addition to the effect on mobilty, different cations may effect the relative stability of double stranded DNA.

Electronic Transport & Hybridization Enhancing Buffers

Many aspects of this invention relate to our discoveries concerning the various parameters, DC and DC/AC pulsing, special electrolytes and buffers (histidine,cysteine etc.), and other conditions which improve or optimize the speed of reagent or analyte (DNA, RNA, etc.) transport, the efficiency of DNA or RNA hybridization reactions, and the overall hybridization specificity in our electric systems and devices, especially the APEX microelectronic chips. Some of these are covered in earlier patent applications and CIP's. One in particular, was the discovery that various low conductance and zwitterionic buffers, including but not limited to D-&L-histidine, di-histidines, 1 & 3 methyl-histidines, carnosine, imidazole, pyridine and collidine, provided both rapid electrophoretic DNA transport and efficient hybridization reactions. In contrast, other zwitterionic buffers such as cysteine, glycine, b-alanine and g-amino-butyric acid (GABA) provide rapid transport, but do not facilitate efficient hybridization under these conditions. When using these buffers for transport and concentration of DNA, hybridization can be achieved by rapidly replacing the buffer with a more classical hybridization buffer (100 mM NaCl & $Na_2PO_4$, etc.) immediately after appropriate DNA concentration has occurred at the microlocation. The effect on hybridization efficiency was unexpected. An additional benefit of low conductance buffers and systems is the relatively denatured condition of the target sequences when applied to the APEX chip and devices.

The advantage of histidine, di-histidines and the other hybridization enhancing buffers, is particularly important for the operation of APEX microchip type devices with 10 to 100 micron diameter microlocations. Generally, these devices (as opposed to larger scale devices) are covered with thinner permeation layers (~1 to 10 microns), and operated at a lower range of currents (~10 nA to ~5 uA) and voltages (~1.2 to 5.0 volts). These lower currents and voltages (which still produce electrophoretic transport) are used to reduce active bubbling at the positive and negatively biased microelectrode/permeation layer interface. Oxygen gas is produced at the positive electrode and hydrogen gas is produced at the negative electrode, but the gases are dissipated by diffusion, as opposed to active bubbling. At these lower currents (~10 nA to ~5 uA) and voltages (~1.2 to ~5.0 volts) one finds that the DNA transport rate is reduced when higher conductance buffers and electrolytes (>10 mM NaCl, KCl, sodium phosphate, sodium citrate, sodium borate, Tris, etc.) are used. Additionally, the concentration of the polyanionic nucleic acids is slowed by the competing concentration of the smaller and more numerous electrolyte anions (phosphate, citrate, $Cl^-$, etc.) which amass at the permeation layer surface of the positively biased microlcations. Finally, the ability of target DNA sequences to hybridize to the DNA sequences attached to the test sites is greatly reduced, due to the highly concentrated anionic environment and to corresponding lack of stabilizing cations. It should be kept in mind, that conversely the concentration of the smaller electrolyte cations ($Na^+$,$K^+$,Tris, etc.)is also occurring at the permeation layer surface of the negatively bised microlcations. Also, under low buffering conditions (<10 mM) or when the main buffer component is not an anionic species (phospate, citrate, borate, etc.), the production of a low pH (<4) acidic environment at the positively biased microlocation reduces the nucleic acid hybriidzation efficiency and can also can promote precipitation of the DNA or RNA on and within the permeation layer. Converesly, the production of an unbuffered high pH (>10) basic environment at the negatively biased microlocation can have adverse effects.

With these conditions in mind, one of the methods for carrying out "electronic DNA hybridization" is to use a low conductance buffer, such as cysteine or alanine, at a relatively high concentration (~50 mM to 100 mM) for DNA transport where the relatively lower current and voltage still produces very rapid DNA transport. Under these conditions the target DNA remains in a relatively denatured state, which reduces the competing hybridization form the complementary target strands. The target DNA can be rapidly concentrated at the microlocation test site. After transport in one of these low conductance buffers, the solution is changed to a high salt buffer (>100 mM sodium chloride or sodium phosphate) which then promotes very efficient hybridization of the concentrated target DNA to the DNA probes at microlocation test site.

Figure 19:
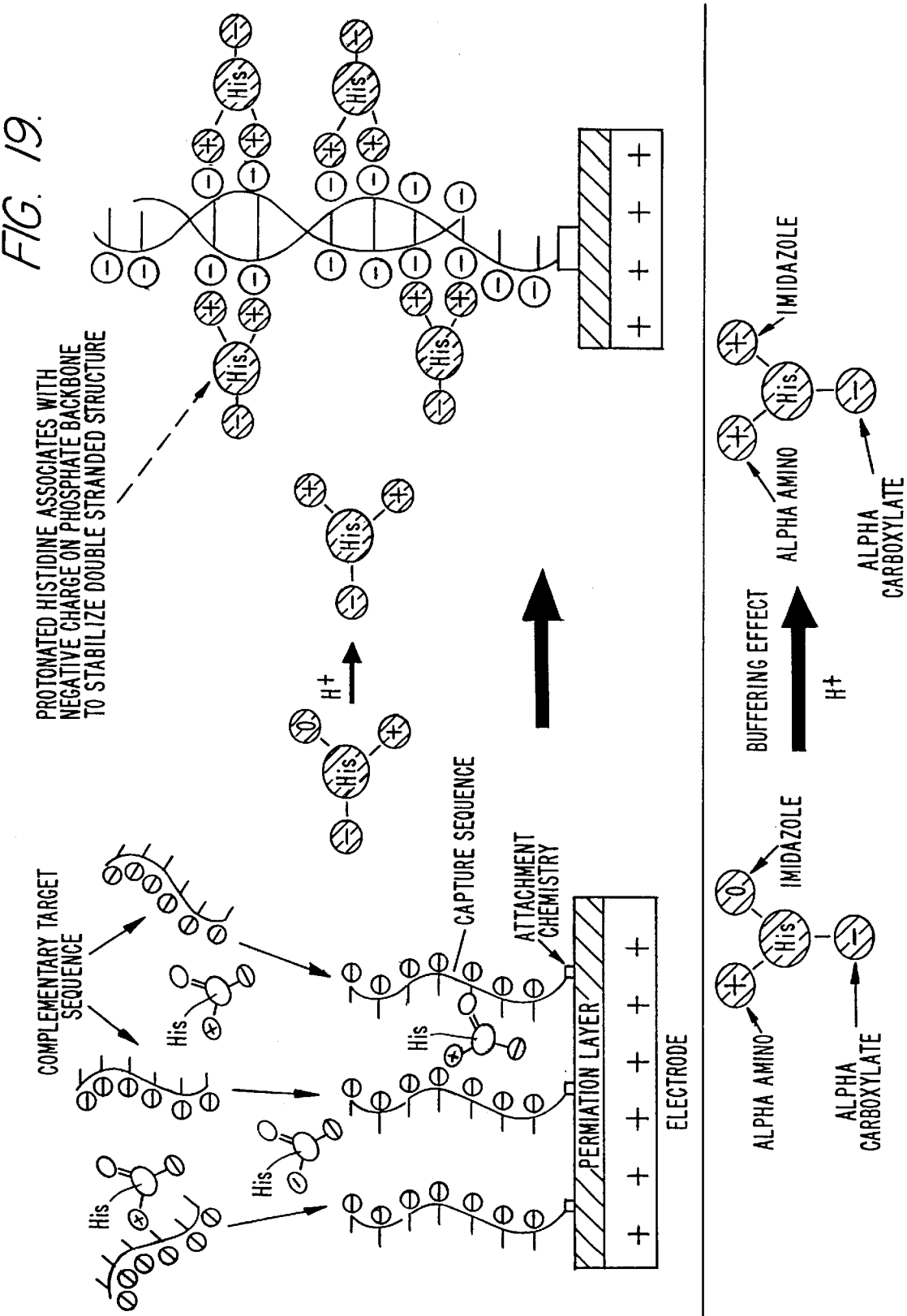
FIG. 19 shows a graphical representation of histidine stabilization of hybrids in the electronic hybridization process.

Histidine Mechanism of Action—During the transport and addressing procedures for DNA concentration and hybridization, the pH immediately above the positively biased electrode is found to be lowered, in a buffer dependent fashion. In separate experiments, it was observed for passive hybridization at acidic pH that histidine can facilitate hybridization when possessing a net positive charge but not when neutral (see Experimental Section). The ability of these histidine and associated buffers to facilitate electronic hybridization is linked to four important properties: (1) the ability to maintain target DNA in a relatively denatured state, (2) the ability to facilitate electric field concentration of DNA, (3) the ability to buffer acidic conditions present at the positively biased microlocation, (4) the ability to acquire a net positive charge capable of shielding or diminishing repulsion between the DNA phosphodiester backbone stabilizing the double-stranded structure. FIG. 19 shows the possible mechanism for histidines stabilization of DNA structures.

Basically, as the histidine molecule becomes protonated and more dicationic with a positive charge on both the a-amino group and imidazole ring, the molecule begins to stabilize the double-stranded DNA structures, promoting hybridization. Indeed, upon examining CPK space filling molecular structures of histidine and ds-DNA, the dicationic histidine species, appears to "fit" well to the phosphate oxygen anion spacing along the DNA backbone. Furhtermore, examination of CPK space filling structures suggested that di-histidine and other di- tri-, and polypeptide structures will further significantly stabilize ds-DNA structures. It is believed that in addition to these peptide structures, a large number of peptide derivatives and synthetic structures can be designed to stabilize ds-DNA.

The advantage of the histidine and associated buffers, is particularly important for the APEX microchip type devices. These particular devices when covered with thinner permeation layer (~1 to 10 microns), as opposed deep well devices (~10 to 100 micron permeation layers) and micromachined or macroscopic type devices (sample preparation, complexity reduction, amplification, electronic dot blots, etc.) are generally used at a lower range of currents (~10 nA to ~5 uA) and voltages (~1.2 to ~5 volts). This lower current and voltage reduces transport rate and hybridization efficiency in the higher conductance buffers and electrolytes. Generally, in these cases, DNA transport would be carried out in a low conductance buffer (such as Cysteine or Alanine) where relatively lower current and voltage still produces rapid DNA transport. Under these conditions DNA is rapidly accumulated at the test site, but does not hybridize efficiently. After transport in these low conductance buffers, the solution is usually changed to a high salt buffer (>100 mM sodium chloride or sodium phosphate) which then promotes very efficient hybridization of the concentrated target DNA to the DNA probes at microlocation test site.

Table 2 shows the results for a series of experiments which correlate the parameters of buffer capacity, pH, and the conductivity, with DNA accumulation and hybridization sensitivity (efficiency) using the APEX chip device.

(accumulation). There are several explanations as to why the histidine buffer produces relatively efficient DNA/DNA hybridization. One advantage is the good buffering capacity of histidine. With its pI at 7.47, histidine will buffer well under both acidic or basic conditions (see A. L. Lehninger, Biochemistry, 2ed, Worth Publishers, New York, 1975, FIG. 4–9 on page 80). The APEX chip produces acid at the positive electrode where the DNA is accumulated for hybridization, and histidine may effectively buffer these conditions. In its zwitterionic state, the concentration of histidine remains high in the local vacinity of both the positively and negatively biased microlocations. More importantly, under the acidic conditions (pH<5) at the posi-

TABLE 2

| Solution | Buffer Capacity pH 4–10 | pH at PI | Conductivity ($\mu$S) | Relative DNA Transport Rate | SA-Biotin T12 Sensitivity | Hybridization Sensitivity of DNA |
|---|---|---|---|---|---|---|
| $\beta$-Alanine | $pK_1$ - 3.6<br>$pK_2$ -10.2 | + | 7.3 | 10.0 | +++++ (fastest) | $3 \times 10^6$ | |
| Taurine | $pK_1$ - 1.5 | +/− | 4.6 | 4.5 | ++++ | $>7.5 \times 10^{10}$ | |
| Cysteine | $pK_1$ - 1.7<br>$pK_2$ - 8.3<br>$pK_3$ - 10.8 | +/− | 5.2 | 25.0 | ++++ | $3 \times 10^7$ | $7.5 \times 10^{10}$ |
| Histidine | $pK_1$ - 1.8<br>$pK_2$ - 6.0<br>$pK_3$ - 9.0 | +++ | 7.6 | 212.0 (172.0 hi purity) | +++ | $3 \times 10^4$ | $3 \times 10^6$ |
| Lysine | $pK_1$ - 2.2<br>$pK_2$ - 8.9<br>$pK_3$ - 10.3 | ++ | 9.6 | 477.0 | ++ | $>7.5 \times 10^{10}$ | |
| NaPO$_4$ | Complex | + | 7.4 | 1,400.0 | + (slowest) | | |

20 mM NaPO$_4$ adjusted to pH 7.4

In particular, Table 2 shows the effect of various zwitterionic amino acid buffers [β-Alanine, Taurine, Cysteine, Histidine, Lysine, and Sodium Phosphate (not a zwitterionic buffer)] on the hybridizability of the transported target DNA to the specific capture DNA at the test site. Table 2 shows clearly that a much lower level of hybridization sensitivity can be achieved with histidine ($3 \times 10^6$ targets) than for cysteine ($7.5 \times 10^{10}$ targets). As to transport, the conductivity generally correlates with transport under the same field conditions. β-alanine, taurine and cysteine show excellent transport, histidine shows good transport, and lysine and NaPO$_4$ show fair transport. The DNA hybridization sensitivity is reported for "normal DNA" which has negatively charged polyanionic phosphate backbone. In addition to the hybridization sensitivities, Table 2 also reports the sensitivity for the streptavidin/biotin DNA probe capture affinity. Table 2 clearly shows the correlation of DNA transport (accumulation) with low conductivity (β-alanine, taurine, cysteine, histidine). The table shows good sensitivity for the streptavidin/biotin probe affinity reaction using β-alanine, cysteine, and histidine. As reflected in the sensitivity data in Table 2, Histidine provides over four orders of magnitude better hybridization efficiency then either cysteine or other buffers, such as 20 mM NaPO$_4$. The improvement relative to cysteine is at least a factor of 10, more especially a factor of $10^2$, and most especially at least a factor of 10. Most importantly the DNA hybridization sensitivity (efficiency) is very good for the Histidine buffer. Thus of all the zwitterionic amino acid buffers presently tested, histidine, di-histidine, and histidine derivatives provide both good transport and good DNA/DNA hybridization efficiency.

It is believed that the low conductivity of the histidine buffer system accounts for the rapid DNA transport tively biased electrode the protonation of the imidazole group on the histidine begins to convert the molecule into a di-cationic species. This di-cationic species with a positively charged α-amino group and a positively charge imidazole group promotes hybridization and stabilize the DNA/DNA hybrids formed at the positively biased microlocations on the APEX chip. Cations, di-cations, and polycations are known to help stabilize DNA/DNA hybrids by reducing the repulsion of the negatively charged phosphate backbones on the double-stranded DNA structure. Thus, histidine suggests the design of compounds (histidine polypeptides, mixed peptides, synthetic derivative, etc.) which have zwitterionic, low conductance, and di-cationic, or multi-cationic character for improving electronic hybridization on APEX chip devices.

III(i) Electronic Hybridization and Point Mutation Detection in Double-Stranded PCR Amplicons A significant advantage of this invention is the ability to carry out rapid direct hybridization and base mismatch analysis on relatively large DNA fragments. It is possible to take double-stranded PCR amplicon products, other amplicon products(SDA, etc.), DNA fragments, or RNA fragments and:(1) dilute them directly into a low conductance histidine buffer (1 to 50, or higher dilution), (2) carry out rapid heat denaturation, (3) apply the sample (~5 uL) to an APEX chip (pre-addressed with capture probe sequences for discrimination), (4) carry out a 2 minute electronic hybridization, (5) wash the chip several times, (6) hybridize a fluorescent reporter probe sequence (optional), (7) carry out 30 second electronic stringency (using the appropriate current level for the particular base mismatch sequence), (8) carry out fluorescent detection and analysis (~1 minute).

The time necessary to carry out the whole process is less than 30 minutes. The fast hybridization rate is due to the unique advantage of electronic hybridization in low conductance buffers like histidine. The rapid base mismatch discrimination is due to the unique advantages of electronic stringency. Double-stranded PCR products can be applied to the chip with minimal denaturation, and it is not necessary to isolate single-stranded target sequences. Step (6) is not necessary if the amplicon or fragment is already fluorescently labeled, in most cases labeling can be carried out in the PCR amplification procedure using fluorescent labeled primers. For fully amplified PCR amplicons it is not necessary to de-salt the sample, as it can be diluted directly into the low conductance (histidine buffer). For lower copy number amplicons, a de-salting step to lower conductance is optional.

In one example, a 123 bp PCR amplicon was produced by standard PCR reaction process from Sickle Cell positive tissue. Three 80 micron microlocations in each of the five rows on an 25 test site APEX array were pre-addressed with three biotinylated capture probes; a 24-mer biotinylated Sickle Cell match sequence (GCAP-3); a 24-mer biotinylated Sickle Cell mismatch T→A (GCAP4); and a completely non-complementary sequence (ATA4). The amplicons were diluted 1 into 50 parts of histidine buffer, and applied to an APEX chip. The basic process described above was then carried out. Four different electronic stringency current levels were used to determine optimal electronic stringency. The following discrimination ratio's for the "mismatch to match" were obtained: 1.3 to 1 for 533 nA/site; 1.4 to 1 for 566 nA/site; 2.0 to 1 for 600 nA/site, 1.8 to 1 for 633 nA/site, and 1.7 to 1 for 600 nA/site, a repeat. Thus it was possible rapidly detect and obtain 2 to 1 discrimination ratio for a mismatch (A→T) in double-stranded PCR amplicon target material. Thus, this invention allows a rapid process for carrying out direct hybridization base mismatch analysis.

The invention will now be described in greater detail by reference to the following non-limiting examples regarding the making and applications of APEX devices.

The recipes for buffers, solutions, and media in the following examples are described in J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989.

IV. EXAMPLES

Example 1

Oligonucleotide Synthesis and Modifications

Synthetic DNA probes were made using conventional phosphoramidite chemistry on Applied Biosystems automated DNA synthesizers. Oligomers were designed to contain either a 5'-amino or a 3'-ribonucleoside terminus. The 5' functionality was incorporated by using the ABI Aminolink 2 reagent and the 3' functionality was introduced by initiating synthesis from an RNA CPG support. The 3'- ribonucleotide terminus can be converted to a terminal dialdehyde by the periodate oxidation method which can react with primary amines to form a Schiff's base.

Reaction conditions were as follows: Dissolve 20–30 O.D. oligomer in water to a final concentration of 1 OD/µl. Add 1 vol of 0.1M sodium acetate, pH 5.2 and 1 vol 0.45M sodium periodate (made fresh in water). Stir and incubate reaction for at least 2 hours at ambient temperature, in the dark. Load reaction mix onto a Sephadex G-10 column (pasteur pipette, 0.6×5.5 cm) equilibrated in 0.1M sodium phosphate, pH 7.4. Collect 200 µl fractions, spot 2 µl aliquot on thin layer chromatography (TLC) and pool ultra violet (UV) absorbing fractions.

The following oligomers contain 3'-ribonucleoside termini (U):

| | |
|---|---|
| ET-12R | 5'-GCT AGC CCC TGC TCA TGA GTC TCU |
| CP-1 | 5'-AAA AAA AAA AAA AAA AAA AAU |
| AT-A1 | 5'-CTA CGT GGA CCT GGA GAG GAA GGA GAC TGC CTG U |
| AT-A2 | 5'-GAG TTC AGC AAA TTT GGA GU |
| AT-A3 | 5'-CGT AGA ACT CCT CAT CTC CU |
| AT-A4 | 5'-GTC TCC TTC CTC TCC AGU |
| AT-A5 | 5'-GAT GAG CAG TTC TAC GTG GU |
| AT-A6 | 5'-CTG GAG AAG AAG GAG ACU |
| AT-A7 | 5'-TTC CAC AGA CTT AGA TTT GAC U |
| AT-A8 | 5'-TTC CGC AGA TTT AGA AGA TU |
| AT-A9 | 5'-TGT TTG CCT GTT CTC AGA CU |
| AT-A10 | 5'-CAT CGC TGT GAC AAA ACA TU |

Oligomers containing 5' amine groups were generally reacted with fluorophores, such as Texas Red (TR, excitation 590 nm, emission 610 nm). Sulfonyl chlorides are very reactive towards primary amines forming a stable sulfonamide linkage.

Texas Red-DNA conjugates were made as follows: Texas Red sulfonyl chloride (Molecular Probes) was dissolved in dimethyl formamide (DMF) to a final concentration of 50 mg/ml (80 mM). Oligomer was dissolved in 0.4M sodium bicarbonate, pH 9.0–9.1, to a final concentration of 1 O.D./µl (5.4 mM for a 21-mer). In a micro test tube, 10 µl oligomer and 20 µl Texas Red was combined. Let reaction proceed in the dark for 1 hour. Quench reaction with ammonia or hydroxylamine, lyophilize sample and purify by PAGE (Sambrook et al., 1989, supra).

The following oligomers contain 5'-amino termini:

| | |
|---|---|
| ET-21A | 5'-Amino-TGC GAG CTG CAG TCA GAC AT |
| ET-10AL | 5'-Amino-GAG AGA CTC ATG AGC AGG |
| ET-11AL | 5'-Amino-CCT GCT CAT GAG TCT CTC |
| T-2 | 5'-Amino-TTT TTT TTT TTT TTT TTT T |
| RC-A1 | 5'-Amino-CAG GCA GTC TCC TTC CTC TCC AGG TCC ACG TAG |
| RC-A2 | 5'-Amino-CTC CAA ATT TGC TGA ACT C |
| RC-A3 | 5'-Amino-GGA GAT GAG GAG TTC TAC G |
| RC-A4 | 5'-Amino-CTG GAG AGG AAG GAG AC |
| RC-A5 | 5'-Amino-CCA CGT AGA ACT GCT CAT C |
| RC-A6 | 5'-Amino-GTC TCC TTC TTC TCC AG |
| RC-A7 | 5'-Amino-GTC AAA TCT AAG TCT GTG GAA |
| RC-A8 | 5'-Amino-ATC TTC TAA ATC TGC GGA A |
| RC-A9 | 5'-Amino-GTC TGA GAA CAG GCA AAC A |
| RC-A10 | 5'-Amino-ATG TTT TGT CAC AGC GAT G |

Example 2

Electronically Addressable Microlocations on a Microfabricated Device—Polylysine Method Microlocations were fabricated from microcapillary tubes (0.2 mm×5 mm). The microcapillaries were filled with 18–26% polyacrylamide containing 0.1–1.0% polylysine and allowed to polymerize. The excess capillary was scored and removed to prevent air bubbles from being trapped within the tubes and to standardize the tube length. Capillaries were mounted in a manner such that they shared a common upper buffer reservoir and had individual lower buffer reservoirs. Each lower buffer reservoir contained a platinum wire electrode.

The top surface of the microcapillary in the upper reservoir was considered to be the addressable microlocation. The upper and lower reservoirs were filled with 0.1 M sodium phosphate, pH 7.4 and prerun for 10 minutes at 0.05 mA constant using a BioRad 500/1000 power supply. About 2 μl (0.1 O.D.) of periodate oxidized ET-12R capture sequence was pipetted into the upper reservoir with the power on and electrophoresed for 2–5 minutes at constant current. The ET-12R capture sequence becomes concentrated and immediately covalently bound to the primary amines on the microlocation surface. The polarity was then reversed so that the test capillary was now biased negative and electrophoresed an additional 2–5 minutes. Any remaining unbound DNA were repulsed while the covalently attached DNA remained at the microlocation.

The upper reservoir was aspirated and rinsed with buffer. The apparatus was disassembled and a fresh reference test device was mounted. The reservoir was refilled and fluorescently labeled complement DNA sequence added, i.e., ET-10AL-TR. The oligomer was electrophoretically concentrated at the positively biased test microlocation for 2–5 minutes at 0.05 mA constant current. The polarity was reversed and unbound complement removed. The test devices were removed and examine by epifluorescence microscopy. A negative control for non-specific binding was performed as described above substituting a non-complementary DNA sequence ET-21-A-TR for ET-10AL-TR.

The cross-section of the capillary microlocations surfaces were examined under a Jena epifluorescent microscope fitted with a Hamamatsu ICCD camera imaging system. The fluorescent analysis results indicated that complement ET-10AL-TR hybridized to the binding entity/capture sequence and remained hybridized even when the potential was biased negative. The ET-21A-TR non-complement was not retained at the test device surface when the potential was reversed.

Example 3

Electronically Addressable Microlocations on a Microfabricated Test Device—Succinimidyl Acrylate Method This example describes an alternative attachment chemistry which covalently binds the 5'-terminus of the oligonucleotides. Capillaries were fabricated as described above except that 1% succinimidyl acrylate (Molecular Probes) was substitute for the polylysine. The capillaries were made up fresh because the succinimidyl ester used to react with primary amines is relatively labile, especially above pH 8.0. The capillaries were mounted as described above and the reservoirs were filled with 0.1 M sodium phosphate, pH 7.4. The capillaries were prerun for 10 minutes at 0.05 mA. About 2 μl ET10AL (0.1 O.D.), which contains a 5'-amino terminus, was pipetted into he upper reservoir with the power on and electrophoretic transport carried out for 2–5 minutes. The polarity was reversed so that the test devices were biased negative and electrophorese an additional 2–5 minutes. The un-bound DNA is repulsed while the covalently attached DNA remained at the microlocation.

The upper buffer reservoir was aspirated and rinsed with buffer. The reference test device was un-mounted and a new reference device mounted. The reservoir was refilled and the fluorescent labeled complement oligomer, ET-l 1AL-TR was added and electrophorese as described above. A negative control for non-specific binding was performed as described above substituting a non-complement DNA sequence ET-21A-TR for ET-11AL-TR.

Fluorescent analysis of each of the test devices showed that the complement ET-11AL-TR hybridized to the capture sequence (ET-10AL ), and remained hybridized even when the potential was changed to negative. The non-complementary sequence, ET-21A-TR was not retained at the microlocation when the potential was reversed.

Example 4

Electronically Controlled Fluorescent DNA/Dye Detection Process

Certain dyes such as ethidium bromide (EB) become highly fluorescent when bound (intercalated) into double-stranded DNA. While the fluorescence and binding affinity is greater when bound into double-stranded DNA; the dye also has some affinity for single-stranded DNA and produces low level fluorescence when bound. The following example shows how an electronically controlled DNA/Dye detection process can be developed.

Microcapillary test devices were prepared and hybridized as described in Example 2 and 3. Ethidium bromide (EB) was added to the buffer solution (~0.05mM EB final concentration) and the test devices were biased negative to concentrate EB (positively charged) at both the hybridized and un-hybridized microlocations. The test devices were observed by epifluorescece microscopy at 550 nm excitation and 600 nm emission. Both the hybridized and un-hybridized microlocations showed intense red fluorescence from the concentrated EB.

The test devices were re-mounted biased positive constant current at 0.05 mA for 0.03 Volt-Hours, to selectively remove the EB. Fluorescence at the un-hybridized microlocations diminished while the hybridized microlocations retained a very high level of EB fluorescence. The results are given below:

| Capture | Target | Normalized Signal |
| --- | --- | --- |
| ET-10AL | ET-11AL (Pos.) | >200 |
| ET-10AL | ET-21A (Neg.) | 1 |

Fluorescent signal was measured using an ICCD imaging camera system and represent peak fluorescent intensities. The signal to noise ratio would be more than 1000 fold if the entire fluorescent signal area was integrated. This demonstrates a method for increasing signal to noise ratios and the dynamic range of the DNA assays using intercalculating dyes.

Example 5

Active Programmable Electronic Matrix (APEX)— Micro-Machine Fabrication

A radial array of 6 addressable 250 μm capillary locations was micro-machined from plastic substrate material. The device has a common upper reservoir and separate lower reservoirs such that each microlocation is individually addressable. A unique oligomer sequence binding entity is localized and attached to a specific microlocations made from highly crosslinked polyacrylamide by the methods described previously. The test microlocation has a positive potential while the other microlocations have negative potentials to prevent non-specific interactions.

The array is washed and then hybridized with a complementary fluorescently labeled DNA probe. The array is washed to remove excess probe and then observed under an epifluorescent microscope. Only the specifically addressed microlocation are fluorescent. The process is repeated with another binding entity at another location and verified by hybridization with a probe labeled with another fluorescent moiety.

DNA sequences are specifically located to predetermined positions with negligible crosstalk with the other locations. This enables the fabrication of micromatrices with several to hundreds of unique sequences at predetermined locales.

To select appropriate plastic substrates of low fluorescent background, different plastic substrates were tested as to their fluorescent characteristics at 600 nm. The plastics were tested by an epifluorescent microscope imaging system and by a fluorometer. The following table provides the list of substrates and fluorescent readings obtained from an LS50B fluorometer:

| Plastic Substrate | Intensity at 610 nm, 5 sec int. |
| --- | --- |
| ABS | |
| black | 0.140 |
| white | 6.811 |
| Polystyrene | 7.955 |
| Acrylic | |
| clear | 0.169 |
| white | 51.77 |
| tinted | 0.151 |
| black | 0.035 |
| transwhite | 51.22 |
| UHMW | |
| black | 0.743 |
| white | |
| Delrin | |
| black | 1.834 |
| white | 61.39 |
| TFE | 96.05 |
| Polypropylene | |
| white | 22.18 |
| natural | 25.82 |
| Polycarbonate | |
| clear | 11.32 |
| tinted | 3.103 |
| white | 45.31 |
| black | 0.156 |
| PVC | |
| gray | 2.667 |

The experiments show that black acrylic, ABS, and polycarbonate have the lowest fluorescence background levels.

Example 6

Active, Programmable Electronic Matrix (APEX) Microlithographic Fabrication

An 8×8 matrix (64 sites) of 50 µm square microlocations on a silicon wafer (see FIG. 3) was designed, fabricated and packaged with a switch box (see Device Fabrication Section for details). Several materials and process improvements, as described below, were made to increase the selectivity and effectiveness of the APEX DNA chip device.

6a) Selection of Topcoat

The APS (3-aminopropyltriethoxysilane) process involves reacting the entire surface of the chip. Selectivity of this initial functionalization process is dependent on the relative reactivities of the various materials on the chip surface. In order to reduce functionalization and subsequent DNA attachment to the areas surrounding the microlocations, a material that is less reactive to APS than $SiO_2$ or metal oxide is needed. Photoresists and silicon nitride were tested. The different topcoats were applied to silicon dioxide chips. The chips were examined by epifluorescence and then treated with APS followed by covalent attachment of periodate oxidized poly-A RNA sequences (Sigma, M 100,000). The chips were hybridized with 200 nM solution of Texas Red labeled 20-mer (T2-TR) in hybridization buffer, for 5 minutes at 37° C. The chips were washed 3 times in washing buffer and once in 1×SSC. The chips were examined by fluorescence at 590 nm excitation and 610 nm emission.

Silicon nitride was chosen because it had much less reactivity to APS relative to silicon dioxide and was not inherently fluorescent like the photoresist materials tested. Other methods such as UV burnout of the background areas are also possible.

6b) APEX Physical Characterization

A finished matrix chip was visually examined using a Probe Test Station (Micromanipulator Model 6000) fitted with a B & L microscope and a CCD camera. The chip was tested for continuity between the test pads and the outer contact pads. This was done by contacting the pads with the manipulator probe tips which were connected to a multimeter. Continuity ensures that the pads have been etched down to the metal surface. The pads were then checked for stability in electrolytic environments. The metal wires were rated to handle up to 1 mA under normal dry conditions.

A drop (1–5 µl) of buffered solution (1×SSC) was pipetted onto the 8×8 matrix. Surface tension keeps the liquid in place leaving the outer contact pad area dry. A probe tip was contacted to a contact pad and another probe tip was contacted with the liquid. The current was incrementally increased up to 50 nA at maximum voltage of 50 V using a HP 6625A power supply and HP3458A digital multimeter.

The initial fabrication consisted of the silicon substrate, a silicon dioxide insulating layer, aluminum deposition and patterning, and a silicon nitride topcoat.

The second fabrication process included a silicon dioxide insulating layer between the aluminum metal and silicon nitride layers. Silicon dioxide and Al have more compatible physical properties and form a better chemical interface to provide a more stabile and robust chip than that made by the initial fabrication process.

6c) DNA Attachment

An 8×8 matrix chip was functionalized with APS reagent as described in Example 5. The chip was then treated with periodate oxidized poly-A RNA (Sigma, average M 100, 000). The chip was washed in washing buffer (WB) to remove excess and unbound RNA. This process coated the entire chip with the capture sequence, however there is a much higher density at the exposed metal surfaces than at the nitride covered areas. The chip was hybridized with a 200 nM solution of T2-TR in hybridization buffer (HB) for 5 minutes at 37° C., and then washed 3 times in WB and once in 1×SSC for one minute each at ambient temperature. The chip was,examined by fluorescence at 590 nm excitation and 610 nm emission.

The opened metal areas were brightly fluorescent and had the shape of the 50µ square pads (microlocations). Low fluorescent intensities and/or irregular borders would suggest that some pads were not completely opened. Additional plasma etch times would be recommended in these cases.

6d) Electronically Controlled Hybridization

Active hybridization was performed by using a chip from Example 8c and biasing one specific microlocation positive. This was done by using the switch box which would also automatically bias the remaining microlocations negative or by using an electrode in the external solution. Three microliters of buffer was deposited on the matrix pads (microlocations) only. A current, ~1–5 nA, was applied for several seconds and 0.1 pmole of T2-TR was added to the solution. The liquid was removed and the chip was dried and examined for Texas Red fluorescence at Texas Red at excitation 590 nm and emission 610 nm. Only the specific microlocation biased positive was fluorescent. This experiment can be repeated many times, using other specific microlocations on the APEX chip. Additionally, the fluorescence DNA at one microlocation was electronically de-hybridized and translocated to another microlocation by biasing the initial location negative and the destination microlocation positive.

6e) Electronically Controlled Addressing and Device Fabrication

The 8×8 APEX matrix was functionalized with APS as described previously. The oligonucleotide binding entity CP-1 was activated by periodate oxidation method. Four microlocations were biased positive in the matrix and the remainder were biased negative. Two microliters of buffer was deposited on the matrix and a current was applied. The binding entity, CP-1, was added and electronically to concentrate at the designated locations. The liquid was removed, the chip was rinsed briefly with buffer and two microliters of buffer was deposited on the chip. Again, current was applied for several seconds and 0.1 pmole of T2-TR was added. The liquid was removed after a short time and the entire chip was washed in WB, 3 times. The chip was dried and examined for fluorescence.

Results indicate that the four positively biased microlocations were all fluorescent. This example demonstrates the selective addressing of microlocations with a specific binding entity, the localization and covalent coupling of attachment sequences to the microlocations, and the specific hybridization of complementary target sequences to the derivatized microlocations.

6f) Genetic Typing APEX Chip

DNA binding entities with 3'-ribonucleoside termini are synthesized which are specific for the polymorphisms of HLA gene dQa. The binding entities are activated by periodate oxidation as described previously. The reverse complements are synthesized with 5'-amino termini and are conjugated with fluorophores, such as Texas Red, Rhodamine or Bodipy dyes, as described previously. The microlocations are functionalized with primary amines by treatment with APS, as described previously.

Several microliters of solution are placed over the 8×8 matrix. A specific microlocation is addressed by biasing that microlocation positive, the periodate oxidized DNA oligomer is added, ~0.1 pmole, and is translocated and covalently coupled to that location. The polarity is reversed and the un-bound binding entity molecules are removed. This is repeated for another binding entity at another addressed microlocation until all the unique binding entities are bound to the chip.

The chip is then hybridized to individual fluorescently labeled complement sequences to determine the specificity of the coupling reaction as well as to visualize all addressed microlocations at once.

On the same chip which is electronically denatured to remove complementary oligomers (10 minutes at 90° C. in 0.05% SDS), the addressed microlocations are hybridized with un-labeled target DNA or genomic DNA. Detection is via the fluorescent dye detection assay as described previously in the specification.

Results will demonstrate that microlocations are specifically addressed with unique binding entities. Non-specific binding to negatively biased microlocations will be negligible. The device and associated binding entity chemistry is stable under denaturation conditions, thus making the addressed and fabricated device reusable. Electronic methods for denaturing the hybrids would be to increase the current and/or increase the time it is applied.

Example 7

Electronic Stringency Control (7A) Single Point Mutation With 15 mer RAS-12 Probes The ability of the device to affect a high level of electronic stringency control was demonstrated with a Ras-12 oncogene model system using 15-mer probes. A single base pair mis-match in a DNA duplex causes only a slight instability in the hybrid pair relative to the matched duplex. This slight instability causes the mis-matched duplex to denature at a slightly lower Tm than the matched duplex. When the pairs (match and mis-match) are both hybridized at optimal stringency for the matched pair, the mis-matched pair will hybridize with less efficiency. The hybridization signal from the mis-match will be somewhat less than the signal from the matched pair. With conventional hybridization procedures, single point mutation analysis an be carried out with probes in the 8-mer to 2 1-mer range. Probes in the 10-mer to 20-mer range are used most often. When mutation specific probes become shorter than 8-mers or longer than 20-mers, it becomes extremely difficult to discriminate the match from the mis-match in any reliable manner. This is because there is little difference in the hybridization signals between the match and mis-match pairs. The traditional methods of hybridization stringency control used in point mutation analysis rely on temperature and salt concentrations. We have found that stringency control can also be affected by the electrophoretic potential.

In the Ras-12 example, 15-mer point mutation specific probes were electronically hybridized to 30-mer target sequences attached to the microlocations on test devices. The polarity at the microlocations was biased negative, and the hybrids were subjected to constant current for a given time, providing a defined power level which denatures the mis-match without affecting the perfect match.

The following sequences were synthesized and tested on a set of three test structures, each with a 250 μm surface location. The underlined/bold faced base indicates the mis-match position.

The attachment sequences were:

Ras-G 5'- GGT GGT GGG CBC CGB CGG TGT GGG CAA GAU-3'-microlocation

Ras-T 5'- GGT GGT GGG CGC CGT CGG TGT GGG CAA GAU-3'-microlocation

The reporter probe sequences (labelled with Texas Red) were:

Ras-1 3'-CC-GCG-GCC-GCC-ACA-C-5'-(TR)

Ras-2 3'-CC-GCG-GCA-GCC-ACA-C-5'-(TR)

Ras-3 3'-CC-GTG-GCA-GCC-ACA-C-5'-(TR)

Test devices were fabricated from microcapillary tubes as described previously in the specification. Attachment sequences Ras-G and Ras-T were periodate oxidized and covalently bound to the addressed microlocations.

Ras-G microlocation were then hybridized with Ras-1, Ras-2 or Ras-3. Ras-1 is the perfect match to Ras-G. Ras-2 is a one base pair mismatch (G-A). Ras-3 is a two base pair mismatch (G-A and G-T). The G-A mis-match produces the least destabilization to the DNA duplex, and is therefore the most difficult to distinquish from the perfect match.

Conventional hybridization was first carried out and the microlocations were examined fluorescently to measure to what extent complementary sequences were hybridized. The test devices (microcapillaries) were re-mounted and electronic hybridization was then carried out. The test devices were all subjected to the same electronic stringency by biasing them at a negative potential (at constant current) until the mis-matched hybrids were completely removed without significantly affecting the perfectly matched hybrid. The procedure and results are shown below:

Conventional Hybridization Procedure:

Hybridize in 5×SSC for 15 minutes at 40° C.

Wash 3 times in 1×SSC for 5 minutes each 20° C.

Carry out fluorescent analysis

Observed signal ratio of perfect match (Ras-G/Ras-1) to 1 bp mis-match (Ras-G/Ras-2): about 10 to 1

Electronic Stringency Control (ESC) Procedure:

Hybridize in 5×SSC for 5 minutes at 200 ° C.

"No washing procedure"

Apply an electronic stringency of 0.15 milliamps (MA) at 150 volts (V) for 4 minutes (20° C.)

Carry out fluorescent analysis

Observed signal ratio of perfect match (Ras-G/Ras-1) to 1 bp mis-match (Ras-G/Ras-2): >100 to 1

The complete results for all the experiments are shown graphically in FIG. (15). These results show that it is not only possible to use electrophoretic potential for for stringency control in DNA hybridization reactions; but also show that ESC provides both higher hybridization efficiencies and higher discrimination ratios than conventional hybridization procedures. In addition, ESC can be applied to each individual microlocation, providing independent stringency control in the same bulk solution.

(7B) Single Point Mutation Analysis using 7-mers and 22-mer Probes

Both 7-mer and 22-mer probes, which are well outside the normal size range commonly used in point mutation analysis, were prepared to further demonstrate the advantages of electronic hybridization and ESC. The point mutation specific oligomer probes listed below can be paired such that resulting hybrids have 0, 1, or 2 base mis-matches. Complementary oligomer sequences were coupled to microlocations and hybridized as described above. The polarity at the microlocations was reversed (biased negative) and the hybrids subjected to constant current for a given time, providing a defined power level to denature the mis-matches without removing the perfect match.

The Ras-G or Ras-GA oligomers (shown below) were attached to microlocations and used as target sequences. The series of 22-mer and 7-mer Ras specific oligomer shown below were labeled with Texas Red fluorophore as described elsewhere in the specification. The "underlined and bold faced" bases indicates the mismatched and/or potential mismatched positions:

| Ras-G | 5'-GGT GGT GGG CGC CGG CGG TGT GGG CAA GAU |
|---|---|
| Ras-GA | 5'-Amino-GGT GGT GGG CGC CGG CGG TGT GGG CAA GA |
| Ras-22C-TR | (TR)-5'-TGC CCA CAC CGC CGG CGC CCA C |
| Ras-22A-TR | (TR)-5'-TGC CCA CAC CGA CGG CGC CCA C |
| Ras-TA | (TR)-5'-TGC CCA CAC CGA CGG TGC CCA C |
| Ras-7C | (TR)-5'-ACA CCG C |
| Ras-7A | (TR)-5'-ACA ACG C |

Test devices were fabricated from microcapillary tubes as described previously in the specification. The oligomer target sequences Ras-G or Ras-GA were covalently attached to the microlocations. One microlocation was then hybridized with the Texas Red labeled perfect 22-mer complement Ras-22C-TR. A second microlocation was hybridized with Ras-22A-TR, a 22-mer one base pair mis-match (G-A); or the Ras-22-TA the 22-mer two base pair mis-match (G-A and G-T).

The test devices, as described above in the specification, were run concurrently and in the dual channel mode where both microlocations experience the same current or power levels simultaneously. The test devices were first hybridized by convention procedures and the microlocations examined fluorescently to determine the amount of complementary sequences which had hybridized. The test devices were then used to carry out electronic hybridization to controlled time at constant current until the mis-matched hybrids were removed without significantly affecting the perfectly matched hybrids. A Bio-Rad 1000/500 power supply was typically set to 0.02 to 0.1 mA and the experiments were run at constant current for 0.02 to 0.04 volt-hours. The device was disassembled and the test devices were observed by epifluorescence on a Jena microscope fitted with a silicon intensified CAD camera (Hamamatsu). The images were processed by a Hamamatsu Argus 10 image processor and recorded by a Sony Video Printer. The capillaries were re-run when additional electronic stringency was required.

Single base pair mis-match discrimination was performed on the 7-mers as described above. However, due to the lower Tm, the device was run in a cold box at 4–6° C. rather than at room temperature.

Results indicated that electronic hybridization and stringency control could discriminate single base pair mis-matches in 7-mers and 22-mers. The match:mismatch ratios are 100:1 or greater. This signal:noise ratio was generally better than what was reported by any hybridization methods which use temperature and ionic strength to control stringency conditions.

Electronic stringency control was able to distinguish a one base G-A mismatch from the perfect match eventhough the G-A mismatch is the most stable mismatch because the G imino proton can participate in hydrogen bonding with A which can stabilize the duplex.

Power dissipation calculations and measurements showed negligible changes in temperature, demonstrating that the stringency was not caused by temperature changes at the microlocations. Microlocations which were passively hybridized as described above (not subjected to a electronic hybridization) showed no discrimination between match and mis-match demonstrating that diffusion was not causing the discrimination.

These examples also demonstrate that each microlocation can have individual stringency control, and thus overcome a major obstacle to large scale multiplex hybridization techniques which are limited to a single common stringency level. It is also possible to correlated electronic stringency power levels with thermal melting (Tm) data to generate a predictive electronic melting (Em) curves and equations.

(7° C.) Electronic Hybridization in High Genomic Background

Actual target DNA sequences usually make up only a very small proportion of the total DNA in a genomic DNA sample. By concentrating total DNA at a very small location on an APEX device, this invention increase the efficiency of target hybridizations in the presence of an excess of heterologous DNA.

In this example, attachment sequences bearing a 5'-amine groups were attached to test devices containing 22% PAGE, 1% succinimidyl acrylate. The capillaries were derivatized with either ET-23AL or ET-11AL capture sequences. The target probe ET-12R was labelled with Texas Red. ET-12R-TR would hybridize to ET-23AL but not to ET-11AL capture sequences, the test and the control, respectively.

The heterlogous genomic DNA, calf thymus DNA (CT DNA, Sigma), was dissolved to a final concentration of 1 mg/ml water, sonicated and heated to denature the DNA. Samples were prepared in 0.5× TBE containing $10^{10}$ copies of ET-12R-TR target with 0, 0.1 μg, or 1.0 μg of denatured CT DNA in a final volume of 100 μl. This represented a 0, 1,000, or 10,000 fold excess of CT DNA relative to target DNA.

Test devices were pre-run 5 minutes at 0.03 mA in 0.5× TBE using a Bio-Rad 1000/500 power supply. The device was set to run in dual channel mode so that a test and control capillary could be run at the same time under exactly the same conditions. The sample was applied (100 μl) and the capillaries were biased with a positive potential to attract DNA for 5 minutes at 0.03 mA. The polarity was reversed and the same power was applied to remove all un-hybridized ET-12R-TR target from the test device surface. The buffer was aspirated and the test devices were observed by epifluorescence on a Jena microscope fitted with a silicon intensified CAD camera (Hamamatsu). The images were processed by a Hamamatsu Argus 10 image processor and recorded by a Sony Video Printer.

There was no difference between the absolute hybridization signal and the signal/noise ratios in the presence and absence of 0.1 μg CT DNA per 100 μl. The signal intensity was equivalent and the signal was uniformly distributed across the active area.

At the level of 1 μg CT DNA per 100 μl, the signal was predominantly distributed around the perimeter of the capillary, suggesting that the capture sequences were blocked or saturated. This artifact was easily surmounted by oscillating the polarity during the hybridization step. This would pulse the total DNA towards and away from the active area, allowing the target to hybridize more efficiently and uniformly.

(7D) Passive Hybridization vs. Electronically Controlled Hybridization

Electronically controlled hybridization is more efficient and faster than passive hybridization because of the concentration effect in the electronically controlled hybridization.

Microcapillary test devices were made with ET-23AL and ET-11AL attachment sequences, as test and control devices, respectively. A hybridization solution contains $1 \times 10^{10}$ copies of ET-12R-TR with 1 μg CT DNA in a total volume of 100 μl was made up.

Passive hybridization:

A set of test and control devices were placed in a small test tube with 100 μl of hybridization solution at 50° C., and hybridized for 15 minutes. The samples were then washed 3 times in 1× SSC, 0.1% SDS, 5 minutes for each wash at 45° C.

Electronically controlled hybridization:

Test devices were mounted and pre-run for 5 minutes at 0.06 mA. The buffer was then aspirated and 100 μl of hybridization solution was added. The test devices were biased positive for 3 minutes at 0.06 mA. the polarity was then reversed for 30 seconds, and reverse again so the test devices were once again positive for additional 3 minutes. The test devices were biased negative for 3 minutes to electronically wash.

The efficiency and extent of hybridization was significantly better with the active format than with the passive format. Absolute signal in the active (electronic) format was more than 100 fold higher than the signal in the passive format. The signal/noise ratio in the active format was increased 10 fold over the signal in the passive format. The active hybridization assay was completed in under 10 minutes with minimal manipulation. The passive format required ~30 minutes with several manipulations of tubes and buffers.

Traditional hybridization methods use 2.5 nM probe and 3 times $C_n t$, for 15 minutes, for 90% completion of the reaction. At our experimental concentration of 0.17 nM probe, the passive hybridization reaction kinetics would normally require ~4 hrs.

Active hybridization enables the use of lower probe concentrations which result in lower background. Traditional methods depend on diffusion and thus must use higher probe concentrations to drive the reaction kinetics. The active method is able to concentrate the sample into a very small volume which results in a very high local probe concentration and subsequently very fast hybridization reaction kinetics.

Example 8

Hybridization with Fluorescent DNA Nano-Structure

Normally, the overall sensitivity for non-amplification type hybridization assays is limited by background from the non-specific binding. This is often a major problem when multiple reporter groups, or secondary complexes with multiple reporter groups, are used to label DNA probes. Therefore, the assay detection limit is often reached well before the actual or intrinsic detection limit of the reporter label(s) is reached.

Using electronic controlled hybridization methods, we have found that highly fluorescent sub-micron or nano-scale beads may be used with attached DNA probes for ultrasensitive assays. We have been able to control the movement of DNA probe-fluorescent nanostructures using free field electrophoresis. Since electronic stringency control provides high level discrimination of hybridized from un-hybridized structures, DNA probe-fluorescent nanostructures can significantly increase hybridization sensitivity. Electronic stringency control allows us to utilize these highly fluorescent nanostructures or other multiple labeling scenarios for low copy number (50 to 1000 targets) detection, without any amplification being necessary. To date, this has not been possible with conventional hybridization methods and procedures.

Fluorescent nanoparticles, Fluorospheres, were obtained from Molecular Probes, Inc. The particles are composed of carboxymethyl latex spheres loaded with fluorescent dyes, such as Texas Red or fluorescein. The latex spheres could be obtained with different functional groups, such as amine or aldehydes. The particles are available in sizes from 0.01 to 5 µm in diameter.

1) Characterization of the Fluorescent Nanoparticles

The nanoparticles, unmodified, amine modified, or aldehyde modified, have a net positive charge. In an electric field these particles migrate towards the negatively biased microlocations.

2) DNA Attachment Chemistry to the Fluorospheres

The amine modified particles can be coupled to nucleic acids bearing terminal aldehyde groups. The latter can be generated by DNA probes synthesized with a 3'- terminal riboside which is subsequently oxidized by the periodate method as described previously in the specification.

The particles are stored as a 2% suspension in distilled water. An aliquot of 25 to 50 µl of the 0.02 –1.0 µm amine modified red fluorescent Fluospheres was pelleted and re-suspended in 0.1M sodium phosphate, pH 7.4. An excess of periodate oxidized poly ribo-A was added to the suspension. The reaction was allowed to incubate for 90 minutes at room temperature. The particles were washed and pelleted several times in 1× SSC, 0.1% SDS (0.15 mM sodium chloride, 0.015 mM sodium citrate, 0.1% (w/v) sodium docecyl sulfate, pH 7.0) to remove unbound and nonspecifically bound poly ribo-A.

The DNA-fluorospheres in buffered solution were placed in a direct current electric field. It was observed that the DNA-Fluorospheres migrated towards the positive electrode, indicating that the net charge was now negative. This is a simple and convenient method to determine if the coupling reaction was successful. Traditional hybridization methods would require using a radiolabeled reporter probe because the intense fluorescence from the particles would obscure any hybridization signal.

3) DNA Attachment to Test Devices

The test devices were polymerized with highly cross-linked polyacrylamide, containing 1% succinimidyl acrylate, which can be subsequently reacted with 5'- amine terminated DNA probes. The attachment of the capture sequence, oligo-T, was verified by hybridization with fluorescently labeled complement probe, CP-1-TR. The test device surfaces were highly fluorescent which indicates that the surface was derivatized with capture sequences.

4) Electronic Hybridization and Detection of DNA-Fluorospheres

The hybridization reactions were performed in a structure which holds 2 microcapillary test devices sharing a common upper reservoir and independent lower reservoirs. The reactive surfaces are exposed to the common upper reservoir.

The test devices were mounted in the structure and pre-run in 0.5× TBE at 0.05 mA, for 15 minutes. One test device had the T2 complementary attachment sequences, and the other capillary had ET-10AL non-complementary attachment sequences. One microliter of DNA-fluorospheres at was added to the upper reservoir. The test devices were biased positive at 0.02 mA, for 5 minutes to attract the DNA-Fluorospheres (fluorescent nanoparticles). The test devices were inspected to determine that the particles were present on the surface. The polarity was reversed such that the test devices were biased negative and the un-hybridized DNA-Fluorospheres should be repelled.

There was no discrimination between the test capillary and the control devices. The particles could not be removed after repeated attempts regardless of the amount of power applied.

5) Passive Hybridization and Detection of DNA-Fluospheres

Without being bound by any theory or hypothesis, we believe that electronic hybridization of the particles physically embeds or traps the particles in the surface gel matrix of the test devices. Thus, DNA-Fluorospheres which are passively hybridize to the attachment sequences on the gel surface, should be more easily removed by electronic de-hybridization.

New test devices was mounted as described above. A 0.05% suspension of DNA-Fluorospheres were pipetted into the upper reservoir and passively hybridized for 5 minutes. The buffer was aspirated and fresh 1× TBE buffer was added. The test devices were now biased negative to repel the particles. The test device was operated for 5 min at 0.02 mA and then inspected by fluorescence.

There was now significant discrimination between the test and control capillary after performing ECS for a total of 10 minutes at room temperature. The signal was not uniformly distributed across the test surface, but concentrated in signal pockets. This may suggest that the availability of the surface attachment sequences is limited. Improvements can be made using longer spacer arms with either hydrophobic, hydrophilic, or mixed character. Such spacers for example can be built using diaminohexane and succinic anhydride, and a variety of other spacer groups well known in art.

Example 9

Electronically Directed Restriction Enzyme Cleavage of Specific ds-DNA Sequences Two examples are used to demonstrate the ability of APEX devices to selectively carry out restriction endonuclease cleavage of ds-DNA sequences. The M13mp18 (having a Xba I restriction site) and M13mp8 (not having Xba I restriction site) vectors are used in these examples. These vectors are commonly used in many cloning and DNA sequencing procedures.

The first example demonstrates: (1) the electronic hybridization of M13mp sequences to specific microlocations on the test device, (2) the free field electrophoretic transport of the Xba I restriction enzyme to the microlocations, and (3) the subsequent capture of the cleaved fragments at other microlocations. The example also demonstrates the ability of the device to self-assemble itself with specific binding entities (oligonucleotide capture sequences).

The basic steps in the procedure are shown in FIG. (16). Four specific microlocations (ML-1, ML-2, ML-3, and ML4) which covalently bind oligonucleotide capture sequences are used in the procedure. Electronic delivery systems are used to deliver reagents (oligonucleotides, restriction enzyme, etc.) and for disposal of reactants.

The first step involves the transport and covalent attachment of the M13-1 oligonucleotide capture sequence to ML-1 and ML-2 microlocations, and the transport and attachment of the M13-2 oligonucleotide capture sequence to ML-3 and MI-4 microlocations. Since nucleic acids are negatively charged at pH>4, they always move toward the positively charged electrode when electrophoresed in buffer solutions which range from pH 5–9.

The second step involves the free field electrophoretic transport and hybridization of the M13mp18 sequence to the M13-1 capture sequence at ML-1 microlocation, and the M13mp8 sequence to the M13-1 sequence at the ML-2 microlocation.

The third step involves the transport of the XbaI restriction enzyme to the ML-I (M13mp18) microlocation and the ML-2 (M13mp8) microlocation. The Xba I cleaves the M13mp18 at ML-1, but not the M13mp8 at ML-2. The cleaved fragments from ML-1 are transported and hybridized to the M13-2 sequence at ML-3. As an experimental control, free field electrophoresis is carried out between ML-2 and ML4. Since the M13mp8 sequence at ML-2 has not been cleaved, no fragment is detected at ML-4.

The various M 13 attachment and probe sequences used in this example are prepared as previously described in the specifications. These sequences are shown below:

| M13-C1 | 5'-CCA GTC ACG ACG TTG TAA AAC GAC GGC CAG U |
| M13-C2 | 5'-GTA ATC ATG GTC ATA GCT GTT TCC TGT GTG U |
| MP18-40C | 5'-GCA TGC CTG CAG GTC GAC TCT AGA GGA TCC CCG-GGT ATT C |
| M8-40C | 5'-TGC CAA GCT TGG CTG CAG GTC GAC GGA TCC-CCG GGT ACC G |
| M18-R1 | (TR)-5'-AAA TTG TTA TCC GCT CAC AAT TGC |
| MP8-R2 | (F)-5'-ACA CAA CAT ACG AGC CGG AAG CAT |

Step 1—Attachment of M13 Capture Sequences

An APEX test device with 200 μm microlocations of amine activated high-crosslinked (26%) polyacrylamide surface or polycarbonate (5–10 nm) porous membrane surface is used for this procedure.

The M13-C1 capture sequence is a 31-mer DNA oligonucleotide containing a 3'-ribonucleotide. The M13-C1 sequence is complimentary to the 3'-terminal of the M13mp18 and M13mp8 single-stranded (+) vectors. The M13-C1 capture sequence is designed to hybridize and strongly bind all The M13-C2 sequence is a 31-mer oligonucleotide containing a 3'-ribonucleotide. The M13-C2 is complementary to a portion of the M13 sequence upstream from the cloning site containing the Xba I restriction site. The M13-C2 capture sequence is designed to hybridize and strongly bind the Xba I cleaved M13 fragments.

The M13-C1 and M13-C2 capture sequences are activated for coupling to the amine derivatives on the APEX microlocations by the paraded oxidation. The 3' ribonucleotide terminus is converted to a terminal dialdehyde by the paraded oxidation method which can react with primary amines to form a Schiff's base.

Reaction conditions are as follows:

Dissolve 10-20 O.D. of the M13-C1 or M13-C2 oligomer in water to a final concentration of 1 OD/μl. Add 1 volume of 0.1M sodium acetate, pH 5.2 and 1 vol 0.45M sodium paraded (made fresh in water). Stir and incubate reaction for at least 2 hours at ambient temperature, in the dark. Load reaction mix onto a Sephadex G-10 column (pasteur pipette, 0.6×5.5 cm) equilibrated in 0.1M sodium phosphate, pH 7.4. Collect 200 μl fractions, spot 2 μl aliquots on thin layer chromatography (TLC) and pool ultra violet (UV) absorbing fractions.

Four top surfaces of the APEX test devices are designated to be the addressable microlocations ML-1, ML-2, ML-3, and ML-4.

M13-C1 is covalently attached to the ML-1 and ML-2 microlocations by the following procedure:

The upper and lower reservoirs are filled with 0.1 M sodium phosphate, pH 7.4 and prerun for 5 minutes at 0.05 mA constant current, using a BioRad 500/1000 power supply. The tip of an electronic delivery system containing ~0.1 O.D. units of the paraded oxidized M13-C1 oligonucleotide is placed into the lower reservoir. The electronic delivery system is a specially modified plastic pipet tip with a platinum electrode inside. The electronic delivery system is biased negative (−) and microlocations ML-1 and ML-2 are biased positive (+) at 0.1 mA. M13C-1 is electrophorese to ML-1 and ML-2 for 2 minutes at constant current, where it becomes covalently bound to the surface. The polarity is reversed, for ~4 minutes, so that un-reacted M13C-1 is removed from the ML-1 and ML-2 microlocations.

The M13C-2 sequence is attached to the ML-3 and ML4 microlocations with the same procedure described above.

Step 2—Hybridization of M13 Vectors, Complementary Sequences, and Fluorescent Reporter Probes Since restriction endonucleases require double-stranded DNA for cleavage, the cloning/restriction site segments of the single stranded M13mp18 (from 6240 to 6280) and M13mp8 (from 6230 to 6270) must be hybridized with complementary DNA sequences. Electronic hybridization is used to hybridize a 40-mer complementary fragment (MP18-40C sequence) to M13mp18 vector on ML-2/M13C-1 microlocation; and to hybridize a 40-mer complementary fragment (MP8-40C sequence) to the M13mp8 vector on ML-2/M13C-1 microlocation respectively.

Electronic hybridization is carried out by negatively (−) biasing an electronic delivery system containing 0.05 O.D. units of M13mp18, and positively (+) biasing the ML-1/MP13C-1 microlocation at 0.1 mA for 2 minutes. The polarity is reversed for 4 minutes and the un-hybridized M13mp18 is removed from the microlocation. The same procedure is used to electronically hybridize the M13mp8 vector to the ML-1/M13C-1 microlocation.

The M13mp18 and M13mp8 sequences are then electronically hybridized with two different fluorescent reporter probes. The M13mp18 vector on the ML-1/M13C-1 microlocation is electronically hybridized with a 24-mer Texas Red labelled reporter probe (MP18R-1 sequence), which hybridizes to the 5'-terminal of the cloning/restriction sites. The M13mp8 vector is electronically hybridized with a 24-mer Fluorescein labelled reporter probe (MP8-R2 sequence), which hybridizes to the 5'-terminal of the cloning/restriction sites.

Step 3—Restriction Cleavage of the M13mp18 Vector Using the Xba I Restriction Enzyme Depending upon their Isoelectric Point (pI), many proteins and enzymes can be negatively charged (pH>pI), neutral (pH=pI), or positively charged (pH<pI) in the pH 5–9 range. A number of restriction endonucleases have pI's in the 6–7 range. At pH's greater than the pI, these enzymes will carry a net negative charge. Therefore, when free field electrophoresis is carried out in a buffered solution with a pH>7, these enzymes will migrate to the positively charged microlocation.

In the case of many DNA modifying enzyme, like restriction endonuclease, it is always desirable to choose a buffer solution which provides a pH which balances the optimal enzyme activity with relatively fast electrophoretic mobility. In some cases it is possible to have reasonable enzyme actively both above and below the pI. These enzymes can be moved toward either a positively or negatively biased microlocation, depending on the chosen pH.

The Xba I cleavage of the M13mp18 vector at ML-1 is carried out as follows. The Xba I endonuclease is first free field electrophoresed to the ML-1/M13mp18 microlocation using an electronic delivery system. The electronic delivery system, containing 100 units of Xba 1 in pH 7.6 buffer, is biased negative and the ML-1/M13mp18 microlocation is biased positive at 0.1 mA for 2 minutes. The current is then reduced to 0.02 mA for 3 minutes. The electronic delivery system is turned off, while the ML-1/M13mp18 microlocation is biased negative and the ML-3/M13C-2 microlocation is biased positive at 0.1 mA for 5 minutes. The ML-3/M13C-2 microlocation is now biased negative and the electronic delivery system is turned on and biased positive at 0.1 mA for 2 minutes in order to remove Xba 1 and un-hybridized fragments from the ML-3/M13C-2 microlocation.

Observation by epifluorescent microscopy shows loss of red fluorescent signal at the ML-1/M13mp18 microlocation and presence of red fluorescent signal at the ML-3/M13C-2 microlocations, demonstrating Xba 1 cleavage of the M13mp18 vector. The same basic Xba cleavage procedure is now repeated for the ML-2/M13mp8 microlocation, which serves as a negative control. Since the M13mp8 vector has no Xba 1 site, cleavage and production of fragments is not possible. The ML-2/M13mp18 microlocation thus maintains its green fluorescent signal, and no fluorescent signal is observed at ML-4/M13C-2 microlocation.

A second example involves restriction cleavage reactions being carried out with the restriction enzymes are covalently attached to addressable microlocations on the device. In this case, restriction endonucleases would be derivatized and free field electrophoresed to addressable microlocations on an APEX device where they would become covalently bound. Methods for the derivatization and covalent attachment of restriction enzymes to solid supports are known to those skilled in the art. A variety of different restriction enzymes could be addressed to the APEX device. Specific cleavage reactions would be carried out by using free field electrophoresis to concentrate ds-DNA vectors or DNA samples at the microlocation containing the desired restriction endonuclease. The ds-DNA would be cleaved and fragments then moved to other microlocations on the device. When desired or useful other DNA modifying enzymes could be coupled to addressable microlocations on the APEX device. Also, this example should not be considered limited to DNA modifying enzymes, in that most other enzymes could be attached to addressable microlocations on APEX devices.

Example 10

Electronic Amplification Methods

In cases of hybridization analysis with very low target sequence copy number (e.g., HIV, septic blood infections, etc.), the multiplication or amplification of target DNA sequence would enable sensitivity to be improved by amplification of purified target DNA and/or RNA directly on an APEX device. Amplification would also reduce the requirement for very high yield preparative steps prior to hybridization analysis.

APEX amplification protocol provides complete electronic control of DNA movements, denaturation, and synthesis reactions. Most importantly DNA hybrids are denatured electronically without the use of high temperature or the need for thermophilic polymerases or other thermal stable enzymes.

Figure 17:
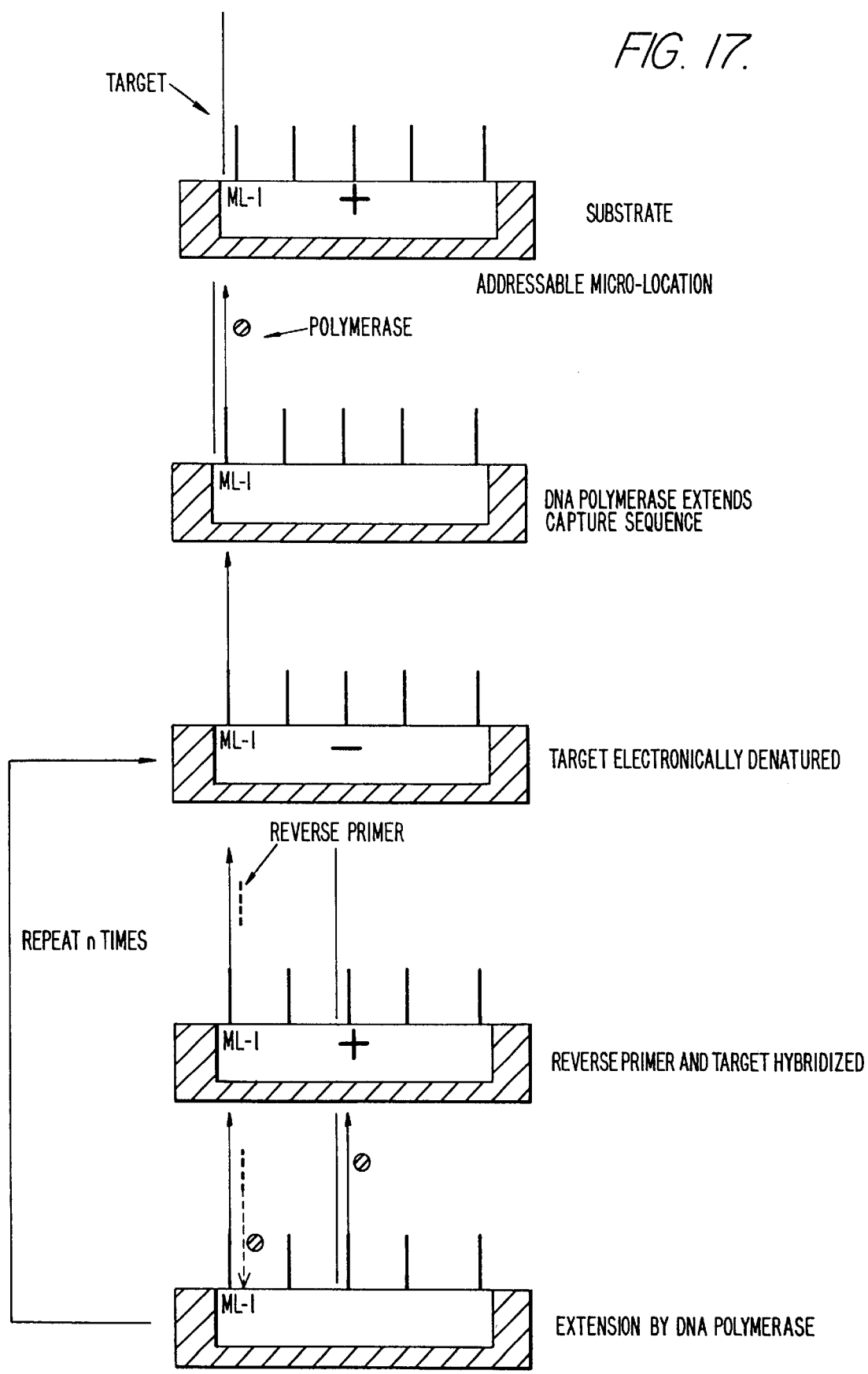
FIG. 17 shows a scheme for the electronically controlled amplification of DNA using polymerase.

As a first example, DNA synthesis can be achieved with high fidelity using DNA polymerase (Klenow large fragment) and without the need for thermal cycling. In this example, one DNA strand is amplified in a way that leaves it covalently bound to a microlocation. The procedure is carried out in the following manner: 1) the known target sequence is electronically hybridized to a capture probe of known sequence on an addressed microlocation, 2) synthesis of nascent complementary strand DNA (−) by DNA polymerase primed by the capture probe is carried out, 3) the newly synthesized DNA hybrids are electronically denatured, 4) annealing of target strand DNA to non-elongated capture probe and annealing of− strand complementary probe to nascent− strand DNA is carried out, 5) synthesis of nascent target strand DNA(+) by DNA polymerase and concomitant synthesis of− strand DNA as in 2 is carried out, thereby doubling the number of + and− strands each time these steps are repeated, and 6) size selection of amplified target is carried out by hybridization to a specially designed complimentary probe. The complete procedure, shown in FIG. 17, is described in more detail below:

Step 1) Attachment of Target Sequence to Capture Probe

Target sequence is electrophoretically transported to a microlocation (1) containing covalently bound capture probe. Target sequence can be present in a background of non-target (genomic) sequence but must be denatured prior to annealing to capture probe. Target sequence which is initially captured will be of variable length.

Step 2) Synthesis of DNA Complementary to Target

DNA polymerase and dNTP's are electrophoretically transported to microlocation 1. The capture probe provides a 3' end for DNA polymerase and the captured target sequence provides the template. Current sufficient to maintain a concentration of reagents amenable to synthesis are applied. The current may be constant or pulsed. These parameters can be manipulated to obtain differing ranges of lengths of nascent complementary (−) strand.

Step 3) Electronic Denaturation of Newly Synthesized Strands

Polarity at microlocation 1 is reversed and voltage is applied to separate the two strands. The amount of voltage and the time period of application will be dependent on the length and base composition of the hybrid DNA complex. These parameters may be determined empirically or calculated from electronic denaturation curves.

Step 4) Annealing of Primers (Capture and complementary Probes) to DNA Strands

Oligos need to be annealed to both + and − DNA strands to provide primer sites for DNA polymerase. For the target or + strand this is accomplished by electrophoretic transport of + strand to un-elongated capture probe. This will occur as long as un-elongated capture probe is in excess to elongated, covalently bound − strand DNA. Complementary probe is electrophoresed to the microlocation and binds to covalently bound− strand DNA. Now both + and − strands have primer bound to them and are templates DNA polymerase catalyzed synthesis (see figure). Binding of complementary probe may also occur with noncovalently bound− strand DNA, however these hybrids will not be electronically denatured and therefore should have little impact on the overall amplification.

Step 5) Synthesis of Two New Strands of DNA

Step 2 is repeated and since both + and − strands are primed templates, the amount of sequence specific DNA doubles. This geometric increase in the amount of DNA will occur each time these steps are repeated.

Step 6) Size Selection of Amplified Target Sequence

The nucleotide sequence of the complementary probe will determine the size and sequence of the amplified target DNA. Therefore, the amplified DNA can be custom designed to enhance efficiency in subsequent analysis and/or manipulation.

Other enzymes can be used in the amplification method of this invention, including, but not limited to, other DNA polymerases, T7 or SP6 RNA polymerses, reverse transcriptases, DNA ligases, and polynucelotide phosphoreaylases, and combinations of other nucleic acid modifying enzymes (endonucleases, exonucleases, etc.).

Example 11

Electronic Controller And Data System

All devices, whether APEX chip or micromachined devices, will be of the nature of an addressable array of microlocations (or macro-locations). A computer control/ data collection system has been designed to provide independent application of electric potentials to any pads in the array and to measure the resulting current flowing in the microlocation-electrolyte system. The computer control/ data collection interface provides:

a) Representation of the array of microlocations. Higher level and lower level representations provide views of all microlocations, with resolution of blocks of microlocations at the highest level view, and with fully resolved blocks of microlocations at the lower levels.

b) Clicking on a microlocation will pops-up a window view of the microlocation detailing the characterization of the microlocation, allowing setting of control of the microlocation with a time sequence of signals of various shape, electric potential magnitude and sign, etc., display of the control sequence overlaying that of other microlocations, etc. The system also provides display of the data and signals collected for the microlocation with statistics and comparisons with data from other microlocations. Menus provide analysis, documentation and archival functions for the control design, the actual control signals observed and the data collected.

c) The software provides all switching and data collection through a hardware interface controlled by inputs from the array control software described in b).

d) A separate hardware and software system provides image collection and processing capabilities. This systems images the array of microlocations and records fluorescence signals from DNA binding interactions at the active microlocations to provide readout of the DNA binding experimental results. Image processing software provides the ability to quantitatively process these images and extract quantitative assay results. This software is fully interfaced with the array controller/data collection software to provide an integrated system that records all the APEX device control/electrolyte current data and the assay results from imaging data, analyzes the data to provide reduced results for the assay along with ancillary information regarding the consistency and reliability of these results, and archive all the data and analyses.

e) An APEX controller will incorporate all of this software plus a top layer that provides only "DO ASSAY" and "RESULTS" displays, plus a button to access a) through c) functionality if necessary, but a) through c) will be collected and archived in all cases.

f) The initial version of the controller to be used for development projects uses a Macintosh Quadra 950 as a host computer and uses National Instruments boards interfaced with the Quadra 950 to provide the hardware interface described above. These boards apply the variable potentials to the APEX microlocations and measure the resulting current flowing in the electrolyte system. The National Instruments boards used in this controller are the High Resolution Multifunction I/O board, NB-MIO-16XL-18, the Analog Output board, NB-AO-6, the Timing Input/Output board, NB-TIO-10, the Block Mode DMA and GPIB Interface board, NB-DMA2800, and the Analog Signal Conditioning Modules boards and Modules for thermocouples, and other environmental sensors, 5B series. Connections between the NuBus boards in the Quadra and the APEX device will be through SCXI 16-Channel SPDT Relay Module boards housed in an SCXI-1001 Chassis.

Example 12

Electronically Controlled Sample Preparation and Hybridization Analysis—An Integrated APEX System Sample preparation usually involves selection of cells; disruption of cellular material (e.g., lysis), and a series of separation procedures and affinity reactions. Sample preparation is important for molecular biologic reactions. For example, hybridization assay is often limited because one loses significant amounts of the actual target DNA sequences due to inefficiencies in the sample preparation process.

The basic APEX concept for electronic control can be used for sample preparation in DNA hybridization assays. Electronic methods will allow sample preparation, cell selection and analysis to be carried out on an active electronic system of APEX components. The sample preparation would begin with cell selection and lysis, and the gross separation of DNA from cellular and extraneous materials in the sample. The electronic device would electronically process the sample DNA and move it efficiently toward the analytical component of the device, while removing the other materials. The system provides the proper scaling factor for efficient processing of the target DNA. For human genomic analysis, electronic sample preparation would include a highly efficient pre-hybridization step by which most of the complex non-specific DNA would be separated from the target DNA.

An integrated device or complete APEX system with sample preparation would take a relatively crude sample (blood, sputum, urine, etc.), and processes it with minimum mechanical manipulation and fluidics, and then electronically deliver target DNA to the analytical component of the device. This "active electronic processing" differs from automation or robotic processing, which are generally mechanical versions of the manual process and techniques.

Figure 18:
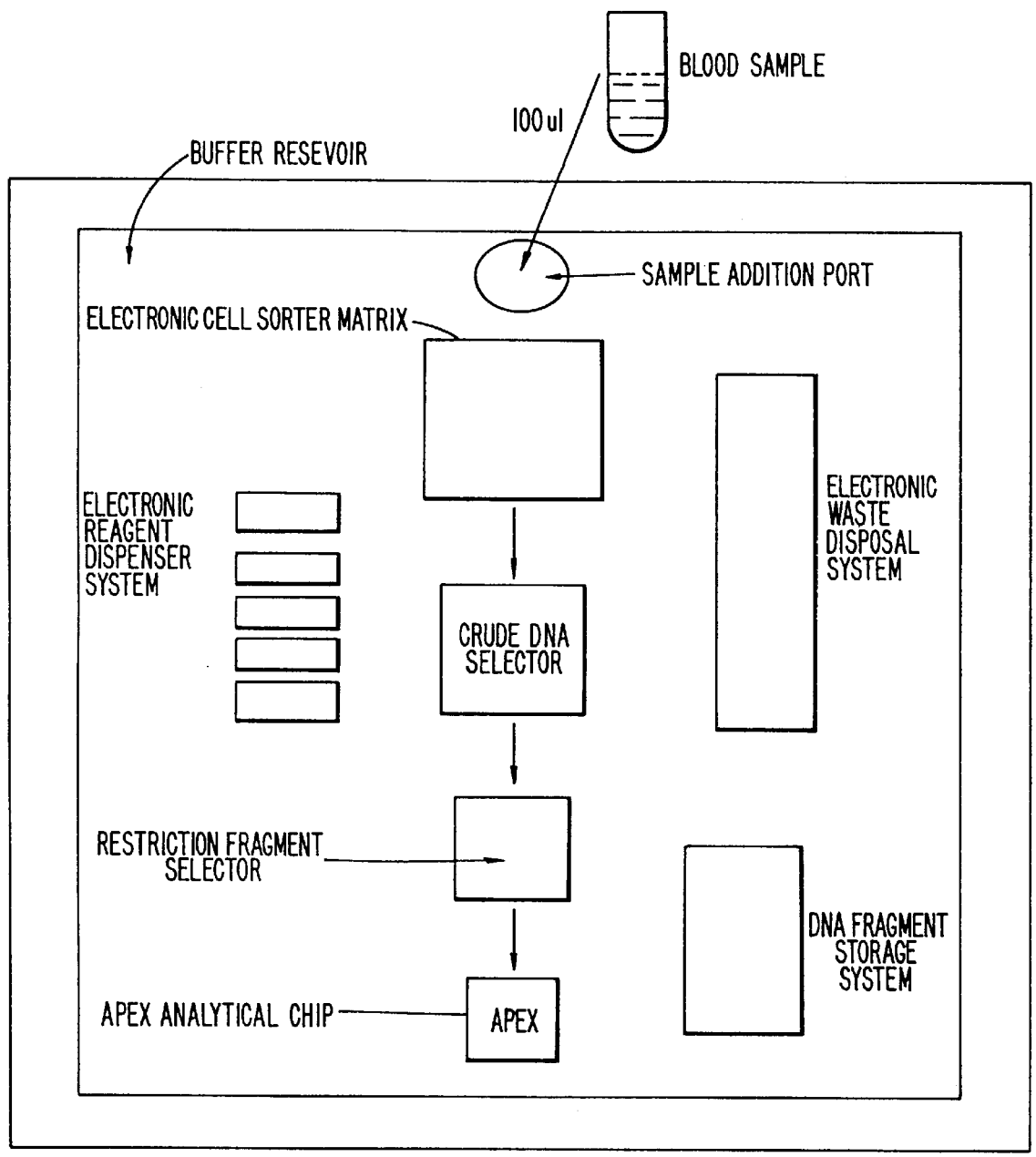
FIG. 18 shows a diagram of an APEX device which is designed to carry out sample preparation and DNA analysis.

An integrated APEX System for DNA sample preparation and analysis can be fabricated using a number of components all based on the general APEX concept. The components of the system include (1) an electronic cell selector unit; (2) an electronic reagent dispenser unit; (3) an electronic waste disposal unit; (4) a crude DNA selector unit; (5) a secondary DNA or restriction fragment selector unit; (6) a DNA fragment storage unit; and (7) the APEX analytical unit (chip). The integrated APEX system is shown in FIG. 18.

Such a system can be fabricated on a large silicon wafer. Alternatively, individual components can be fabricated by microlithography or micromachining techniques and arranged on (e.g., plugged into) a specially designed platform unit. The components of the complete system are designed so their active area scales to the relative sample size and the amount of materials in the sample (such as cells). For example, the cell selector active area generally would be larger than the crude DNA selector active area, which in turn would be larger than the restriction fragment selector active area, which would be larger than the APEX analytical chip active area.

By way of example, the cell selector "active area" could be of the order of several cm$^2$, while the total "active area" for a 64 microlocation APEX analytical component would be less than one mm$^2$. The platform unit is designed to hold all the component units in a sealed common buffer reservoir. Up to several hundred microliter of the appropriate sample is added to the system through a sample addition port near the cell selector component. The cell selector component is a larger scale APEX device which can have one or more selected affinities for different cell types. These affinity selections can be made on the basis of cell surface charge, haptens, and antigens.

By way of example, affinity selection for whole blood samples can be made to select white blood cells (lymphocytes, etc.) from red blood cells. Highly selective processes could be used to select fetal cells from material blood sample. It is also possible to provide affinity selection for infectious microorganisms (yeast, fungus, bacteria, and virus). While selected cells remain attached to the cell selector component; all other cells and proteinaceous materials are transported to the waste disposal unit. At this point the cells can be lysed by free field electrophoretic transport of charged detergents, and/or chaotropic agents, and/or appropriate lytic enzymes and proteinases (lysozyme, proteinase K, pepsin, etc.) from the electronic reagent dispenser unit to the cells on the cell selector unit. Appropriate biasing of the electronic waste disposal system can be used to remove certain lytic waste materials. The positive biasing of the crude DNA selector unit can now be used to transport the crude nucleic acid (DNA/RNA) materials to this component.

The crude DNA selector is an APEX device which has a general affinity for DNA. This affinity can be a positively charged surface, or a surface which contains a common or repetitive DNA sequence. For example, an Alu repeat capture sequence would effectively capture most of the crude DNA extracted from human cells. A common or generic bacteria or viral sequence could be used when infectious disease analysis is the objective. In addition to removing extraneous materials from the DNA; the APEX system is also designed to reduce the complexity of the sample DNA. This can be achieved by using restriction enzymes to selectively cleave the DNA at the crude DNA selector unit. The restriction enzymes are transported from the reagent dispenser unit. The cleaved restriction fragments can now be transported from to the secondary DNA or restriction fragment selector unit by biasing it positive. This unit is designed to selectively bind large fragments of DNA, using appropriate capture sequences on its surface.

At this point, selected DNA fragments can be transported to the APEX analytical chip for hybridization analysis. It is also possible to transport DNA fragments to the storage unit or even out of the system. The examples above represent just some of the possible scenarios for sample preparation and multiple hybridization analysis. The binding affinity programmability of components and flexibility of combining different components and functions allows a wide variety of procedures to be carried out.

Example 13

Electronic Hybridization With Histidine and Other Zwitterionic Buffers

The buffers and chemicals utilized in these experiments were purchased from Sigma (St. Louis, Mo.), Aldrich, (Milwaukee, Wis.), ICN Biochemicals (Aurora, Ohio), Boehringer-Mannheim (Indianapolis, Ind.) or Calbiochem (San Diego, Calif.). Oligonucleotides were synthesized '97) or were purchased from Oligo Therapeutics (Wilsonville, Oreg.). Peptide nucleic acid (PNA) oligonucleotide analogues were synthesized by PerSeptive Biosystems.

Microelectronic Chips, Permeation Layer and Instrumentation—These have been described previously with the following exception. The permeation layer employed herein has an underlayer of agarose beneath the top streptavidin-containing agarose layer (approximately one micron in total thickness). To make the underlayer, 50 ml glyoxal agarose (2%) was spun on at 2000 rpms for 20 sec prior to the application of the streptavidin-agarose layer. In brief, the 5580 series APEX chip used for these experiments consists of a 5×5 array of 80 mm circular microelectrodes with 200 mm microelectrodes at each corner of the array. Chips were mounted on a micromanipulator stage and the microelectrodes activated by a power supply and appropriately controlled relay switches. Fluorescently labeled oligonucleotides on the chip were visualized using oblique illumination with two 594 nm HeNe lasers and the images were quantified using either NIH Image or IPLab Spectrum software packages.

Accumulation and Hybridization—Two biotinylated capture oligonucleotides, ATA5 and ATA4 were electronically transported and localized at adjacent microelectrodes. The solution was removed and the chip washed 3–4× in test buffer. Buffers employed in these studies are listed in Table 3 and were utilized at the listed pH values and concentrations presented.

TABLE 3

| buffer | concentration | pKa[1] | pI | pH[2] | conductivity ($\mu$S/cm) |
|---|---|---|---|---|---|
| glycine | 50 mM | 2.34, 9.60 | 5.97 | 6.01 | 2.5 +/− 0.2 |
| glycine | 250 mM | 2.34, 9.60 | 5.97 | 6.11 | 7.8 +/− 0.5 |
| β-alanine | 50 mM | 3.60, 10.19 | 6.90 | 6.71 | 3.6 +/− 0.6 |
| GABA | 50 mM | 4.03, 10.56 | 7.30 | 6.76 | 5.6 +/− 0.6 |
| cysteine | 50 mM | 1.71, 8.33, 10.78 | 5.02 | 5.08 | 9.0 +/− 0.9 |
| cysteine | 250 mM | 1.71, 8.33, 10.78 | 5.02 | nd[4] | 21.8 +/− 4.4 |
| 3(τ)-methyl-histidine | 50 mM | 1.70, 5.87, 9.16[3] | 7.52 | 7.44 | 39.4 +/− 0.4 |
| D-histidine | 50 mM | 1.78, 5.97, 8.97 | 7.47 | 7.70 | 57.1 +/− 0.3 |
| L-histidine | 50 mM | 1.78, 5.97, 8.97 | 7.47 | 7.65 | 60.1 +/− 0.1 |
| carnosine | 50 mM | 2.64, 6.83, 9.51 | 8.17 | 8.07 | 74.5 +/− 5.5 |
| 1(π)-methyl-histidine | 50 mM | 1.64, 6.46, 8.61[3] | 7.54 | 7.59 | 117 +/− 2.8 |
| pyridine | 50 mM | 5.19 | — | 8.17 | 5.0 +/− 0.8 |
| imidazole | 50 mM | 6.99 | — | 9.08 | 17.6 +/− 1.6 |
| collidine | 50 mM | 6.69 | — | 9.85 | 33.0 +/− 0.9 |

[1]Values obtained from Budavari, S. (1980) The Merck Index, 11th Ed., Merck & Co., Inc. Rahway, NJ, unless otherwise noted
[2]pH of buffer solution measured in water at room temperature
[3]Remelli, M., Munerato, C. and Pulidori, F. (1994) J. Chem. Soc. Dalton Trans. 2049–2056
[4]nd = not determined The L-isomers of amino acids were used, unless otherwise noted. The chip was equilibrated in test buffer for 5–10 min. Then fresh buffer containing 10 nM BODIPY-Texas Red labeled RCA5 (btrRCA5), an oligonucleotide complementary to ATA5 but not ATA4 (RS paper) was applied.

ATA5 5'-GATGAGCAGTTCTACGTGG-3'-Biotin
ATA4 5'-GTCTCCTTCCTCTCCAG-3'-Biotin
btrRCA5 btr-5'-CTACTCGTCAAGATGCACC-3'

The 200 mm microelectrodes were employed as cathodes and one microelectrode within the array used as the corresponding anode. Accumulation was assessed by sourcing a 500 nA constant current to individual microelectrodes for 30 sec and monitoring the accumulation of fluorescence at the positively-biased (anode) site in the microelectrode array. Signal arising from non-fluorescent sources (ie. thermal noise, etc.) was subtracted. Experiments examining the effect of different currents upon signal accumulation were conducted in a similar fashion except that the applied current varied from 100 nA to 1 mA. Initial rates were calculated for the first 5 sec of signal accumulation, during which, linear fluorescence accumulation was observed in all buffers. For the comparison between conductivities of various buffers, the data is presented as fold increase over initial fluorescence to account for chip-to-chip variation as well as laser illumination variations in signal levels. For other experiments, the data is presented as attomol product versus time, after converting[2] the observed fluorescence intensity to moles of labeled oligonucleotide.

Following accumulation at one microelectrode location, the buffer was removed and fresh buffer containing btrRCA5 applied. An adjacent microelectrode was then sourced in a similar fashion. Upon completion, the buffer was removed and the chip washed 5–7 × with test buffer without btrRCA5. The pair of previously targeted microelectrodes were then illuminated and the fluorescence present at each site quantified. Control experiments utilized a bodipy-Texas Red labeled oligonucleotide complementary to ATA4 to verify the integrity and concentration of the ATA4 capture oligonucleotide. Percent hybridization efficiency was calculated as follows: (complementary oligonucleotide signal—noncomplementary signal)/(signal present immediately prior to the end of the applied current)×100.

Buffer Conductivity and pH Measurements—The conductivities of test buffer solutions utilized for transport and hybridization were measured at RT using an Accumet 1.0 $cm^{-1}$ glass conductivity cell connected to an Accumet Model 50 pH/Ion/Conductivity meter (Fisher Scientific). Buffer pH values were obtained using an Accu-pHast variable temperature combination electrode and the same model meter.

Micro-pH Measurements—Antimony electrodes were fabricated using methods described elsewhere (Horrocks '93) with the following minor modifications. Theta glass (World Precision Instruments, Sarasota, Fla.) was used to obtain a double barrel type electrode, plus all capillaries were hand pulled with a final tip diameter estimated to be 75 $\mu$m. The potential of the antimony electrode was measured relative to a Ag/AgCl reference electrode using the pH meter employed above. Calibration of the antimony electrode yielded a slope of 57 mV/pH, a value in good agreement with other literature values (Horrocks '93, Bicher '72, Matsumara '80, Glab '89). While viewed through a microscope, the antimony electrode was brought down to the surface of an agarose coated chip using a motorized X-Y-Z micromanipulator until the electrode was observed to bend. Afterwards the electrode was raised to a height just above the observed inflection point. The distance from the antimony electrode to the chip surface was estimated to be 7 $\mu$m. The antimony electrode tip was then positioned over individual microelectrode wells at an oblique angle so as to minimize diffusion effects (Horrocks '93). The pH readings were obtained using either 200 nA or 500 nA constant current in either 50 mM KCl, 50 mM histidine, 50 mM imidazole or 50 mM GABA.

Passive Hybridization versus Electric Field Hybridization—ATA5 was electrically targeted to the first four columns of the microarray on streptavidin/agarose coated chips prepared as above, and ATA4 was targeted to the remaining column. For passive hybridization, either 5.0 nM or 0.5 nM btrRCA5 in 5×SSC (1×=0.15 M NaCl, 15 mM sodium citrate, pH 7.0) was applied for 1 min, then the chips were washed 6× in buffer and imaged. For the 3 min timepoint, fresh buffer containing btrRCA5 was applied and incubated for an additional 2 min to achieve 3 min cumulative incubation time. This approach was repeated for the remaining time points. A similar experiment was performed using 5 nM btrRCA5 in 50 mM histidine. For electric field hybridization, either 5.0 nM or 0.5 nM btrRCA5 in 50 mM histidine was applied. Five sites, 4 with ATA5 previously attached and 1 with ATA4, were electronically targeted using 3.1 V total, (approximately 500 nA/site). Following application of the current for the desired time period, the chip was washed 6× in histidine and imaged. Other data points were obtained in a similar fashion by targeting fresh solutions of btrRCA5 in histidine to previously untargeted sites for the indicated times. In both passive and electric field mediated hybridization, the background signal present at the ATA4 sites was subtracted from the signal present at ATA5 sites.

Comparison of Hybridization of Phosphodiester-Linked Oligonucleotides to PNA Analogues—Thirty $\mu$M biotinylated oligonucleotides or PNA versions of these were microdeposited upon individual sites of a streptavidin/agarose coated microarray in 10% glycerol, 25 mM NaCl, 25 mM NaPhosphate pH 7.4 using an Eppendorf Micromanipulator 5171 and Transjector 5246. Following a 30 minute incubation, the chip was rinsed with water. Oligonucleotide sequences and PNA analogue sequences are as follows:

DNA 1: biotin-CACCTGCTTTGATAGCTG

PNA1: biotin-O-O-CACCTGCTTTGATAGCTG, O=linker

DNA2: biotin-GATGAGCAGTTCTACGTGG

PNA2: biotin-O-O-TGTACGTCACAACTA

Reporter DNA: btr-CAGCTATCAAAGCAGGTG, btr=BODIPY-Texas Red DNA1 and PNA1 are complementary to reporter DNA whereas DNA2 and PNA2 serve as controls to evaluate non-specific hybridization. Electronic hybridization was performed with 5 $\mu$L of DNA reporter probe in 50 mM GABA or 50 mM histidine. The chip was electronically activated for 10 seconds or 30 seconds at 200 nA or 30 seconds at 500 nA. Following each electronic hybridization, the chip was rinsed several times with the same buffer. After the final electronic hybridization, the chip was washed in a mixture of 0.2× STE (20 mM NaCl, 2 mM Tris-Cl pH 8.0, 0.2 mM EDTA pH 8.0) and 0.1% sodium dodecyl sulfate and a final image taken. Hybridization efficiency was calculated as above.

Passive Hybridization at Different pHs—Biotinylated ATA5 and ATA4 were electronically targeted to adjacent sites upon streptavidin/agarose coated microarrays. Buffer consisting of 100 nM btrRCA5 in 50 mM histidine at its pI value (pH>7.5) or adjusted to either pH 6.0, 5.0, 4.0 or 3.0 with HCl was added to each chip and allowed to react for 10 min. A parallel hybridization was done in 6×SSC. After this hybridization period, the chips were washed in 0.2×STE, 0.1% sodium dodecyl sulfate, as above and the remaining fluorescence at each site quantitated. Fluorescence values present at ATA4 sites were subtracted from adjacent ATA5 sites and the remaining fluorescence converted to attomol btrRCA5 specifically hybridized. Additional experiments repeated this methodology and also examined buffer adjusted with concentrated acetic acid (at the pI and at pH 6 and 5). Similar results were observed.

Results

Effect of buffer composition on oligonucleotide transport.

Figure 20:
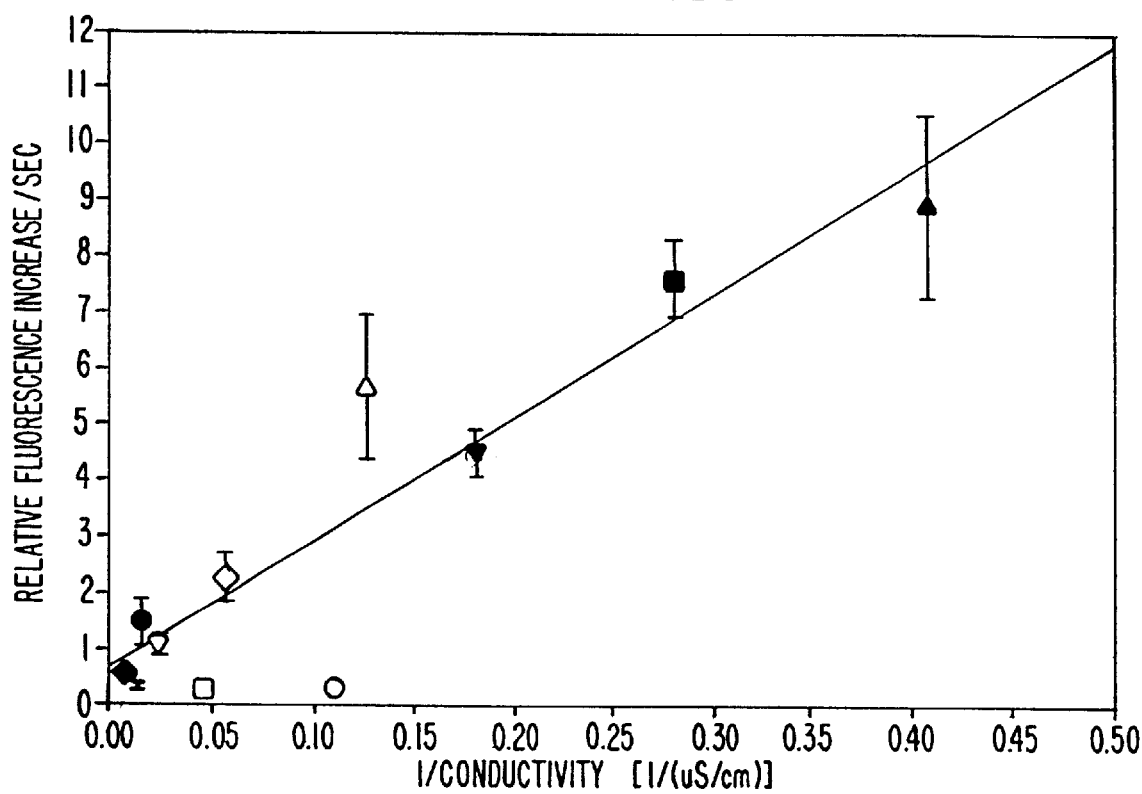
FIG. 20 is a graph of relative fluorescence increase per second versus 1/conductivity.

To promote hybridization of complementary nucleic acid in a dilute solution, the sample must be concentrated over the capture sequence. This causes a local increase in the Cot value in the region surrounding the capture, increasing the rate of hybridization by mass action. Under constant current conditions, charge will be transported by all ionic species in the solution and thus the conductance of the solution will determine the proportion of the current carried by the oligonucleotide. Therefore low conductance solutions would be expected to lead to more rapid transport and accumulation of oligonucleotide over the anode. To measure this, fluorescently labeled reporter oligonucleotides were electronically targeted to locations where either complementary or noncomplementary oligonucleotides had previously been attached. The accumulation of fluorescent signal over time in response to the applied current was then assessed for several different buffers (Table 3). We noted that accumulation eventually reaches a plateau. Therefore, to accurately measure the effects of conductivity, we have measured the initial rate of accumulation. FIG. 20 displays analysis of a representative selection of buffers. The initial increase in fluorescent signal is compared to the inverse of buffer conductivity (i.e. solution resistance). This plot shows a roughly linear relationship between the solution resistance and the accumulation of signal. The more conductive the solution, the slower the rate of oligonucleotide accumulation.

Interestingly, the rate of accumulation in cysteine (the two groups of data lying just above the abscissa away from the intercept in FIG. 20) was lower than would be expected based upon initial conductivity. One possible explanation for this is that cysteine's sulfhydryl group is electrochemically reactive at voltages lower than that required for the hydrolysis of water (Davis '66) and generates additional reactive ions or molecules. Therefore, factors other than the initial conductivity of the solution may govern electrophoretic properties of buffers such as cysteine.

As mentioned above, we also noted a progressive slowing of fluorescence accumulation, the rate of which differed between buffer solutions. At a constant current, a gradient of ionic strength builds from the electrode into the bulk solution over time (Oldham '88, Newman '91). This results in an increase in the conductivity of the solution immediately above the electrode. This increase in conductivity results in lower mobility or a decreasing rate of DNA accumulation. In addition, as DNA accumulates above the electrode, diffusion increasingly opposes the electric field mediated transport of DNA, also slowing the overall rate of accumulation. Eventually, a steady state might be reached where the diffusion rate equals the electric field transport resulting in no further net accumulation of the oligonucleotides (Newman '91). In addition, the mobility of the oligonucleotides decreases as they encounter regions where the electrochemically mediated decrease in pH (see below) matches the pI of the oligonucleotide. Finally, signal could be lost by the electrochemical quenching of the fluorescent signal later in the reaction.

Figure 21A:
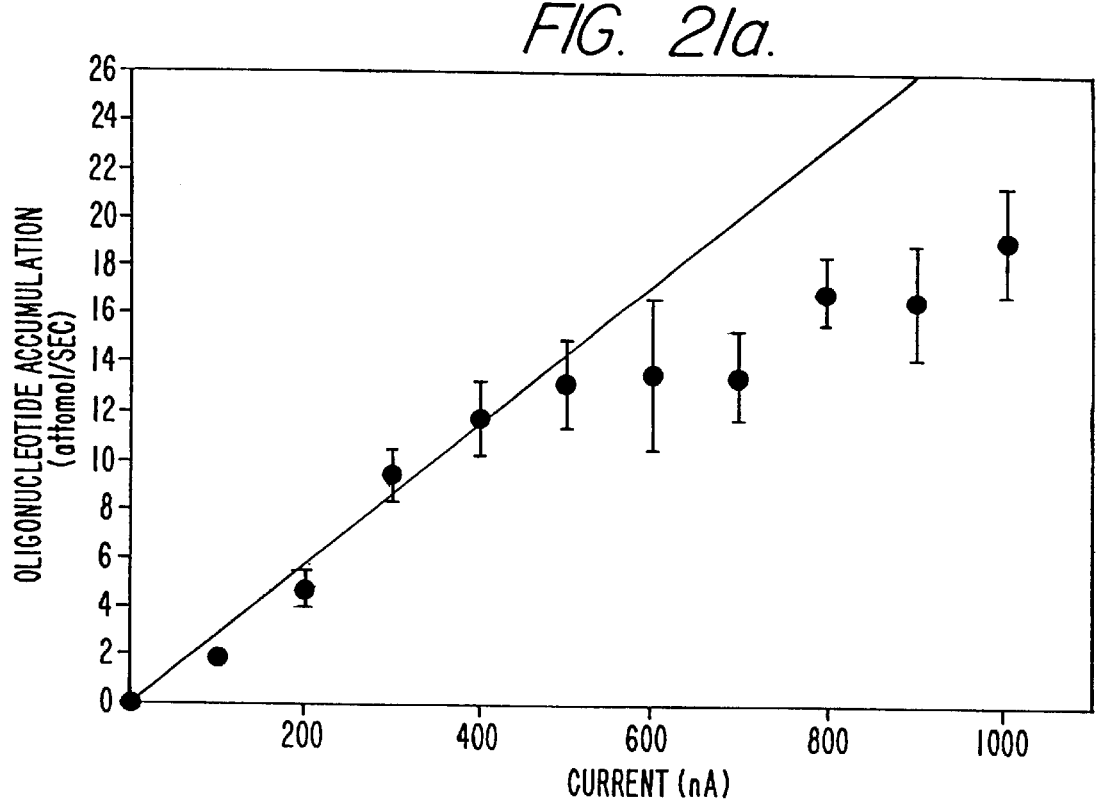
FIGS. 21a and 21b are graphics showing oligonucleotide accumulation versus current.
Figure 21B:
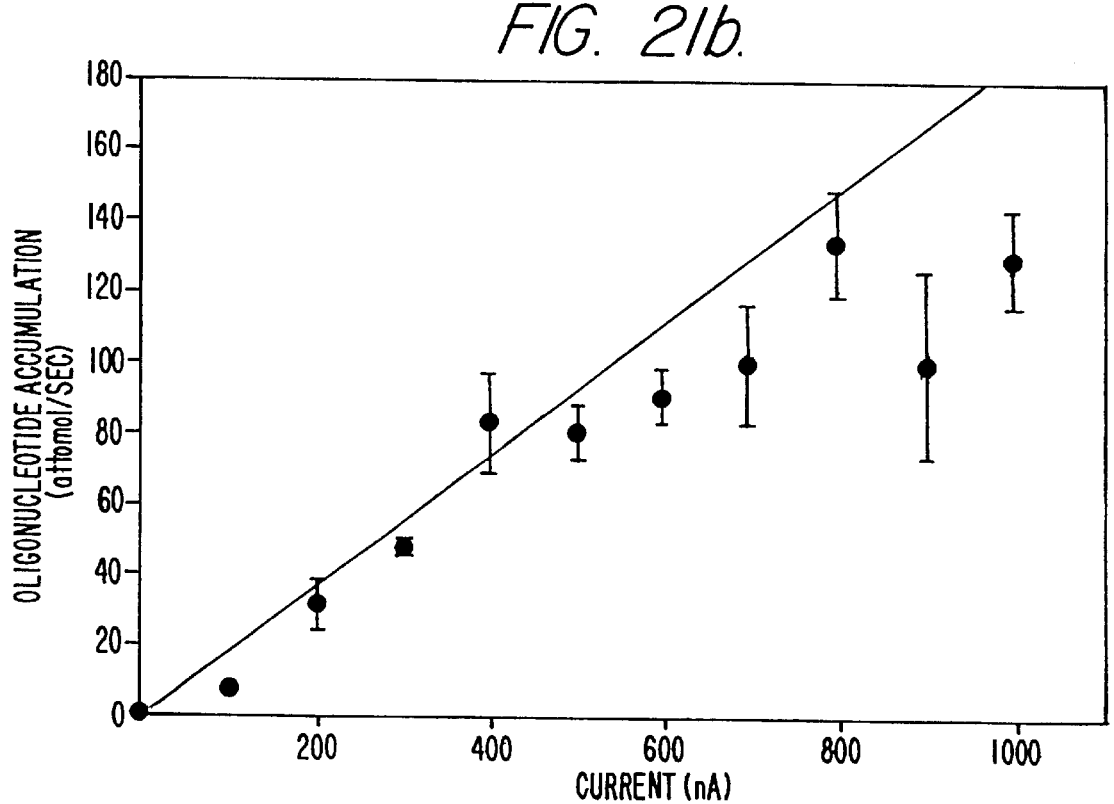

If the nucleic acid alone were carrying the current, migration of the charged oligonucleotides would be predicted to be proportional to the applied current. However, analysis in FIG. 21 demonstrates nonlinear behavior with increasing current. The rate of signal accumulation appears to reach a plateau as applied current is increased. This effect is more dramatic for histidine, a buffer with higher conductivity than GABA. The nonlinear accumulation rates are again consistent with a more rapid build-up of ionic constituents or breakdown products of the buffer at higher currents.

Effect of electronic field application on hybridization.

Figure 22:
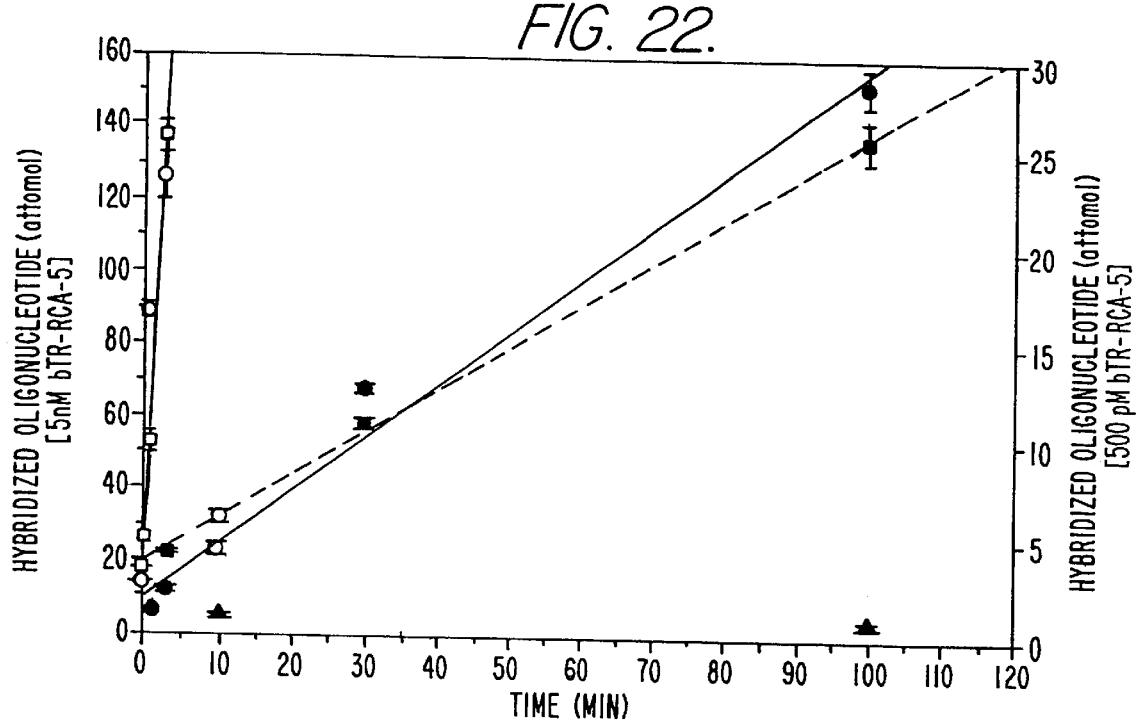
FIG. 22 is a graph showing hybridized oligonucleotide versus time.

The effect of electronic concentration of oligonucleotides on the rate of hybridization is shown in FIG. 22. In this experiment, an oligonucleotide was first electronically directed to and then anchored at selected sites of the microarray. The corresponding fluorescent labeled complementary oligonucleotide, was introduced in either a high salt buffer (5×SSC), and allowed to passively hybridize, or was introduced in 50 mM histidine and electronically targeted to the capture oligonucleotide. As shown, the rate at which the electronically targeted oligonucleotide hybridized was 30 fold to 40 fold greater than the rate of passive hybridization. No hybridization was observed using histidine in the absence of an applied electric field, irrespective of the time allowed. Thus, concentration alone may not fully explain the marked increase in efficiency of oligonucleotide hybridization in the electric field.

Figure 23:
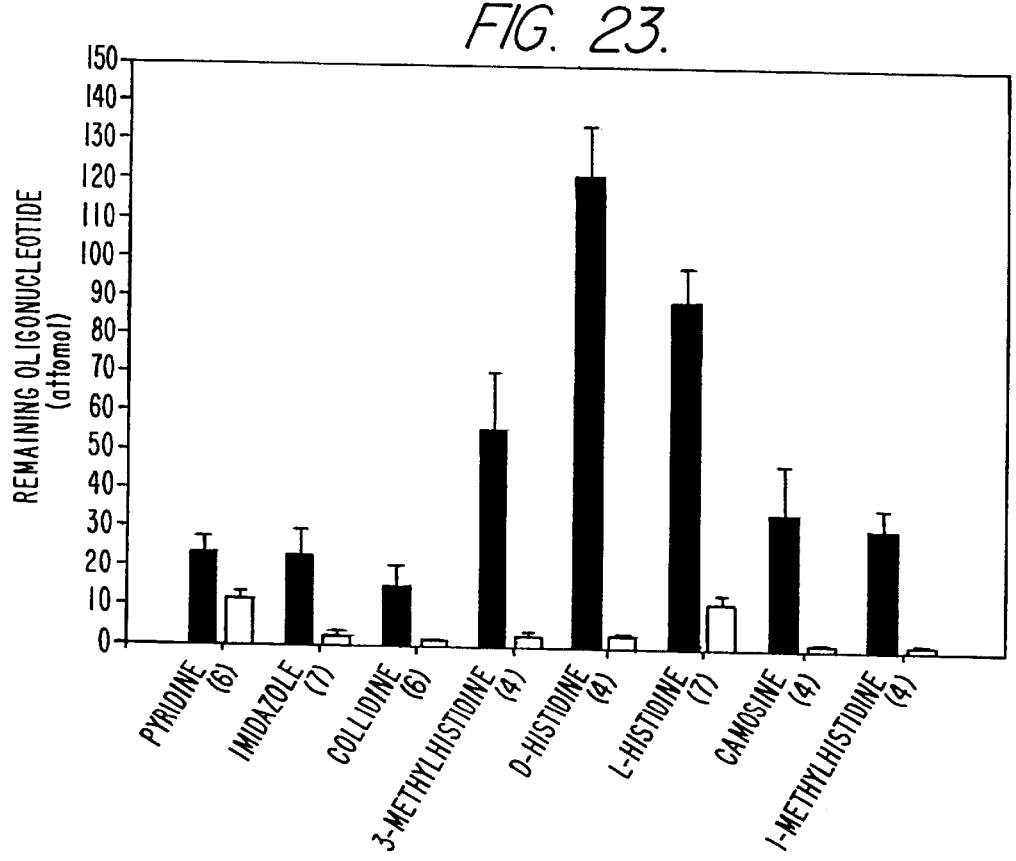
FIG. 23 shows a bar graph of remaining oligonucleotides as a function of buffer.

Despite rapid transport and high level accumulation of signal over the pads, neither GABA, b-alanine, nor glycine was capable of supporting sequence specific hybridization. Cysteine was difficult to evaluate because of poor signal accumulation. In contrast, histidine demonstrated specific hybridization when a non-complementary capture sequence was used as control. The ratio of complementary capture signal levels to non-complementary capture signal levels served as an indicator of specificity. FIG. 23 shows a comparison of those buffers found to be effective in promoting electronic hybridization (complementary>non-complementary, $P<0.05$). These include histidine, substituted histidines, and heterocyclic species such as imidazole, pyridine and collidine (a trimethylated pyridine) (FIG. 5). A consistent feature of the buffers listed in Table 4 is the presence of a weak base, e.g. imidazole ring, whose pKa value near neutrality.

TABLE 4

| buffer | transported[1,2] | specific hybridization[1] (attomol) | hybridization efficiency[3] |
|---|---|---|---|
| pyridine | 764 +/− 66 | 12.8 +/− 4.2 | 1.7 |
| imidazole | 528 +/− 63 | 21.2 +/− 6.6 | 4.0 |
| collidine | 382 +/− 63 | 14.1 +/− 4.6 | 3.7 |
| 3-methylhistidine | 259 +/− 48 | 54.0 +/− 14.8 | 20.8 |
| D-histidine | 490 +/− 50 | 119 +/− 11.8 | 24.3 |
| L-histidine | 533 +/− 65 | 78.0 +/− 9.1 | 14.6 |
| carnosine | 129 +/− 45 | 33.7 +/− 12.1 | 26.1 |
| 1-methylhistidine | 141 +/− 20 | 30.0 +/− 5.0 | 21.3 |

[1]data are presented as value +/− SEM
[2]fluorescent signal present at completion of electronic targeting.
[3]efficiency = [(specific hybridization)/(transported)] × 100

In contrast, the buffers which did not support hybridization contain no such buffering group. The failure of zwitterionic buffers such as GABA to support electronic hybridization, despite high accumulation, again suggests that factors other than oligonucleotide concentration are important. These results suggest that buffering capability at neutral pH may be an important property for supporting hybridization under these conditions.

Further analysis of Table 4 reveals marked differences in the relative efficiencies of hybridization. That is, two distinct groupings in the data appear.

One grouping consists of imidazole, pyridine and collidine. These compounds yielded an approximately fivefold lower hybridization efficiency when compared to the other buffers, D- and L-histidine, carnosine and the methylated histidine derivatives. (These experiments were designed to reveal differences in hybridization efficiencies and therefore were performed under conditions that would not saturate available capture sites). The more efficient buffers all contain an imidazole or substituted imidazole ring, yet are more efficient than imidazole alone in supporting hybridization. This suggests that other functional groups present on these molecules also aid in the hybridization process.

A final aspect of the data listed in Table 4 is the relatively poor hybridization efficiency of L-histidine as compared to the other histidine-like compounds. Since specific hybridization is based upon subtracting the non-specific signal from the specific signal, then either of these parameters may influence the final hybridization efficiency. Evaluating the levels of non-specific signal as compared to the amount of material transported, indicated that L-histidine had a higher level of nonspecific signal, 2.2%, as compared to the other histidine-like buffers, which were 1% or less. The reason for this higher retention in L-histidine is unclear, however other experiments indicate that this background signal can be removed with more extensive washing. It may be that the slightly higher transport in 1-histidine as compared to the other histidine derivatives results in some threshold concentration such that more fluorescent oligonucleotide concentrates further within the permeation layer and is therefore more difficult to remove. Results from pyridine somewhat support this possibility. When compared to imidazole and collidine, pyridine has the highest transport and non-specific signal but, within its group, it also has the lowest efficiency of hybridization. However, differing non-specific interactions between L-histidine, oligonucleotide and, possibly, t, the permeation layer cannot be ruled out.

Effect of pH on hybridization

Figure 24A:
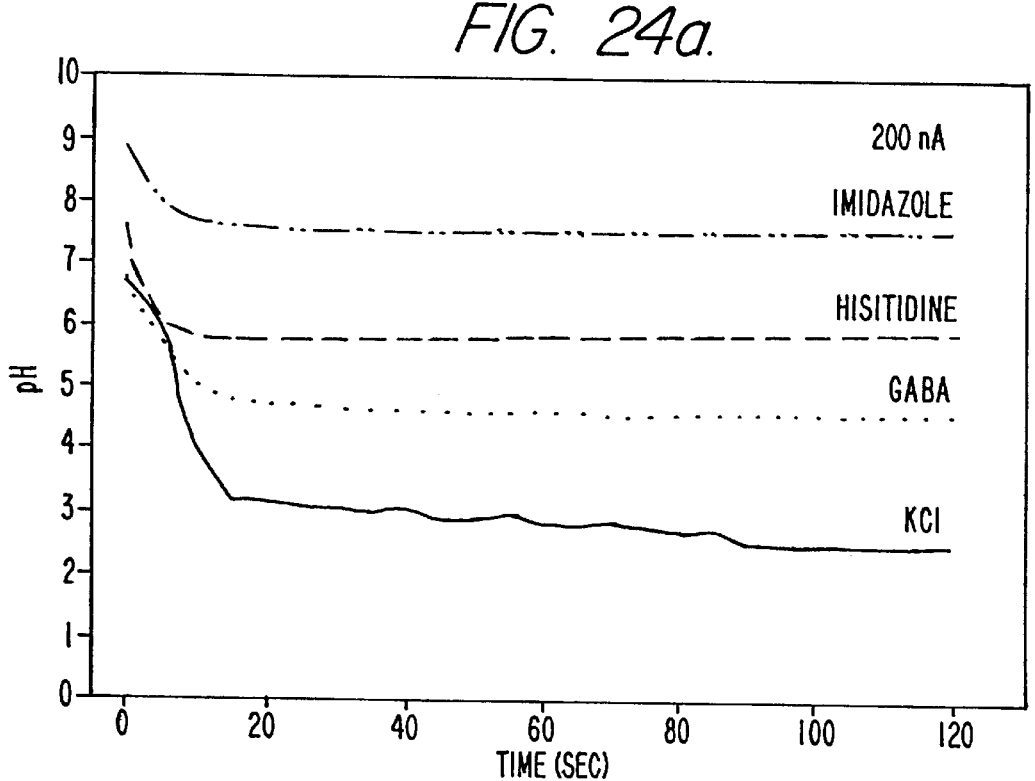
FIGS. 24a and 24b are graphs of pH as a function of time for various currents and buffers.

As noted above, those buffers that successfully supported hybridization have titratable substituents with pKa values which are at or near neutral pH. This could be particularly important since acid is generated by electrolysis over the anode (capture site) during transport. To evaluate the effect of pH on hybridization, a micro pH electrode, approximately 75 mm in outside diameter, was constructed and positioned at a constant distance just above the surface of the permeation layer over individual electrode sites. Since the hydrolysis of water generates protons at the electrode (or within the electrochemical double layer), there is a proton gradient extending from the electrode surface through the permeation layer and out into the solution. Therefore, pH measurements shown in FIGS. 24a and b may be somewhat higher than those experienced by the oligonucleotides which are anchored in the topmost portion of the permeation layer. In the absence of buffer, a dramatic decrease in the pH was observed even at low current levels, 200 nA, (FIGS. 24a and b). At 500 nA, the unbuffered system demonstrated an extremely rapid drop in pH and the generation of gas bubbles (FIG. 6B). In contrast, GABA was somewhat more effective in buffering the pH at low currents. Histidine and imidazole proved to be much more effective buffers maintaining the pH above the surface of the permeation layer above pH 5 for currents of either 200 nA or 500 nA.

These findings suggest that the imidazole ring may serve as the primary source of buffering for histidine and imidazole within this pH range. In contrast, GABA does not possess such a group and must therefore rely upon the carboxylate group for buffering at low pHs. These low pHs may not support hybridization of oligonucleotides well (Bloomfield '74). Alternatively, inability to become protonated near neutral pH may prevent these buffers from providing cations that shield repulsion between the negatively charged phosphate backbones.

Figure 24B:
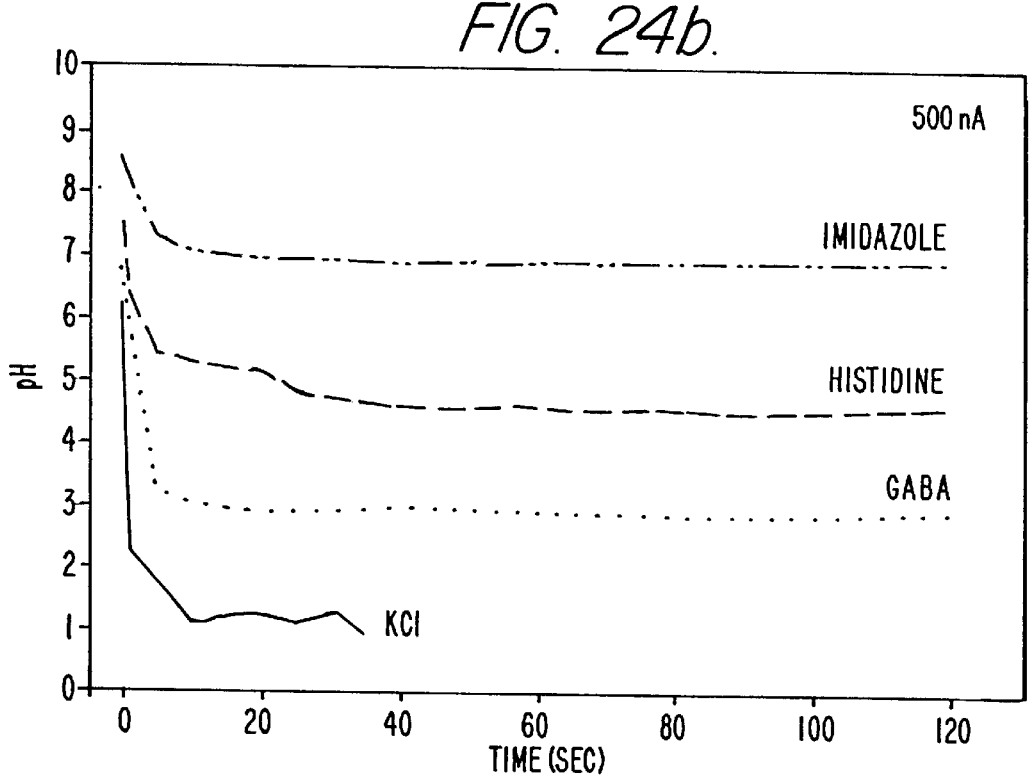
Figure 25:
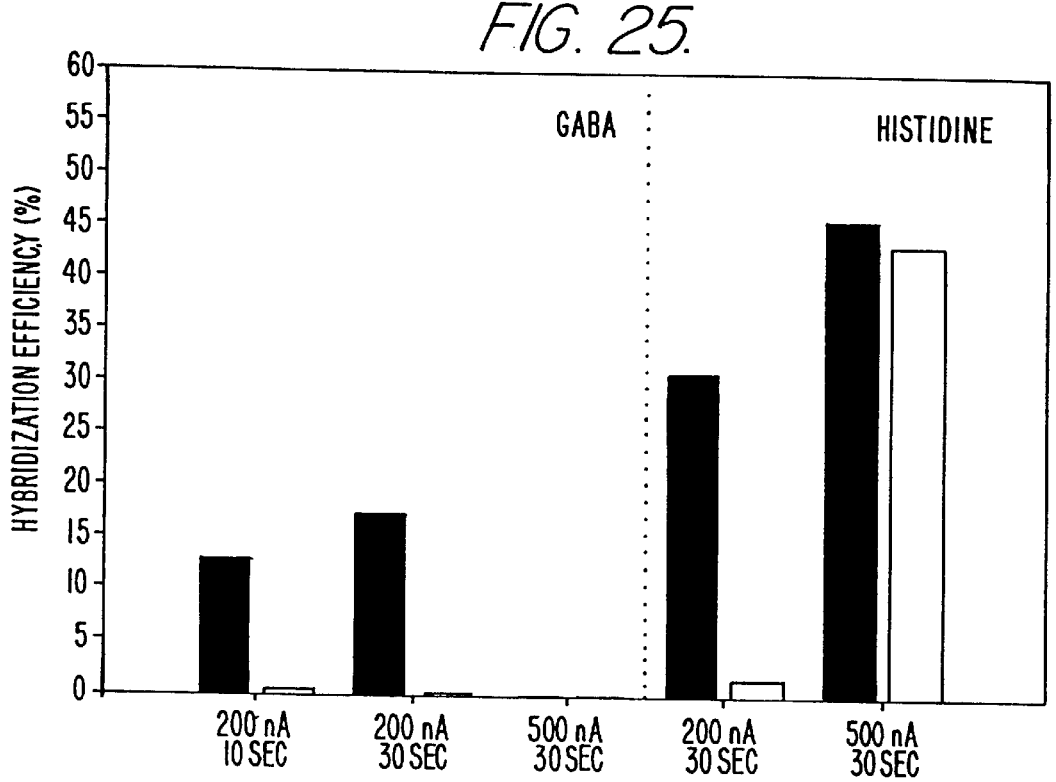
FIG. 25 is a bar graph of hybridization efficiency (%) as a function of various currents and times in GABA and histidine.

In order to clarify whether GABA's inability to support hybridization is the result of either the acidic environment or by a failure to provide adequate cationic shielding, a neutral backbone (PNA) was substituted for the negatively charged phosphodiester backbone of the capture oligonucleotide and the effect of this substitution examined. Hybridization of PNA hybrids has been demonstrated to occur with similar affinities but to be largely salt independent (Egholm '93). A representative set of results from four sets of experiments examining the effect of PNA substitution is shown in FIG. 25. This figure shows a comparison of the hybridization efficiency in histidine as compared to GABA using either PNA or DNA capture oligonucleotides and a common, fluorescently labeled DNA oligonucleotide. Hybridization in GABA was seen between the uncharged PNA backboned oligonucleotide and the DNA reporter oligonucleotide at 200 nA, whereas no hybridization was observed in the corresponding DNA:DNA pairing. Since similar degrees of local nucleotide concentration were achieved, this suggests that shielding of the phosphodiester backbone is an important component of the hybridization process under these conditions. This observation is further supported by the comparable pH values obtained in GABA at 200 nA and histidine at 500 nA (FIG. 24). No hybridization was observed in GABA at 200 nA despite a range of pH compatible with DNA:DNA hybridization. Therefore some component other than pH appears to be required for hybridization.

However, if the pH is reduced below a critical level, the acidity will be too great to support hybridization between the nucleotide bases. This may account for the lack of hybridization with either PNA:DNA or DNA:DNA duplexes at 500 nA in GABA.

In contrast, DNA:DNA hybridization in histidine only occurs well at 500 nA, while PNA:DNA hybridization occurs at roughly equal efficiencies at either current. These currents correspond to higher pH values in histidine than in GABA. At 200 nA, the pH of the solution is >6 whereas, at 500 nA, the pH is >5. Therefore, at 200 nA, fewer histidine molecules have protonated imidazole rings when compared to 500 nA. A higher concentration of protonated species may be suitable for shielding phosphodiester backbones and permitting hybridization of DNA.

Figure 26:
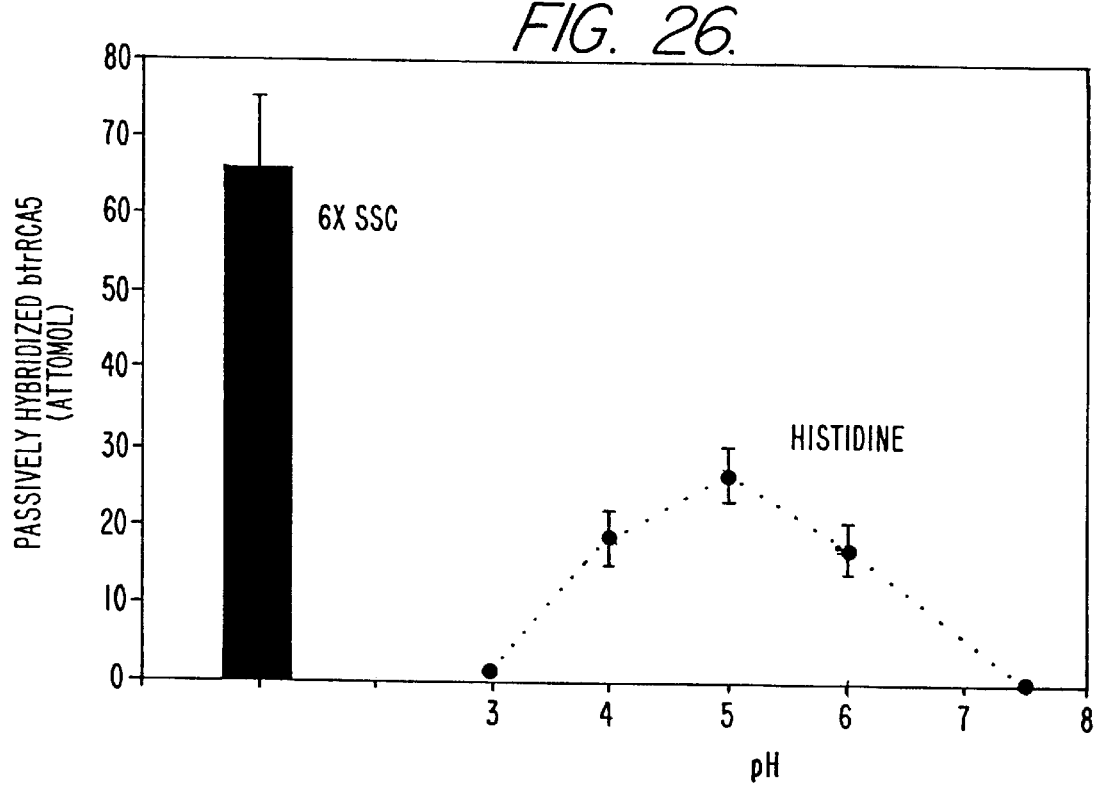
FIG. 26 is a graph of passively hybridized btrRCA5 in 6×SSC and histidine at various pHs.

To test whether protonation of histidine aids hybridization, passive (non-electronic) hybridization was performed in histidine. As shown in FIG. 26, histidine at its pI (pH 7.5) does not facilitate hybridization. At this pH, few molecules of histidine will possess a net positive charge for any significant time. In contrast, histidine at pH 6.0 and 5.0 accelerated hybridization. Thus, there appears to be a correlation between histidine's ability to support hybridization and its degree of protonation. That shielding could be more effective is demonstrated by the greater effectiveness SSC which contains nearly 1 M salt as a compared to the 50 mM histidine. However, as the solution became more acidic, hybridization in histidine decreased. This was probably due to effects upon the oligonucleotides themselves and not attributable to increased protonation of histidine, which would increase the net positive charge on histidine and aid hybridization. Taken together with the previous results, it therefore appears that a combination of factors including concentration, maintenance of the pH near neutrality and the generation of a cationic species suitable for shielding the nucleotide phosphodiester backbones all contribute to electronically mediated hybridization of DNA:DNA complexes under these conditions.

Discussion

The application of electric fields to microscale oligonucleotide arrays allows great acceleration and exquisite control over hybridization reactions. These advantages are augmented by the use of low conductivity or certain zwitterionic buffers. In general, these low-ionic strength buffers allow efficient transport of oligonucleotides to discrete sites in the presence of an applied current. As these buffers are not favorable for hybridization under passive conditions, this provides for the control of hybridization to only programmed anode sites. In addition to the mass action effect of concentration, our results suggest that the electrochemically-mediated production of positively charged buffer ions also facilitates the hybridization process. We have noted that a select subgroup of low conductivity buffers support hybridization under these conditions. Thus, we can separate transport from hybridization through the buffers and currents employed.

This programmed pH gradient allows discrete activation of hybridization zones and is a novel application for microelectronic devices. In our case, the buffering serves two roles: 1) it maintains the pH as close to neutrality as possible; and 2) it actively participates in the reaction. In fact, if the pH is lowered below a critical threshold value, hybridization will be hindered. In short, in alleviating the detrimental pH effects created by hydrolysis at the anode, we generate a species beneficial to the hybridization reaction.

Interestingly, the efficiency by which these buffers support the hybridization process appears dependent upon the nature of the functional groups present. That is, once the criteria for possessing a buffering capacity within the hybridization window and the resultant generation of a positively charged species have been met, other functional groups may influence the hybridization process. The five fold increase in efficiency for histidine and related molecules over imidazole alone may reflect histidine's ability to sustain a positive charge on both the imidazole ring as well as the primary amine. Like simple dicationic salts such as $Mg^{++}$, this double positive charge may be more efficient at diminishing backbone repulsion. Further modification of these zwitterions may lead to additional increases in hybridization efficiency.

The utility of these microelectronic devices is just beginning to be explored. As we come to understand more clearly the behavior of these devices and the conditions that allow their optimal use, their utility may be extended from nucleic acids to the use of other charged species. Ultimately, they may allow replacement of our present macromolecular biology devices by suitable microscopic devices.

While DNA is used as a primary example, the above described device and method can also be used for the processing and analysis of target RNA molecules, proteins, polysaccharides, lipids and other macromolecules.

All publications referenced are hereby incorporated by reference herein, including the nucleic acid sequences and amino acid sequences listed in each publication.

Example 14

Electronic Hybridization and Single Base Mismatch Analysis of Double-Stranded DNA Fragments The following describes the basic experimental procedure to carry out rapid electronic hybridization and single base mismatch discrimination in samples containing substantially double-stranded (ds) nucleic acid target sequences. In this example, the target material was a 123 base pair (bp) PCR amplicon of β-globin sequence amplified from Sickle Cell positive human placental tissue. The β-globin sequence contains the Sickle Cell mutation site (codon 7) in which there is an A - - - > T base conversion.

The standard 25 position APEX chip with 80 micron test sites (microlocations) was used for these experiments. The chip was covered with a 0.7 micron layer of thick/thin agarose (see Experiment 13), in which the upper layer contained streptavidin to provide attachment sites for the biotinylated capture probe oligonucleotides to be addressed. Three different capture probes were electronically addressed to test site (column) positions 2, 3, and 4 in each of the five rows of test sites on the 25 microlocation APEX chip. These capture probes were (1) GCAP-1, a 24-mer sequence which is the complement to the wild type β-globin target sequence; GCAP-2 a 24-mer sequence which is a complement to the mismatch (mutated) sequence; and ATA4, a 17-mer which is non-complementary to the β-globin target sequence. The sequences are shown below:

GCAP-1 5'-CAGACTTCTCC(T) CAGGAGTCAGGT-3'-Biotin

GCAP-2 5'-CAGACTTCTCC(A) CAGGAGTCAGGT-3'-Biotin

ATA-4 5'-GTCTCCTTCCTCTCCAG-3'-Biotin

The above capture probes were addressed using the following procedure. Each capture probe was made up at a concentration of about 500 uM in 50 mM histidine (pH 7.4). About 5 ul of the GCAP-1 capture probe solution was placed on the active area of the chip surface and electronically addressed to the five microlocations in column number 2. Electronic addressing condition were 200 nanoamperes (nA) per microlocation for one minute, with addressed location biased positive relative to the perimeter control pads biased negative. The chip was then rinsed off with 50 mM histidine. Next, about 5 ul of the GCAP-2 capture probe solution was placed on the active area of the chip surface and electronically addressed to the five microlocations in column number 3. Electronic addressing condition were 200 nA per microlocation for one minute, with addressed location biased positive relative to the perimeter control pads biased negative.

Finally, about 5 ul of the ATA-4 capture probe solution was placed on the active area of the chip surface and electronically addressed to the five microlocations in column number 4. Electronic addressing condition were 200 nA per microlocation for one minute, with addressed location biased positive relative to the perimeter control pads biased negative.

PCR amplification of Sickle Cell positive human placental tissue was carried out using standard PCR conditions. Approximately 2vl of the PCR amplified material was now taken directly from the PCR reaction tube and mixed with 98 vl of 50 mM histidine (pH 7.4), the sample was heated to 100 ° C. and quickly cooled to room temperature. About 5 vl of this sample was then placed directly on the chip surface. The three test locations (in columns 2, 3 and 4) in each row (1 through 5), were then electronically hybridized by applying a positive bias to the three test microlocations (relative to negative bias on the perimeter control electrodes) producing a direct current flow of 1.8 vA (600 nA per test site) for 2 minutes. After electronic hybridization to the test sites, the chip was washed with the histidine buffer and a 40 mM sodium phosphate/500 mM sodium chloride (pH 7.4) buffer. The chip was then passively hybridized for 5 minutes with fluorescent (bytr) reporter probe complementary to another section of the target amplicon sequence. It should be pointed out that this step is not necessary if the amplicon has a fluorescent label already incorporated (via one of the PCR primers), or if the hybrids are detected using one of the intercalating dye techniques. After the reporter probe hybridization, the chip is washed with histidine buffer. Electronic stringency was then carried out in 20 mM sodium phosphate/Tris (pH 9.5), using 150 DC pulses (0.1 second/ 0.1 second off) for 30 seconds (per three test sites in each row) at the current level shown below:

| Row | Current (vA)/3 pads | MisMatch/Match Ratio |
|-----|---------------------|----------------------|
| (1) | 1.6 | 1.3 to 1 |
| (2) | 1.7 | 1.4 to 1 |
| (3) | 1.8 | 2.0 to 1 |
| (4) | 1.9 | 1.8 to 1 |
| (5) | 1.8 | 1.7 to 1 |

The Match/MisMatch ratios were determined by measuring the relative difference in fluorescent intensity on the test microlocation after electronic stringency was applied. As can be seen, the most optimal electronic stringency was about 1.8 to 1.9 vA for three sites, or 600 to 630 nA per site.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

What is claimed is:

1. A method for enhancing the hybridization efficiency of target nucleic acids in a microelectronic hybridization device including a microlocation test site having a capture nucleic acid, the microlocation adapted to be placed at least in a first state wherein no electric field is generated and in a second state wherein an electric field attractive to the target nucleic acids is generated at the microlocation, comprising the steps of:

applying a buffer to the device, providing target nucleic acid to the device, placing the microlocation in the said second state through application of power to the device to cause accumulation of the target nucleic acids at a microlocation test site on the device, and hybridizing the target nucleic acids with the capture nucleic acid with an efficiency which is greater in the said second state than in the said first state.

2. The method of claim 1 wherein the buffer is a zwitterionic buffer.

3. The method of claim 2 wherein the zwitterionic buffer includes histidine.

4. The method of claim 3 wherein the histidine was prepared at a concentration of about 10–100 mM.

5. The method of claim 3 wherein the histidine was prepared at or about the isoelectric point.

6. The method of claim 2 wherein the isoelectric point is about pH 7.47.

7. The method of claim 2 wherein the buffer entity stabilizes hybridization between the target nucleic acids and the capture nucleic acid in the said second state.

8. The method of claim 1 wherein the buffer entity reduces repulsion between the capture nucleic acid and the target nucleic acids in the said second state.

9. The method of claim 1 wherein the buffer reduces adduct formation between the capture nucleic acid and the target nucleic acids.

* * * * *